United States Patent
Laumont et al.

(10) Patent No.: US 11,702,450 B2
(45) Date of Patent: Jul. 18, 2023

(54) PROTEOGENOMIC-BASED METHOD FOR IDENTIFYING TUMOR-SPECIFIC ANTIGENS

(71) Applicant: UNIVERSITÉ DE MONTRÉAL, Montreal (CA)

(72) Inventors: Céline Laumont, Victoria (CA); Pierre Thibault, Montreal (CA); Sébastien Lemieux, Lasalle (CA); Claude Perreault, Montreal (CA)

(73) Assignee: UNIVERSITÉ DE MONTRÉAL, Montreal (CA)

( * ) Notice: Subject to any disclaimer, the term of this patent is extended or adjusted under 35 U.S.C. 154(b) by 120 days.

(21) Appl. No.: 17/267,914

(22) PCT Filed: Aug. 28, 2019

(86) PCT No.: PCT/CA2019/051186
§ 371 (c)(1),
(2) Date: Feb. 11, 2021

(87) PCT Pub. No.: WO2020/041876
PCT Pub. Date: Mar. 5, 2020

(65) Prior Publication Data
US 2021/0253638 A1 Aug. 19, 2021

Related U.S. Application Data

(60) Provisional application No. 62/724,760, filed on Aug. 30, 2018.

(51) Int. Cl.
C07K 7/06 (2006.01)
A61P 35/02 (2006.01)
C07K 14/74 (2006.01)
A61K 38/00 (2006.01)

(52) U.S. Cl.
CPC ............... *C07K 7/06* (2013.01); *A61P 35/02* (2018.01); *C07K 14/70539* (2013.01); *A61K 38/00* (2013.01)

(58) Field of Classification Search
None
See application file for complete search history.

(56) References Cited

FOREIGN PATENT DOCUMENTS

WO WO 00/42181 A1 7/2000
WO WO 2020/257922 A1 12/2020

OTHER PUBLICATIONS

Chadburn, A., Inghirami, G. & Knowles, D.M. Hairy cell leukemia-associated antigen LeuM5 (CD11c) is preferentially expressed by benign activated and neoplastic CD8 T cells. Am J Pathol 136, 29-37 (1990).
Nesvizhskii, A.I. Proteogenomics: concepts, applications and computational strategies. Nat Methods 11, 1114-1125 (2014).
Noble, W.S. Mass spectrometrists should only search for peptides they care about. Nat Methods 12, 605-608 (2015).
Murphy, J.P., et al. MHC-I Ligand Discovery Using Targeted Database Searches of Mass Spectrometry Data: Implications for T-Cell Immunotherapies. J Proteome Res 16, 1806-1816 (2017).
Granados, D.P., et al. Impact of genomic polymorphisms on the repertoire of human MHC class I-associated peptides. Nat Commun 5, 3600 (2014).
Bassani-Sternberg, M., Pletscher-Frankild, S., Jensen, L.J. & Mann, M. Mass spectrometry of human leukocyte antigen class I peptidomes reveals strong effects of protein abundance and turnover on antigen presentation. Mol Cell Proteomics 14, 658-673 (2015).
Fortier, M.H., et al. The MHC class I peptide repertoire is molded by the transcriptome. J Exp Med 205, 595-610 (2008).
Jenkins, M.K. & Moon, J.J. The role of naive T cell precursor frequency and recruitment in dictating immune response magnitude. J Immunol 188, 4135-4140 (2012).
Obar, J.J., Khanna, K.M. & Lefrancois, L. Endogenous naive CD8+ T cell precursor frequency regulates primary and memory responses to infection. Immunity 28, 859-869 (2008).
La Gruta, N.L., et al. Primary CTL response magnitude in mice is determined by the extent of naive T cell recruitment and subsequent clonal expansion. J Clin Invest 120, 1885-1894 (2010).
Mueller, S.N., Gebhardt, T., Carbone, F.R. & Heath, W.R. Memory T cell subsets, migration patterns, and tissue residence. Annu Rev Immunol 31, 137-161 (2013).
Baaten, B.J., Tinoco, R., Chen, A.T. & Bradley, L.M. Regulation of Antigen-Experienced T Cells: Lessons from the Quintessential Memory Marker CD44. Front Immunol 3, 23 (2012).
Laugel, B., et al. Different T cell receptor affinity thresholds and CDS coreceptor dependence govern cytotoxic T lymphocyte activation and tetramer binding properties. J Biol Chem 282, 23799-23810 (2007).
Richards, D.M., Kyewski, B. & Feuerer, M. Re-examining the Nature and Function of Self-Reactive T cells. Trends Immunol 37, 114-125 (2016).
McGranahan, N., et al. Clonal neoantigens elicit T cell immunoreactivity and sensitivity to immune checkpoint blockade. Science 351, 1463-1469 (2016).

(Continued)

*Primary Examiner* — Ronald T Niebauer
(74) *Attorney, Agent, or Firm* — James S. Keddie; Bozicevic, Field & Francis LLP

(57) ABSTRACT

T cells, notably CD8 T cells, are known to be essential players in tumor eradication as the presence of tumor-infiltrating lymphocytes (TILS) in several cancers positively correlates with a good prognosis. To eliminate tumor cells, CD8 T cells recognize tumor antigens, which are MHC I-associated peptides present at the surface of tumor cells, with no or very low expression on normal cells. Described herein a proteogenomic approach using RNA-sequencing data from cancer and normal-matched mTEC$^{hi}$ samples in order to identify non-tolerogenic tumor-specific antigens derived from (i) coding and non-coding regions of the genome, (ii) non-synonymous single-base mutations or short insertion/deletions and more complex rearrangements as well as (iii) endogenous retroelements, which works regardless of the sample's mutational load or complexity.

13 Claims, 27 Drawing Sheets
Specification includes a Sequence Listing.

(56) References Cited

OTHER PUBLICATIONS

Assarsson, E., et al. A quantitative analysis of the variables affecting the repertoire of T cell specificities recognized after vaccinia virus infection. J Immunol 178, 7890-7901 (2007).

Martin, S.D., et al. Low Mutation Burden in Ovarian Cancer May Limit the Utility of Neoantigen-Targeted Vaccines. PLoS One 11, e0155189 (2016).

Rudensky, A., Preston-Hurlburt, P., Hong, S.C., Barlow, A. & Janeway, C.A., Jr. Sequence analysis of peptides bound to MHC class II molecules. Nature 353, 622-627 (1991).

Meydan, C., Otu, H.H. & Sezerman, O.U. Prediction of peptides binding to MHC class I and II alleles by temporal motif mining. BMC Bioinformatics 14 Suppl 2, S13 (2013).

Szpakowski, S., et al. Loss of epigenetic silencing in tumors preferentially affects primate-specific retroelements. Gene 448, 151-167 (2009).

Capietto, A.H., Jhunjhunwala, S. & Delamarre, L. Characterizing neoantigens for personalized cancer immunotherapy. Curr Opin Immunol 46, 58-65 (2017).

Helft, J., et al. GM-CSF Mouse Bone Marrow Cultures Comprise a Heterogeneous Population of CD11c(+)MHCII(+) Macrophages and Dendritic Cells. Immunity 42, 1197-1211 (2015).

Wimmers, F., Schreibelt, G., Skold, A.E., Figdor, C.G. & De Vries, I.J. Paradigm Shift in Dendritic Cell-Based Immunotherapy: From in vitro Generated Monocyte-Derived DCs to Naturally Circulating DC Subsets. Front Immunol 5, 165 (2014).

Guilliams, M. & Malissen, B. A Death Notice for In-Vitro-Generated GM-CSF Dendritic Cells? Immunity 42, 988-990 (2015).

Melief, C.J., van Hall, T., Arens, R., Ossendorp, F. & van der Burg, S.H. Therapeutic cancer vaccines. J Clin Invest 125, 3401-3412 (2015).

Guo, C., et al. Therapeutic cancer vaccines: past, present, and future. Adv Cancer Res 119, 421-475 (2013).

Melero, I., et al. Therapeutic vaccines for cancer: an overview of clinical trials. Nat Rev Clin Oncol 11, 509-524 (2014).

Baruch, E.N., Berg, A.L., Besser, M.J., Schachter, J. & Markel, G. Adoptive T cell therapy: An overview of obstacles and opportunities. Cancer 123, 2154-2162 (2017).

Rosenberg, S.A. & Restifo, N.P. Adoptive cell transfer as personalized immunotherapy for human cancer. Science 348, 62-68 (2015).

Stoeckle, C., et al. Isolation of myeloid dendritic cells and epithelial cells from human thymus. J Vis Exp, e50951 (2013).

Marcais, G. & Kingsford, C. A fast, lock-free approach for efficient parallel counting of occurrences of k-mers. Bioinformatics 27, 764-770 (2011).

Lanoix, J., et al. Comparison of the MHC I immunopeptidome repertoire of B-cell lymphoblasts using two isolation methods. Proteomics, e1700251 (2018).

Daouda, T., Perreault, C. & Lemieux, S. pyGeno: A python package for precision medicine and proteogenomics. F1000Res 5, 381 (2016).

Sloan, C.A., et al. ENCODE data at the ENCODE portal. Nucleic Acids Res 44, D726-732 (2016).

Vincent, K., et al. Rejection of leukemic cells requires antigen-specific T cells with high functional avidity. Biol Blood Marrow Transplant 20, 37-45 (2014).

Vizcaino, J.A., et al. 2016 update of the PRIDE database and its related tools. Nucleic Acids Res 44, 11033 (2016).

International Search Report and Written Opinion in respect of PCT/CA2019/051186, dated Nov. 19, 2019.

Dart Anna, Expanding the search, Nature Reviews Cancer, vol. 19, No. 3, pp. 126-127, Mar. 2019.

Laumont et al., Global proteogenomic analysis of human MHC class I-associated peptides derived from non-canonical reading frames. Nature Communications, Jan. 2016, 7:10238. ISSN 2041-1723.

Laumont et al., Exploiting non-canonical translation to identify new targets for T cell-based cancer immunotherapy, Cell. Mol. Life Sci., Feb. 2018, 75:607-621. ISSN 1420-9071.

Cifani, P. et al., ProteomeGenerator: A Framework for Comprehensive Proteomics Based on de Novo Transcriptome Assembly and High-Accuracy Peptide Mass Spectral Matching, J. Proteome Res., Nov. 2018, 17: 3681-3692. ISSN 1535-3907.

Laumont et al., Noncoding regions are the main source of targetable tumor-specific antigens, Sci. Transl. Med, Dec. 2018, 10: eaau5516. ISSN 1946-6242.

Mlecnik, B., et al. The tumor microenvironment and immunoscore are critical determinants of dissemination to distant metastasis. Sci Transl Med 8, 327ra326 (2016).

Charoentong, P., et al. Pan-cancer immunogenomic analyses reveal genotype-immunophenotype relationships and predictors of response to checkpoint blockade. Cell Rep 18, 248-262 (2017).

Shao, W., et al. The systeMHC Atlas project. Nucleic Acids Res 46, D1237-D1247 (2018).

Martin, S.D., Coukos, G., Holt, R.A. & Nelson, B.H. Targeting the undruggable: Immunotherapy meets personalized oncology in the genomic era. Ann Oncol 26, 2367-2374 (2015).

Marty, R., et al. MHC-I genotype restricts the oncogenic mutational landscape. Cell 171, 1272-1283 e1215 (2017).

Zhong, S., et al. T-cell receptor affinity and avidity defines antitumor response and autoimmunity in T-cell immunotherapy. Proc Natl Acad Sci USA 110, 6973-6978 (2013).

Sahin, U., et al. Personalized RNA mutanome vaccines mobilize poly-specific therapeutic immunity against cancer. Nature 547, 222-226 (2017).

Turajlic, S., et al. Insertion-and-deletion-derived tumour-specific neoantigens and the immunogenic phenotype: a pan-cancer analysis. Lancet Oncol 18, 1009-1021 (2017).

Yadav, M., et al. Predicting immunogenic tumour mutations by combining mass spectrometry and exome sequencing. Nature 515, 572-576 (2014).

Pearson, H., et al. MHC class I-associated peptides derive from selective regions of the human genome. J Clin Invest 126, 4690-4701 (2016).

Tran, E., et al. Immunogenicity of somatic mutations in human gastrointestinal cancers. Science 350, 1387-1390 (2015).

Gros, A., et al. Prospective identification of neoantigen-specific lymphocytes in the peripheral blood of melanoma patients. Nat Med 22, 433-438 (2016).

Bassani-Sternberg, M., et al. Direct identification of clinically relevant neoepitopes presented on native human melanoma tissue by mass spectrometry. Nat Commun 7, 13404 (2016).

Mertens, F., Johansson, B., Fioretos, T. & Mitelman, F. The emerging complexity of gene fusions in cancer. Nat Rev Cancer 15, 371-381 (2015).

Baca, S.C., et al. Punctuated evolution of prostate cancer genomes. Cell 153, 666-677 (2013).

Hayward, N.K., et al. Whole-genome landscapes of major melanoma subtypes. Nature 545, 175-180 (2017).

Khurana, E., et al. Role of non-coding sequence variants in cancer. Nat Rev Genet 17, 93-108 (2016).

Rooney, M.S., Shukla, S.A., Wu, C.J., Getz, G. & Hacohen, N. Molecular and genetic properties of tumors associated with local immune cytolytic activity. Cell 160, 48-61 (2015).

Anwar, S.L., Wulaningsih, W. & Lehmann, U. Transposable Elements in Human Cancer: Causes and Consequences of Deregulation. Int J Mol Sci 18 (2017).

Kassiotis, G. & Stoye, J.P. Immune responses to endogenous retroelements: taking the bad with the good. Nat Rev Immunol 16, 207-219 (2016).

Kershaw, M.H., et al. Immunization against endogenous retroviral tumor-associated antigens. Cancer Res 61, 7920-7924 (2001).

Sacha, J.B., et al. Vaccination with cancer- and HIV infection-associated endogenous retrotransposable elements is safe and immunogenic. J Immunol 189, 1467-1479 (2012).

Malarkannan, S., Serwold, T., Nguyen, V., Sherman, L.A. & Shastri, N. The mouse mammary tumor virus env gene is the source of a CD8+ T-cell-stimulating peptide presented by a major histocompatibility complex class I molecule in a murine thymoma. Proc Natl Acad Sci U S A 93, 13991-13996 (1996).

(56) References Cited

OTHER PUBLICATIONS

Huang, A.Y., et al. The immunodominant major histocompatibility complex class I-restricted antigen of a murine colon tumor derives from an endogenous retroviral gene product. Proc Natl Acad Sci U S A 93, 9730-9735 (1996).
Schiavetti, F., Thonnard, J., Colau, D., Boon, T. & Coulie, P.G. A human endogenous retroviral sequence encoding an antigen recognized on melanoma by cytolytic T lymphocytes. Cancer Res 62, 5510-5516 (2002).
Takahashi, Y., et al. Regression of human kidney cancer following allogeneic stem cell transplantation is associated with recognition of an HERV-E antigen by T cells. J Clin Invest 118, 1099-1109 (2008).
Kim, M.J., Miller, C.M., Shadrach, J.L., Wagers, A.J. & Serwold, T. Young, proliferative thymic epithelial cells engraft and function in aging thymuses. J Immunol 194, 4784-4795 (2015).
Dobin, A., et al. STAR: ultrafast universal RNA-seq aligner. Bioinformatics 29, 15-21 (2013).
Quinlan, A.R. & Hall, I.M. BEDTools: a flexible suite of utilities for comparing genomic features. Bioinformatics 26, 841-842 (2010).
Caron, E., et al. The MHC I immunopeptidome conveys to the cell surface an integrative view of cellular regulation. Mol Syst Biol 7, 533 (2011).
Andreatta, M. & Nielsen, M. Gapped sequence alignment using artificial neural networks: application to the MHC class I system. Bioinformatics 32, 511-517 (2016).
Robinson, J.T., et al. Integrative genomics viewer. Nat Biotechnol 29, 24-26 (2011).
Bereman, M.S., et al. An Automated Pipeline to Monitor System Performance in Liquid Chromatography-Tandem Mass Spectrometry Proteomic Experiments. J Proteome Res 15, 4763-4769 (2016).
Yue, F., et al. A comparative encyclopedia of DNA elements in the mouse genome. Nature 515, 355-364 (2014).
Barbosa-Morais, N.L., et al. The evolutionary landscape of alternative splicing in vertebrate species. Science 338, 1587-1593 (2012).
Patenaude, J. & Perreault, C. Thymic Mesenchymal Cells Have a Distinct Transcriptomic Profile. J Immunol 196, 4760-4770 (2016).
St-Pierre, C., Trofimov, A., Brochu, S., Lemieux, S. & Perreault, C. Differential Features of AIRE-Induced and AIRE-Independent Promiscuous Gene Expression in Thymic Epithelial Cells. J Immunol 195, 498-506 (2015).
Dumont-Lagace, M., St-Pierre, C. & Perreault, C. Sex hormones have pervasive effects on thymic epithelial cells. Sci Rep 5, 12895 (2015).
Dumont-Lagace, M., Brochu, S., St-Pierre, C. & Perreault, C. Adult thymic epithelium contains nonsenescent label-retaining cells. J Immunol 192, 2219-2226 (2014).
De Verteuil, D.A., et al. Immunoproteasomes shape the transcriptome and regulate the function of dendritic cells. J Immunol 193, 1121-1132 (2014).
De Verteuil, D., et al. Deletion of immunoproteasome subunits imprints on the transcriptome and has a broad impact on peptides presented by major histocompatibility complex I molecules. Mol Cell Proteomics 9, 2034-2047 (2010).
Moon, J.J., et al. Naive CD4(+) T cell frequency varies for different epitopes and predicts repertoire diversity and response magnitude. Immunity 27, 203-213 (2007).
Legoux, F.P. & Moon, J.J. Peptide:MHC tetramer-based enrichment of epitope-specific T cells. J Vis Exp (2012).
McFarland, H.I., Nahill, S.R., Maciaszek, J.W. & Welsh, R.M. CD11b (Mac-1): a marker for CD8+ cytotoxic T cell activation and memory in virus infection. J Immunol 149, 1326-1333 (1992).
Database Epop [Online], Li et al., "Sequence 26 from Patent EP2749573", XP055936770, Database accession No. JC488772, Sep. 2014.
Guilloux et al, "A Peptide Recognized by Human Cytolytic T Lymphocytes on HLA-A2 Melanomas Is Encoded by an Intron Sequence of the N-Acetylglucosaminyltransferase V Gene", J. Exp. Med., 1996, 183: 1173-1183.
Laumont et al., "Global proteogenomic analysis of human MHC class I-associated peptides derived from non-canonical reading frames", Nature Communications, 2016, 7:10238, 1-12.
Smart et al., "Intron retention is a source of neoepitopes in cancer", Nature Biotechnology, Aug. 2018, 36 (11): 1056-1058.
Yasumoto et al., "Lung cancer-associated tumor antigens and the present status of immunotherapy against non-small-cell lung cancer", Gen Thorac Cardiovasc Surg, 2009, 57: 449-457.
Zhu et al., "Discovery of coding regions in the human genome by integrated proteogenomics analysis workflow", Nature Communications, Mar. 2018, 9:903, 1-14.

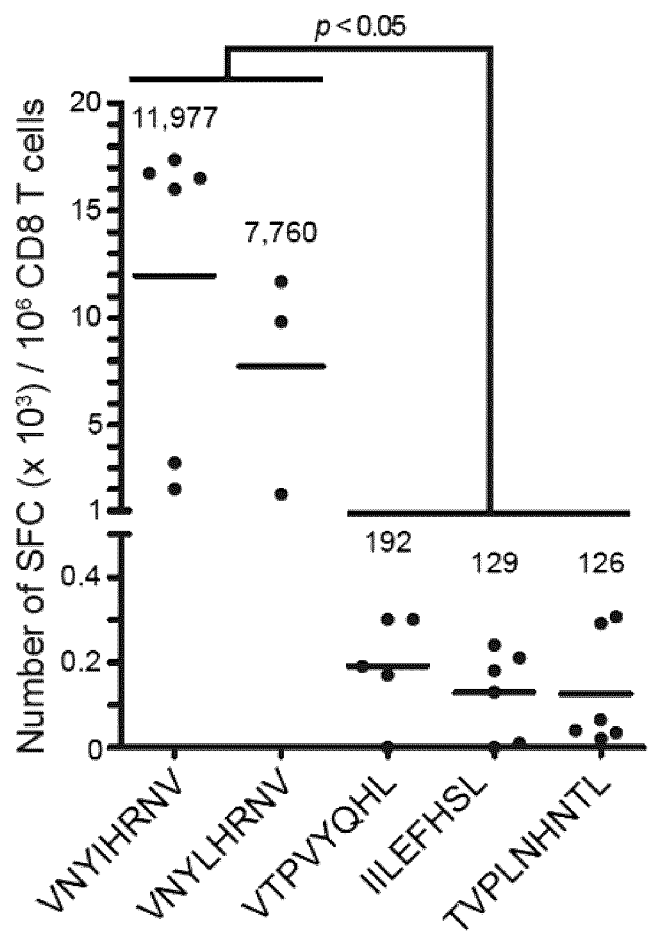
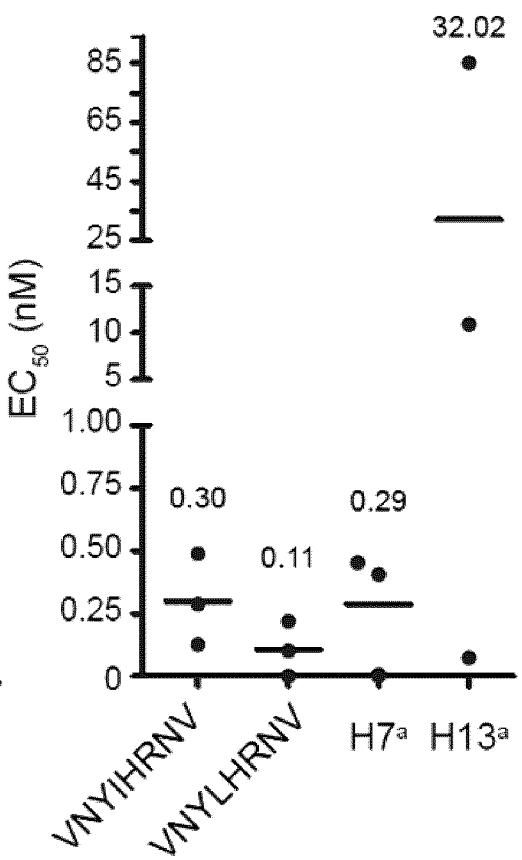
FIG. 4C
FIG. 4D
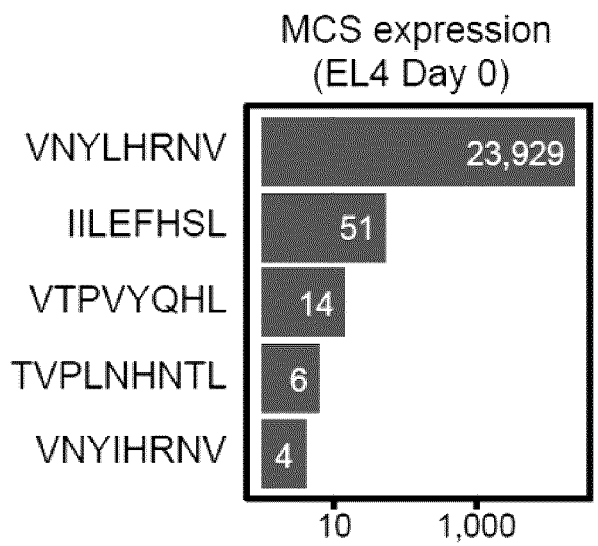
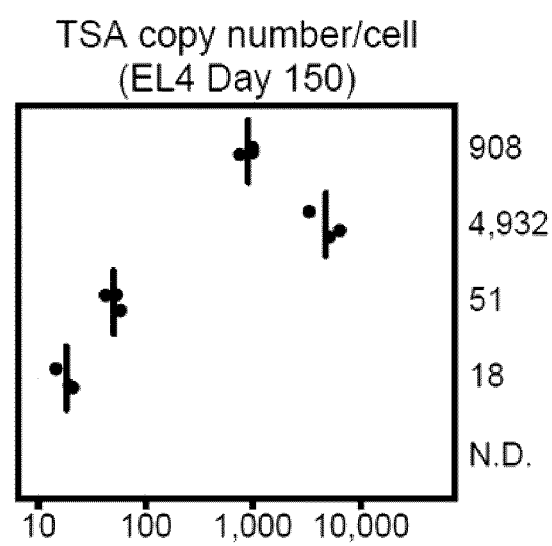
FIG. 5A
FIG. 5B

FIG. 7C  FIG. 7D

SEQUENCE LISTING

```
<160> NUMBER OF SEQ ID NOS: 80

<210> SEQ ID NO 1
<211> LENGTH: 9
<212> TYPE: PRT
<213> ORGANISM: Mus musculus

<400> SEQUENCE: 1

Gly Tyr Gln Lys Met Lys Ala Leu Leu
1               5

<210> SEQ ID NO 2
<211> LENGTH: 9
<212> TYPE: PRT
<213> ORGANISM: Mus musculus
<220> FEATURE:
<221> NAME/KEY: VARIANT
<222> LOCATION: (4)..(4)
<223> OTHER INFORMATION: Xaa is Lys or Glu

<400> SEQUENCE: 2

Lys Pro Leu Xaa Ala Pro Leu Asp Leu
1               5
```

```
<210> SEQ ID NO 3
<211> LENGTH: 9
<212> TYPE: PRT
<213> ORGANISM: Mus musculus
<220> FEATURE:
<221> NAME/KEY: VARIANT
<222> LOCATION: (7)..(7)
<223> OTHER INFORMATION: Xaa is Ser or Gly

<400> SEQUENCE: 3

Lys Tyr Leu Ser Val Gln Xaa Gln Leu
1               5

<210> SEQ ID NO 4
<211> LENGTH: 10
<212> TYPE: PRT
<213> ORGANISM: Mus musculus
<220> FEATURE:
<221> NAME/KEY: VARIANT
<222> LOCATION: (7)..(7)
<223> OTHER INFORMATION: Xaa is Ser or Gly

<400> SEQUENCE: 4

Lys Tyr Leu Ser Val Gln Xaa Gln Leu Phe
1               5                   10

<210> SEQ ID NO 5
<211> LENGTH: 11
<212> TYPE: PRT
<213> ORGANISM: Mus musculus

<400> SEQUENCE: 5

Leu Pro Gln Glu Leu Pro Gly Leu Val Val Leu
1               5                   10

<210> SEQ ID NO 6
<211> LENGTH: 11
<212> TYPE: PRT
<213> ORGANISM: Mus musculus

<400> SEQUENCE: 6

Met Pro His Ser Leu Leu Pro Leu Val Thr Phe
1               5                   10

<210> SEQ ID NO 7
<211> LENGTH: 9
<212> TYPE: PRT
<213> ORGANISM: Mus musculus
<220> FEATURE:
<221> NAME/KEY: VARIANT
<222> LOCATION: (8)..(8)
<223> OTHER INFORMATION: Xaa is Ile or Leu

<400> SEQUENCE: 7

Gln Gly Pro Met Ala Leu Arg Xaa Phe
1               5

<210> SEQ ID NO 8
<211> LENGTH: 9
<212> TYPE: PRT
<213> ORGANISM: Mus musculus

<400> SEQUENCE: 8

Ser Gly Pro Pro Tyr Tyr Lys Gly Ile
1               5
```

```
<210> SEQ ID NO 9
<211> LENGTH: 8
<212> TYPE: PRT
<213> ORGANISM: Mus musculus

<400> SEQUENCE: 9

Ser Pro His Gln Val Phe Asn Leu
1               5

<210> SEQ ID NO 10
<211> LENGTH: 9
<212> TYPE: PRT
<213> ORGANISM: Mus musculus

<400> SEQUENCE: 10

Ser Pro Ser Tyr Val Tyr His Gln Phe
1               5

<210> SEQ ID NO 11
<211> LENGTH: 8
<212> TYPE: PRT
<213> ORGANISM: Mus musculus

<400> SEQUENCE: 11

Ala Thr Gln Gln Phe Gln Gln Leu
1               5

<210> SEQ ID NO 12
<211> LENGTH: 8
<212> TYPE: PRT
<213> ORGANISM: Mus musculus

<400> SEQUENCE: 12

Ile Ile Leu Glu Phe His Ser Leu
1               5

<210> SEQ ID NO 13
<211> LENGTH: 9
<212> TYPE: PRT
<213> ORGANISM: Mus musculus

<400> SEQUENCE: 13

Ser Ser Pro Arg Gly Ser Ser Thr Leu
1               5

<210> SEQ ID NO 14
<211> LENGTH: 9
<212> TYPE: PRT
<213> ORGANISM: Mus musculus

<400> SEQUENCE: 14

Thr Val Pro Leu Asn His Asn Thr Leu
1               5

<210> SEQ ID NO 15
<211> LENGTH: 8
<212> TYPE: PRT
<213> ORGANISM: Mus musculus
<220> FEATURE:
<221> NAME/KEY: VARIANT
<222> LOCATION: (4)..(4)
<223> OTHER INFORMATION: Xaa is Ile or Leu

<400> SEQUENCE: 15

Val Asn Tyr Xaa His Arg Asn Val
```

```
<210> SEQ ID NO 16
<211> LENGTH: 8
<212> TYPE: PRT
<213> ORGANISM: Mus musculus

<400> SEQUENCE: 16

Val Thr Pro Val Tyr Gln His Leu
1               5

<210> SEQ ID NO 17
<211> LENGTH: 9
<212> TYPE: PRT
<213> ORGANISM: Homo sapiens

<400> SEQUENCE: 17

Lys Ile Leu Ile Leu Leu Gln Ser Leu
1               5

<210> SEQ ID NO 18
<211> LENGTH: 9
<212> TYPE: PRT
<213> ORGANISM: Homo sapiens

<400> SEQUENCE: 18

Lys Ile Ser Leu Tyr Leu Pro Ala Leu
1               5

<210> SEQ ID NO 19
<211> LENGTH: 9
<212> TYPE: PRT
<213> ORGANISM: Homo sapiens

<400> SEQUENCE: 19

Ser Leu Thr Ala Leu Val Phe His Val
1               5

<210> SEQ ID NO 20
<211> LENGTH: 8
<212> TYPE: PRT
<213> ORGANISM: Homo sapiens

<400> SEQUENCE: 20

His Glu Thr Leu Arg Leu Leu Leu
1               5

<210> SEQ ID NO 21
<211> LENGTH: 9
<212> TYPE: PRT
<213> ORGANISM: Homo sapiens

<400> SEQUENCE: 21

Arg Ile Phe Gly Phe Arg Leu Trp Lys
1               5

<210> SEQ ID NO 22
<211> LENGTH: 9
<212> TYPE: PRT
<213> ORGANISM: Homo sapiens

<400> SEQUENCE: 22

Thr Ser Phe Ala Glu Thr Trp Met Lys
1               5
```

```
<210> SEQ ID NO 23
<211> LENGTH: 9
<212> TYPE: PRT
<213> ORGANISM: Homo sapiens

<400> SEQUENCE: 23

Thr Ser Ile Pro Lys Pro Asn Leu Lys
1               5

<210> SEQ ID NO 24
<211> LENGTH: 8
<212> TYPE: PRT
<213> ORGANISM: Homo sapiens

<400> SEQUENCE: 24

Leu Pro Phe Glu Gln Lys Ser Leu
1               5

<210> SEQ ID NO 25
<211> LENGTH: 9
<212> TYPE: PRT
<213> ORGANISM: Homo sapiens

<400> SEQUENCE: 25

Ser Leu Arg Glu Lys Gly Phe Ser Ile
1               5

<210> SEQ ID NO 26
<211> LENGTH: 8
<212> TYPE: PRT
<213> ORGANISM: Homo sapiens

<400> SEQUENCE: 26

Val Pro Ala Ala Leu Arg Ser Leu
1               5

<210> SEQ ID NO 27
<211> LENGTH: 10
<212> TYPE: PRT
<213> ORGANISM: Homo sapiens

<400> SEQUENCE: 27

Leu Leu Ala Ala Thr Ile Leu Leu Ser Val
1               5                   10

<210> SEQ ID NO 28
<211> LENGTH: 9
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa is Ala or Val

<400> SEQUENCE: 28

Ser Leu Phe Val Xaa Ser Leu Ser Leu
1               5

<210> SEQ ID NO 29
<211> LENGTH: 9
<212> TYPE: PRT
<213> ORGANISM: Homo sapiens

<400> SEQUENCE: 29

Ile Ile Ala Pro Pro Pro Pro Pro Lys
```

<210> SEQ ID NO 30
<211> LENGTH: 9
<212> TYPE: PRT
<213> ORGANISM: Homo sapiens

<400> SEQUENCE: 30

Leu Val Phe Asn Ile Ile Leu His Arg
1               5

<210> SEQ ID NO 31
<211> LENGTH: 9
<212> TYPE: PRT
<213> ORGANISM: Homo sapiens

<400> SEQUENCE: 31

Met Ile Ser Pro Val Leu Ala Leu Lys
1               5

<210> SEQ ID NO 32
<211> LENGTH: 9
<212> TYPE: PRT
<213> ORGANISM: Homo sapiens

<400> SEQUENCE: 32

Ser Leu Ser Tyr Leu Ile Leu Lys Lys
1               5

<210> SEQ ID NO 33
<211> LENGTH: 9
<212> TYPE: PRT
<213> ORGANISM: Homo sapiens

<400> SEQUENCE: 33

Ser Ser Ala Ser Gln Leu Pro Ser Lys
1               5

<210> SEQ ID NO 34
<211> LENGTH: 10
<212> TYPE: PRT
<213> ORGANISM: Homo sapiens

<400> SEQUENCE: 34

Ser Val Ile Gln Thr Gly His Leu Ala Lys
1               5                   10

<210> SEQ ID NO 35
<211> LENGTH: 9
<212> TYPE: PRT
<213> ORGANISM: Homo sapiens

<400> SEQUENCE: 35

Thr Thr Leu Lys Tyr Leu Trp Lys Lys
1               5

<210> SEQ ID NO 36
<211> LENGTH: 9
<212> TYPE: PRT
<213> ORGANISM: Homo sapiens

<400> SEQUENCE: 36

Lys Pro Ser Val Phe Pro Leu Ser Leu
1               5

```
<210> SEQ ID NO 37
<211> LENGTH: 9
<212> TYPE: PRT
<213> ORGANISM: Homo sapiens
<220> FEATURE:
<221> NAME/KEY: VARIANT
<222> LOCATION: (2)..(2)
<223> OTHER INFORMATION: Xaa is Arg or Lys
<220> FEATURE:
<221> NAME/KEY: VARIANT
<222> LOCATION: (3)..(3)
<223> OTHER INFORMATION: Xaa is Phe or Leu

<400> SEQUENCE: 37

Gln Xaa Xaa Gln Gly Arg Val Thr Met
1               5

<210> SEQ ID NO 38
<211> LENGTH: 10
<212> TYPE: PRT
<213> ORGANISM: Homo sapiens

<400> SEQUENCE: 38

Ser Arg Phe Ser Gly Val Pro Asp Arg Phe
1               5                   10

<210> SEQ ID NO 39
<211> LENGTH: 9
<212> TYPE: PRT
<213> ORGANISM: Homo sapiens
<220> FEATURE:
<221> NAME/KEY: VARIANT
<222> LOCATION: (5)..(5)
<223> OTHER INFORMATION: Xaa is Asn or Asp

<400> SEQUENCE: 39

Thr Tyr Thr Gln Xaa Phe Asn Lys Phe
1               5

<210> SEQ ID NO 40
<211> LENGTH: 9
<212> TYPE: PRT
<213> ORGANISM: Lymphocytic choriomeningitis virus

<400> SEQUENCE: 40

Lys Ala Val Tyr Asn Phe Ala Thr Cys
1               5

<210> SEQ ID NO 41
<211> LENGTH: 9
<212> TYPE: PRT
<213> ORGANISM: Murine cytomegalovirus

<400> SEQUENCE: 41

His Gly Ile Arg Asn Ala Ser Phe Ile
1               5

<210> SEQ ID NO 42
<211> LENGTH: 8
<212> TYPE: PRT
<213> ORGANISM: Vaccinia virus

<400> SEQUENCE: 42

Thr Ser Tyr Lys Phe Glu Ser Val
1               5
```

-continued

<210> SEQ ID NO 43
<211> LENGTH: 10
<212> TYPE: PRT
<213> ORGANISM: Mus musculus

<400> SEQUENCE: 43

Ser Gly Pro Gln His Gln Lys Gln Gln Leu
1               5                   10

<210> SEQ ID NO 44
<211> LENGTH: 9
<212> TYPE: PRT
<213> ORGANISM: Mus musculus

<400> SEQUENCE: 44

Leu Pro Gly Lys Val Ile Met Asp Leu
1               5

<210> SEQ ID NO 45
<211> LENGTH: 9
<212> TYPE: PRT
<213> ORGANISM: Mus musculus

<400> SEQUENCE: 45

Ala Tyr Gln Glu Ile Lys Gln Ala Leu
1               5

<210> SEQ ID NO 46
<211> LENGTH: 9
<212> TYPE: PRT
<213> ORGANISM: Mus musculus

<400> SEQUENCE: 46

Gln Phe Val Lys Lys Gln Phe Asn Phe
1               5

<210> SEQ ID NO 47
<211> LENGTH: 8
<212> TYPE: PRT
<213> ORGANISM: Mus musculus

<400> SEQUENCE: 47

Ser Thr Leu Thr Tyr Ser Arg Met
1               5

<210> SEQ ID NO 48
<211> LENGTH: 8
<212> TYPE: PRT
<213> ORGANISM: Mus musculus

<400> SEQUENCE: 48

Ser Met Tyr Val Pro Gly Lys Leu
1               5

<210> SEQ ID NO 49
<211> LENGTH: 9
<212> TYPE: PRT
<213> ORGANISM: Mus musculus

<400> SEQUENCE: 49

Val Ala Ala Ala Asn Arg Glu Val Leu
1               5

<210> SEQ ID NO 50
<211> LENGTH: 9

```
<212> TYPE: PRT
<213> ORGANISM: Mus musculus

<400> SEQUENCE: 50

Asn Ser Met Val Leu Phe Asp His Val
1               5

<210> SEQ ID NO 51
<211> LENGTH: 9
<212> TYPE: PRT
<213> ORGANISM: Homo sapiens

<400> SEQUENCE: 51

Lys Thr Asn Ala Ile Ile Ser Leu Lys
1               5

<210> SEQ ID NO 52
<211> LENGTH: 10
<212> TYPE: PRT
<213> ORGANISM: Homo sapiens

<400> SEQUENCE: 52

His Gln Met Glu Leu Ala Met Pro Lys Lys
1               5                   10

<210> SEQ ID NO 53
<211> LENGTH: 9
<212> TYPE: PRT
<213> ORGANISM: Homo sapiens

<400> SEQUENCE: 53

Val Ala Ser Pro Val Thr Leu Gly Lys
1               5

<210> SEQ ID NO 54
<211> LENGTH: 10
<212> TYPE: PRT
<213> ORGANISM: Homo sapiens

<400> SEQUENCE: 54

Ser Val Ala Ser Pro Val Thr Leu Gly Lys
1               5                   10

<210> SEQ ID NO 55
<211> LENGTH: 9
<212> TYPE: PRT
<213> ORGANISM: Homo sapiens

<400> SEQUENCE: 55

Ser Ser Ala Leu Pro Gln Leu Pro Lys
1               5

<210> SEQ ID NO 56
<211> LENGTH: 9
<212> TYPE: PRT
<213> ORGANISM: Homo sapiens

<400> SEQUENCE: 56

Thr Leu Ala Gln Ser Val Ser Asn Lys
1               5

<210> SEQ ID NO 57
<211> LENGTH: 10
<212> TYPE: PRT
<213> ORGANISM: Homo sapiens
```

<400> SEQUENCE: 57

Tyr Met Ile Met Val Lys Cys Trp Met Ile
1               5                   10

<210> SEQ ID NO 58
<211> LENGTH: 10
<212> TYPE: PRT
<213> ORGANISM: Homo sapiens

<400> SEQUENCE: 58

Tyr Leu Val Pro Gln Gln Gly Phe Phe Cys
1               5                   10

<210> SEQ ID NO 59
<211> LENGTH: 9
<212> TYPE: PRT
<213> ORGANISM: Homo sapiens

<400> SEQUENCE: 59

Val Leu Arg Glu Asn Thr Ser Pro Lys
1               5

<210> SEQ ID NO 60
<211> LENGTH: 9
<212> TYPE: PRT
<213> ORGANISM: Homo sapiens

<400> SEQUENCE: 60

Val Val Leu Gly Val Val Phe Gly Ile
1               5

<210> SEQ ID NO 61
<211> LENGTH: 9
<212> TYPE: PRT
<213> ORGANISM: Homo sapiens

<400> SEQUENCE: 61

Arg Leu Leu Gln Glu Thr Glu Leu Val
1               5

<210> SEQ ID NO 62
<211> LENGTH: 9
<212> TYPE: PRT
<213> ORGANISM: Homo sapiens

<400> SEQUENCE: 62

Pro Leu Gln Pro Glu Gln Leu Gln Val
1               5

<210> SEQ ID NO 63
<211> LENGTH: 9
<212> TYPE: PRT
<213> ORGANISM: Homo sapiens

<400> SEQUENCE: 63

Leu Leu Gly Arg Asn Ser Phe Glu Val
1               5

<210> SEQ ID NO 64
<211> LENGTH: 9
<212> TYPE: PRT
<213> ORGANISM: Homo sapiens

<400> SEQUENCE: 64

```
Ile Leu His Asn Gly Ala Tyr Ser Leu
1               5

<210> SEQ ID NO 65
<211> LENGTH: 9
<212> TYPE: PRT
<213> ORGANISM: Homo sapiens

<400> SEQUENCE: 65

Thr Leu Glu Glu Ile Thr Gly Tyr Leu
1               5

<210> SEQ ID NO 66
<211> LENGTH: 9
<212> TYPE: PRT
<213> ORGANISM: Homo sapiens

<400> SEQUENCE: 66

Pro Leu Thr Ser Ile Ile Ser Ala Val
1               5

<210> SEQ ID NO 67
<211> LENGTH: 9
<212> TYPE: PRT
<213> ORGANISM: Homo sapiens

<400> SEQUENCE: 67

Lys Ile Phe Gly Ser Leu Ala Phe Leu
1               5

<210> SEQ ID NO 68
<211> LENGTH: 9
<212> TYPE: PRT
<213> ORGANISM: Homo sapiens

<400> SEQUENCE: 68

Ile Ile Ser Ala Val Val Gly Ile Leu
1               5

<210> SEQ ID NO 69
<211> LENGTH: 9
<212> TYPE: PRT
<213> ORGANISM: Homo sapiens

<400> SEQUENCE: 69

Ala Leu Ile His His Asn Thr His Leu
1               5

<210> SEQ ID NO 70
<211> LENGTH: 9
<212> TYPE: PRT
<213> ORGANISM: Homo sapiens

<400> SEQUENCE: 70

Ser Arg Phe Gly Gly Ala Val Val Arg
1               5

<210> SEQ ID NO 71
<211> LENGTH: 9
<212> TYPE: PRT
<213> ORGANISM: Homo sapiens

<400> SEQUENCE: 71

Ser Gln Lys Thr Tyr Gln Gly Ser Tyr
```

```
<210> SEQ ID NO 72
<211> LENGTH: 9
<212> TYPE: PRT
<213> ORGANISM: Homo sapiens

<400> SEQUENCE: 72

Leu Leu Gly Ala Thr Cys Met Phe Val
1               5

<210> SEQ ID NO 73
<211> LENGTH: 9
<212> TYPE: PRT
<213> ORGANISM: Homo sapiens

<400> SEQUENCE: 73

His Leu Tyr Gln Gly Cys Gln Val Val
1               5

<210> SEQ ID NO 74
<211> LENGTH: 9
<212> TYPE: PRT
<213> ORGANISM: Homo sapiens

<400> SEQUENCE: 74

Thr Tyr Leu Pro Thr Asn Ala Ser Leu
1               5

<210> SEQ ID NO 75
<211> LENGTH: 9
<212> TYPE: PRT
<213> ORGANISM: Homo sapiens

<400> SEQUENCE: 75

Ser Thr Ala Pro Pro Val His Asn Val
1               5

<210> SEQ ID NO 76
<211> LENGTH: 9
<212> TYPE: PRT
<213> ORGANISM: Homo sapiens

<400> SEQUENCE: 76

Ala Leu Cys Arg Trp Gly Leu Leu Leu
1               5

<210> SEQ ID NO 77
<211> LENGTH: 9
<212> TYPE: PRT
<213> ORGANISM: Homo sapiens

<400> SEQUENCE: 77

Leu Leu Leu Leu Thr Val Leu Thr Val
1               5

<210> SEQ ID NO 78
<211> LENGTH: 10
<212> TYPE: PRT
<213> ORGANISM: Homo sapiens

<400> SEQUENCE: 78

Glu Leu Thr Leu Gly Glu Phe Leu Lys Leu
1               5                   10
```

```
<210> SEQ ID NO 79
<211> LENGTH: 9
<212> TYPE: PRT
<213> ORGANISM: Homo sapiens

<400> SEQUENCE: 79

Arg Met Pro Glu Ala Ala Pro Pro Val
1               5

<210> SEQ ID NO 80
<211> LENGTH: 9
<212> TYPE: PRT
<213> ORGANISM: Homo sapiens

<400> SEQUENCE: 80

Arg Leu Val Asp Asp Phe Leu Leu Val
1               5
```

PROTEOGENOMIC-BASED METHOD FOR IDENTIFYING TUMOR-SPECIFIC ANTIGENS

CROSS REFERENCE TO RELATED APPLICATIONS

The present application is a § 371 national phase of International Application No. PCT/CA2019/051186, filed on Aug. 28, 2019, which claims the benefits of U.S. provisional patent application No. 62/724,760 filed Aug. 30, 2018, which applications are incorporated herein by reference in their entireties.

TECHNICAL FIELD

The present invention generally relates to cancer, and more specifically to the identification of tumor antigens useful for T-cell-based cancer immunotherapy.

BACKGROUND ART

CD8 T cells are known to be essential players in tumor eradication as the presence of tumor-infiltrating lymphocytes (TILs) in several cancers positively correlates with a good prognosis and response to immune checkpoint inhibitors[1,2]. To eliminate tumor cells, CD8 T cells recognize tumor antigens, which are abnormal MHC I-associated peptides (MAPs) presented by tumor cells. As CD8 T cells recognize MHC I-associated peptides (MAPs), the most important unanswered question is the nature of MAPs recognized by CD8 TILs[3]. Knowing that the abundance of CD8 TILs correlates with the mutation load of tumors, the dominant paradigm holds that CD8 TILs recognize mutated tumor-specific antigens (mTSAs), commonly referred to as neoantigens[2,4,5]. The superior immunogenicity of mTSAs is ascribed to their selective expression on tumors which minimizes the risk of immune tolerances. Nonetheless, some TILs have been shown to recognize cancer-restricted non-mutated MAPs[7] that will be referred to as aberrantly expressed TSAs (aeTSAs). aeTSAs can derive from a variety of cis- or trans-acting genetic and epigenetic changes that lead to the transcription and translation of genomic sequences that are not expressed in normal cells, such as endogenous retroelements (EREs)[8-10].

Considerable efforts are being devoted to discovering actionable TSAs that can be used in therapeutic cancer vaccines. The most common strategy hinges on reverse immunology: i) exome sequencing is performed on tumor cells to identify mutations, and ii) MHC-binding prediction software tools are used to identify which mutated MAPs might be good MHC binders[11,12]. While reverse immunology can enrich for TSA candidates, at least 90% of these candidates are false positives[5,13] because available computational methods may predict MHC binding, but they cannot predict other steps involved in MAP processing[14,15]. To overcome this limitation, a few studies have included mass spectrometry (MS) analyses in their TSA discovery pipeline[16], thereby providing a rigorous molecular definition of several TSAs[17,18]. However, the yield of these approaches has been extremely meager: in melanoma, one of the most mutated tumor type, an average of 2 TSAs per individual tumors have been validated by MS[19], while only a handful of TSAs has been found for other cancer types[15]. The paucity of TSAs is puzzling because injection of TILs or immune checkpoint inhibitors would not cause tumor regression if tumors did not express immunogenic antigens[20]. It was surmised that approaches based on exonic mutations have failed to identify TSAs because they did not take into account two crucial elements. First, these approaches focus only on mTSAs and neglect aeTSAs, essentially because there is currently no method for high-throughput identification of aeTSAs. This represents a major shortcoming because, while mTSAs are private antigens, aeTSAs would be preferred targets for vaccine development since they can be shared by multiple tumors[7,9]. Second, focusing on the exome as the only source of TSAs is very restrictive. The exome (i.e., all protein-coding genes) represents only 2% of the human genome, while up to 75% of the genome can be transcribed and potentially translated[22].

There is thus a need for novel approaches for identifying tumor antigens that may be used for T-cell-based cancer immunotherapy.

Acute lymphoblastic leukemia (ALL) is a malignant transformation and proliferation of lymphoid progenitor cells in the bone marrow, blood and extramedullary sites. While 80% of ALL occurs in children, it represents a devastating disease when it occurs in adults. Within the United States, the incidence of ALL is estimated at 1.6 per 100 000 population. While dose-intensification strategies have led to a significant improvement in outcomes for pediatric patients, prognosis for the elderly remains very poor. Despite a high rate of response to induction chemotherapy, only 30-40% of adult patients with ALL will achieve long-term remission.

There is thus a need for novel approaches for the treatment of ALL.

Lung cancer, a highly invasive, rapidly metastasizing and prevalent cancer, is the top killer cancer in both men and women in the United States of America (USA). About 90% of lung cancer cases are caused by smoking and the use of tobacco products. However, other factors such as radon gas, asbestos, air pollution exposures, and chronic infections can contribute to lung carcinogenesis. In addition, multiple inherited and acquired mechanisms of susceptibility to lung cancer have been proposed. Lung cancer is divided into two broad histologic classes, which grow and spread differently: small-cell lung carcinomas (SCLC) and non-small cell lung carcinomas (NSCLC). Treatment options for lung cancer include surgery, radiation therapy, chemotherapy, and targeted therapy. Despite the improvements in diagnosis and therapy made during the past 25 years, the prognosis for patients with lung cancer is still unsatisfactory. The responses to current standard therapies are poor except for the most localized cancers.

There is thus a need for novel approaches for the treatment of lung cancer.

The present description refers to a number of documents, the content of which is herein incorporated by reference in their entirety.

SUMMARY OF THE INVENTION

The present disclosure provides the following items 1 to 75:
1. A method for identifying a tumor antigen candidate in a tumor cell sample, the method comprising:
(a) generating a tumor-specific proteome database by: (i) extracting a set of subsequences (k-mers) comprising at least 33 base pairs from tumor RNA-sequences; (ii) comparing the set of tumor subsequences of (i) to a set of corresponding control subsequences comprising at least 33 base pairs extracted from RNA-sequences from normal cells; (iii) extracting the tumor subsequences that are absent in the corresponding control subsequences, thereby obtaining tumor-specific subsequences; and (iv) in silico translating the tumor-specific subsequences, thereby obtaining the tumor-specific proteome database;
(b) generating a personalized tumor proteome database by: (i) comparing the tumor RNA-sequences to a reference genome sequence to identify single-base mutations in said tumor RNA-sequences; (ii) inserting the single-base mutations identified in (i) in the reference genome sequence, thereby creating a personalized tumor genome sequence; (iii) in silico translating the expressed protein-coding transcripts from said personalized tumor genome sequence, thereby obtaining the personalized tumor proteome database;
(c) comparing the sequences of major histocompatibility complex (MHC)-associated peptides (MAPs) from said tumor with the sequences of the tumor-specific proteome database of (a) and the personalized tumor proteome database of (b) to identify the MAPs; and
(d) identifying a tumor antigen candidate among the MAPs identified in (c), wherein a tumor antigen candidate is a peptide whose sequence and/or encoding sequence is overexpressed or overrepresented in tumor cells relative to normal cells.
2. The method of item 1, wherein the above-noted method further comprises (1) isolating and sequencing major histocompatibility complex (MHC)-associated peptides (MAPs) from the tumor cell sample, and/or (2) performing whole transcriptome sequencing on the tumor cell sample, to obtain the tumor RNA-sequences.
3. The method of item 2, wherein said isolating MAPs comprises (i) releasing said MAPs from said cell sample by mild acid treatment; and (ii) subjecting the released MAPs to chromatography.
4. The method of item 3, wherein said method further comprises filtering the released peptides with a size exclusion column prior to said chromatography.
5. The method of any one of items 1 to 4, wherein said subsequences comprises from 33 to 54 base pairs.
6. The method of any one of items 1 to 5, further comprising assembling overlapping tumor-specific subsequences into longer tumor subsequences (contigs).
7. The method of item 6, wherein said size exclusion column has a cut-off of about 3000 Da.
8. The method of any one of items 1 to 7, wherein said sequencing of MAPs comprises subjecting the isolated MAPs to mass spectrometry (MS) sequencing analysis.
9. The method of any one of items 1 to 8, wherein said method further comprises generating a personalized normal proteome database using corresponding normal cells.
10. The method of item 9, wherein said identifying in (d) comprises excluding said MAP if its sequence is detected in the normal personalized proteome database.
11. The method of any one of items 1 to 10, wherein the method further comprises generating 24- or 39-nucleotide k-mer databases from said tumor RNA-sequences and from RNA-sequences from normal cells to obtain a tumor k-mer database and a normal k-mer database; and comparing the tumor k-mer database and a normal k-mer database to 24- or 39-nucleotide k-mer derived from the MAP encoding sequence, wherein an overexpression or overrepresentation of the k-mer derived from the MAP encoding sequence in said tumor k-mer database relative to said normal k-mer database is indicative that the corresponding MAP is a tumor antigen candidate.
12. The method of item 11, wherein the k-mer derived from the MAP encoding sequence is overexpressed or overrepresented by at least 10-fold in said tumor k-mer database relative to said normal k-mer database.
13. The method of item 11 or 12, wherein the k-mer derived from the MAP encoding sequence is absent from said normal k-mer database.
14. The method of any one of items 1 to 13, wherein said method comprises:
(a) isolating and sequencing MAPs in a tumor cell sample;
(b) performing whole transcriptome sequencing on said tumor cell sample, thereby obtaining tumor RNA-sequences;
(c) generating a tumor-specific proteome database by: (i) extracting a set of subsequences comprising at least 33 nucleotides from said tumor RNA-sequences; (ii) comparing the set of tumor subsequences of (i) to a set of corresponding control subsequences comprising at least 33 nucleotides extracted from RNA-sequences from normal cells; (iii) extracting the tumor subsequences that are absent, or underexpressed by at least 4-fold, in the corresponding control subsequences, thereby obtaining tumor-specific subsequences; and (iv) in silico translating the tumor-specific subsequences, thereby obtaining the tumor-specific proteome database;
(d) generating a personalized tumor proteome database by: (i) comparing the tumor RNA-sequences to a reference genome sequence to identify single-base mutations in said tumor RNA-sequences; (ii) inserting the single-base mutations identified in (i) in the reference genome sequence, thereby creating a personalized tumor genome sequence; (iii) in silico translating the expressed protein-coding transcripts from said personalized tumor genome sequence, thereby obtaining the personalized tumor proteome database;
(e) generating a personalized normal proteome database by: (i) comparing RNA-sequences from normal cells to a reference genome sequence to identify single-base mutations in said normal RNA-sequences; (ii) inserting the single-base mutations identified in (i) in the reference genome sequence, thereby creating a personalized normal genome sequence; (iii) in silico translating the expressed protein-coding transcripts from said personalized normal genome sequence, thereby obtaining the personalized normal proteome database;
(f) generating a normal and a tumor k-mer database by (i) extracting a set of subsequences comprising at least 24 nucleotides from said RNA-sequences from normal cells and said tumor RNA-sequences;
(g) comparing the sequences of the MAPs obtained in (a) with the sequences of the tumor-specific proteome database of (c) and the personalized tumor proteome database of (d) to identify the MAPs; and
(h) identifying a tumor antigen candidate among the MAPs identified in (f), wherein a tumor antigen candidate corresponds to a MAP (1) whose sequence is not present in the personalized normal proteome database; and (2) (i) whose sequence is present in the personalized tumor proteome database; and/or (ii) whose encoding sequence is overexpressed or overrepresented in said tumor k-mer database relative to said normal k-mer database.
15. The method of any one of items 1 to 14, wherein said method further comprises selecting MAPs having a length of 8 to 11 amino acids.
16. The method of any one of items 1 to 15, wherein said normal cells are thymic cells.
17. The method of item 16, wherein said thymic cells are medullary thymic epithelial cells (mTEC).

18. The method of any one of items 1 to 17, further comprising comparing the coding sequence of said tumor antigen candidate to sequences from normal tissues.
19. The method of any one of items 1 to 18, wherein said MAPs have a length of 8 to 11 amino acids.
20. The method of any one of items 1 to 19, further comprising assessing the binding of the tumor antigen candidate to an MHC molecule.
21. The method of item 20, wherein said binding is assessed using an MHC binding prediction algorithm.
22. The method of any one of items 1 to 21, further comprising assessing the frequency of T cells recognizing the tumor antigen candidate in a cell population.
23. The method of item 22, wherein the frequency of T cells recognizing the tumor antigen candidate is assessed using multimeric MHC class I molecules comprising said tumor antigen candidate in their peptide binding groove.
24. The method of any one of items 1 to 23, further comprising assessing the ability of the tumor antigen candidate to induce T cell activation.
25. The method of item 24, wherein the ability of the tumor antigen candidate to induce T cell activation is assessed by measuring cytokine production by T cells contacted with cells having said tumor antigen candidate bound to MHC class I molecules at their cell surface.
26. The method of item 25, wherein said cytokine production comprises interferon-gamma (IFN-γ) production.
27. The method of any one of items 1 to 26, further comprising assessing the ability of said tumor antigen candidate to induce T-cell-mediated tumor cell killing and/or to inhibit tumor growth.
28. A tumor antigen peptide identified by the method defined in any one of items 1 to 27.
29. A tumor antigen peptide comprising or consisting of one of the amino acid sequences set forth in any one of SEQ ID NOs: 1-39.
30. The tumor antigen peptide of item 29, comprising or consisting of one of the amino acid sequences set forth in any one of SEQ ID NOs: 17-39.
31. The tumor antigen peptide of item 30, wherein said tumor antigen peptide is a leukemia tumor antigen peptide and comprises or consists of one of the amino acid sequences set forth in any one of SEQ ID NOs: 17-28.
32. The tumor antigen peptide of item 31, wherein said leukemia is B-cell acute lymphoblastic leukemia (B-ALL).
33. The tumor antigen peptide of item 31 or 32, wherein said tumor antigen peptide binds to a human leukocyte antigen (HLA) of the HLA-A*02:01 allele and comprises or consists of one of the amino acid sequences set forth in any one of SEQ ID NOs: 17-19, 27 and 28.
34. The tumor antigen peptide of item 31 or 32, wherein said tumor antigen peptide binds to a human leukocyte antigen (HLA) of the HLA-B*40:01 allele and comprises or consists of the amino acid sequence set forth in SEQ ID NO: 20.
35. The tumor antigen peptide of item 31 or 32, wherein said tumor antigen peptide binds to a human leukocyte antigen (HLA) of the HLA-A*11:01 allele and comprises or consists of one of the amino acid sequences set forth in any one of SEQ ID NOs: 21-23.
36. The tumor antigen peptide of item 31 or 32, wherein said tumor antigen peptide binds to a human leukocyte antigen (HLA) of the HLA-B*08:01 allele and comprises or consists the amino acid sequences set forth in SEQ ID NO: 24 or 25.
37. The tumor antigen peptide of item 31 or 32, wherein said tumor antigen peptide binds to a human leukocyte antigen (HLA) of the HLA-B*07:02 allele and comprises or consists of the amino acid sequence set forth in SEQ ID NO: 26.
38. The tumor antigen peptide of item 30, wherein said tumor antigen peptide is a lung tumor antigen peptide and comprises or consists of one of the amino acid sequences set forth in any one of SEQ ID NOs: 29-39.
39. The tumor antigen peptide of item 38, wherein said lung tumor is a non-small cell lung cancer (NSCLC).
40. The tumor antigen peptide of item 38 or 39, wherein said tumor antigen peptide binds to a human leukocyte antigen (HLA) of the HLA-A*11:01 allele and comprises or consists of one of the amino acid sequences set forth in any one of SEQ ID NOs: 29-35.
41. The tumor antigen peptide of item 38 or 39, wherein said tumor antigen peptide binds to a human leukocyte antigen (HLA) of the HLA-B*07:02 allele and comprises or consists of the amino acid sequence set forth in SEQ ID NO: 36.
42. The tumor antigen peptide of item 38 or 39, wherein said tumor antigen peptide binds to a human leukocyte antigen (HLA) of the HLA-A*24:02 allele and comprises or consists the amino acid sequences set forth in SEQ ID NO: 38 or 39.
43. The tumor antigen peptide of item 38 or 39, wherein said tumor antigen peptide binds to a human leukocyte antigen (HLA) of the HLA-C*07:01 allele and comprises or consists of the amino acid sequence set forth in SEQ ID NO: 37.
44. The tumor antigen of any one of items 29-43, which is derived from a non-protein coding region of the genome.
45. The tumor antigen of item 44, wherein said non-protein coding region of the genome is an intergenic region, an intronic region, a 5' untranslated region (5' UTR), a 3' untranslated region (3' UTR), or an endogenous retroelement (ERE).
46. A nucleic acid encoding the tumor antigen peptide of any one of items 28-45.
47. The nucleic acid of item 46, which is an mRNA or a viral vector.
48. A liposome comprising the tumor antigen peptide of any one of items 28-45 or the nucleic acid of item 46 or 47.
49. A composition comprising the tumor antigen peptide of any one of items 28-45, the nucleic acid of item 46 or 47, or the liposome of item 48, and a pharmaceutically acceptable carrier.
50. A vaccine comprising the tumor antigen peptide of any one of items 28-45, the nucleic acid of item 46 or 47, the liposome of item 48, or the composition of item 49, and an adjuvant.
51. An isolated major histocompatibility complex (MHC) class I molecule comprising the tumor antigen peptide of any one of items 28-45 in its peptide binding groove.
52. The isolated MHC class I molecule of item 51, which is in the form of a multimer.
53. The isolated MHC class I molecule of item 52, wherein said multimer is a tetramer.
54. An isolated cell comprising the tumor antigen peptide of any one of items 28-45.
55. An isolated cell expressing at its surface major histocompatibility complex (MHC) class I molecules comprising the tumor antigen peptide of any one of items 28-45 in their peptide binding groove.
56. The cell of item 55, which is an antigen-presenting cell (APC).
57. The cell of item 56, wherein said APC is a dendritic cell.
58. A T-cell receptor (TCR) that specifically recognizes the isolated MHC class I molecule of any one of items 51-53 and/or MHC class I molecules expressed at the surface of the cell of any one of items 54-57.
59. An isolated CD8+T lymphocyte expressing at its cell surface the TCR of item 58.

60. A cell population comprising at least 0.5% of CD8+T lymphocytes as defined in item 59.

61. A method of treating cancer in a subject comprising administering to the subject an effective amount of: (i) the tumor antigen peptide of any one of items 28-45; (ii) the nucleic acid of item 46 or 47; (iii) the liposome of item 48; (iv) the composition of item 49; (v) the vaccine of item 50; (vi) the cell of any one of items 54-57; (vii) the CD8+T lymphocytes of item 59; or (viii) the cell population of item 60.

62. The method of item 61, wherein said cancer is leukemia.

63. The method of item 62, wherein said leukemia is B-cell acute lymphoblastic leukemia (B-ALL).

64. The method of item 61, wherein said cancer is lung cancer.

65. The method of item 64, wherein said lung tumor is a non-small cell lung cancer (NSCLC).

66. The method of any one of items 61-65, further comprising administering at least one additional antitumor agent or therapy to the subject.

67. The method of item 66, wherein said at least one additional antitumor agent or therapy is a chemotherapeutic agent, immunotherapy, an immune checkpoint inhibitor, radiotherapy or surgery.

68. Use of: (i) the tumor antigen peptide of any one of items 28-45; (ii) the nucleic acid of item 46 or 47; (iii) the liposome of item 48; (iv) the composition of item 49; (v) the vaccine of item 50; (vi) the cell of any one of items 54-57; (vii) the CD8+T lymphocytes of item 59; or (viii) the cell population of item 60, for treating cancer in a subject.

69. Use of: (i) the tumor antigen peptide of any one of items 28-45; (ii) the nucleic acid of item 46 or 47; (iii) the liposome of item 48; (iv) the composition of item 49; (v) the vaccine of item 50; (vi) the cell of any one of items 54-57; (vii) the CD8+T lymphocytes of item 59; or (viii) the cell population of item 60, for the manufacture of a medicament for treating cancer in a subject.

70. The use of item 68 or 69, wherein said cancer is leukemia.

71. The use of item 70, wherein said leukemia is B-cell acute lymphoblastic leukemia (B-ALL).

72. The use of item 68 or 69, wherein said cancer is lung cancer.

73. The use of item 72, wherein said lung tumor is a non-small cell lung cancer (NSCLC).

74. The use of any one of items 68-73, further comprising the use of at least one additional antitumor agent or therapy.

75. The use of item 74, wherein said at least one additional antitumor agent or therapy is a chemotherapeutic agent, immunotherapy, an immune checkpoint inhibitor, radiotherapy or surgery.

Other objects, advantages and features of the present invention will become more apparent upon reading of the following non-restrictive description of specific embodiments thereof, given by way of example only with reference to the accompanying drawings.

BRIEF DESCRIPTION OF DRAWINGS

In the appended drawings:

FIGS. 1A, B: Schematic detailing how the canonical cancer proteome (FIG. 1A) and cancer-specific proteome (FIG. 1B) were built for each analyzed sample. FIG. 1C: The combination of those two proteomes, termed the global cancer database, was then used to identify MAPs, and more specifically TSAs, sequenced by liquid chromatography-MS/MS (LC-MS/MS) from two well-characterized murine cell lines, namely CT26 and EL4, and seven human primary samples, namely four B-ALLs and three lung tumor biopsies (n=2-4 per sample). Statistics regarding each part of the global cancer database can be found in Tables 4a-b, while implementation details to build the cancer-specific proteome by k-mer profiling are presented in FIG. 7. aa: amino acids, nts: nucleotides, the sample-specific threshold on k-mer occurrence (see section k-mer filtering and generation of cancer-specific proteomes of Example 1 below).

FIG. 2A: Flowcharts indicating the key validation steps involved in TSA discovery. Details concerning each step can be found in FIG. 8. FIG. 2B: Most TSA candidates derive from aberrantly expressed sequences. Barplot showing the number of mTSAs (m) and aeTSA candidates (ae) in the CT26 and EL4 tumor models. FIG. 2C: Heatmap showing the expression of MCS for aeTSA candidates in 22 tissues/organs for which RNA-Seq data are publicly available (see Table 5). Expression of MCS for previously reported overexpressed EL4 TAAs[40,41] is displayed as a control. Expression values were normalized to rphm (reads per hundred million reads sequenced, see section Peripheral expression of MCS of Example 1 for details) and averaged across all RNA-Seq experiments available for each tissue. Bold squares indicate tissues where the relevant MCS was detected at >0 rphm. Adip. tissue: adipose tissue, mam. gland: mammary gland and s.c. adip. tissue: subcutaneous adipose tissue. SGPQHQKQQL=SEQ ID NO:43, LPGKVIMDL=SEQ ID NO:44, AYQEIKQAL=SEQ ID NO:45, QFVKKQFNF=SEQ ID NO:46, MPHSLLPLVTF= SEQ ID NO:6, SPSYVYHQF=SEQ ID NO:10, SPHQVFNL=SEQ ID NO:9, GYQKMKALL=SEQ ID NO:1, SGPPYYKGI, SEQ ID NO: 8, LPQELPGLVVL= SEQ ID NO:5, SSPRGSSTL=SEQ ID NO:13, ATQQFQQL=SEQ ID NO:11, VNYLHRNV=SEQ ID NO: 15, TVPLNHNTL=SEQ ID NO:14, IILEFHSL=SEQ ID NO:12, STLTYSRM=SEQ ID NO:47, SMYVPGKL=SEQ ID NO:48, VAAANREVL=SEQ ID NO:49, NSMVLFDHV=SEQ ID NO:50. FIG. 2D: Most ae/mTSAs derive from non-coding regions. Barplots depicting the number of TSAs derived from in-frame translation of coding exons (coding—in), out-of-frame translation of coding exons (coding—out) and translation of allegedly non-coding regions (non-coding). Numbers inside bars represent the numbers of aeTSA/mTSA. Percentages above bars indicate the proportion of TSAs derived from atypical translation events, i.e., TSAs belonging to the coding—out and non-coding categories. Features of CT26 and EL4 TSAs can be found in Tables 1a and b, respectively.

(FIG. 3A) two aeTSAs, (FIG. 3B) two ERE TSAs (one aeTSA or one mTSA) and (FIG. 3C) one mTSA. Mice were injected i.v. with 5×10⁵ live EL4 cells (black triangles) on day 0 and all surviving mice were rechallenged on day 150. Control groups were immunized with unpulsed DCs (black line). X̃ represents the median survival. Statistical significance of immunized vs. control groups was calculated using a log-rank test, where ns stands for not significant (p>0.05). 10 mice per group for peptide-specific immunization, 19 mice for control group. IILEFHSL=SEQ ID NO:12,

TVPLNHNTL=SEQ ID NO:14, VNYL/IHRNV=SEQ ID NO:15, VTPVYQHL=SEQ ID NO:16.

Figure 4A:
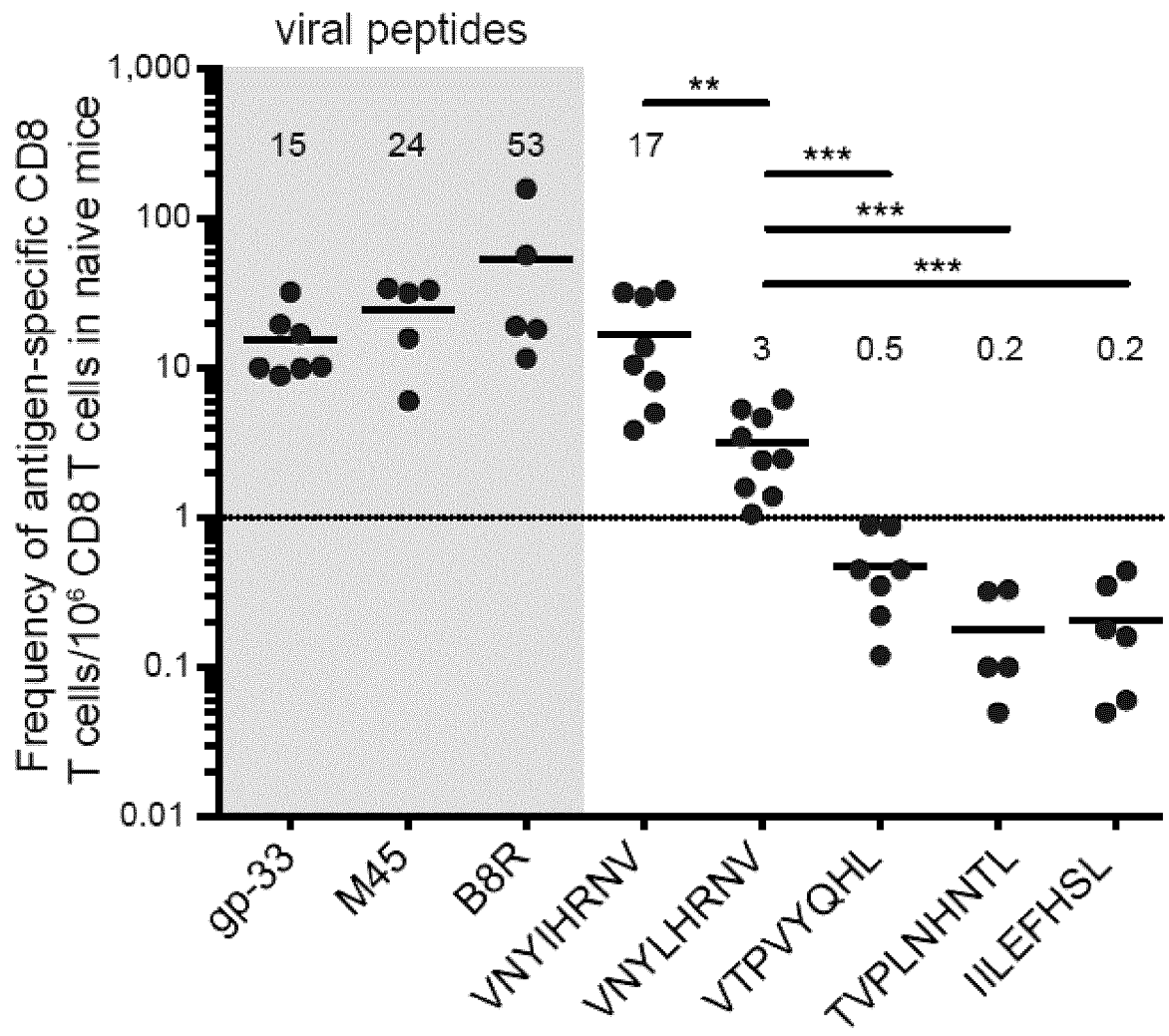
Figure 4B:
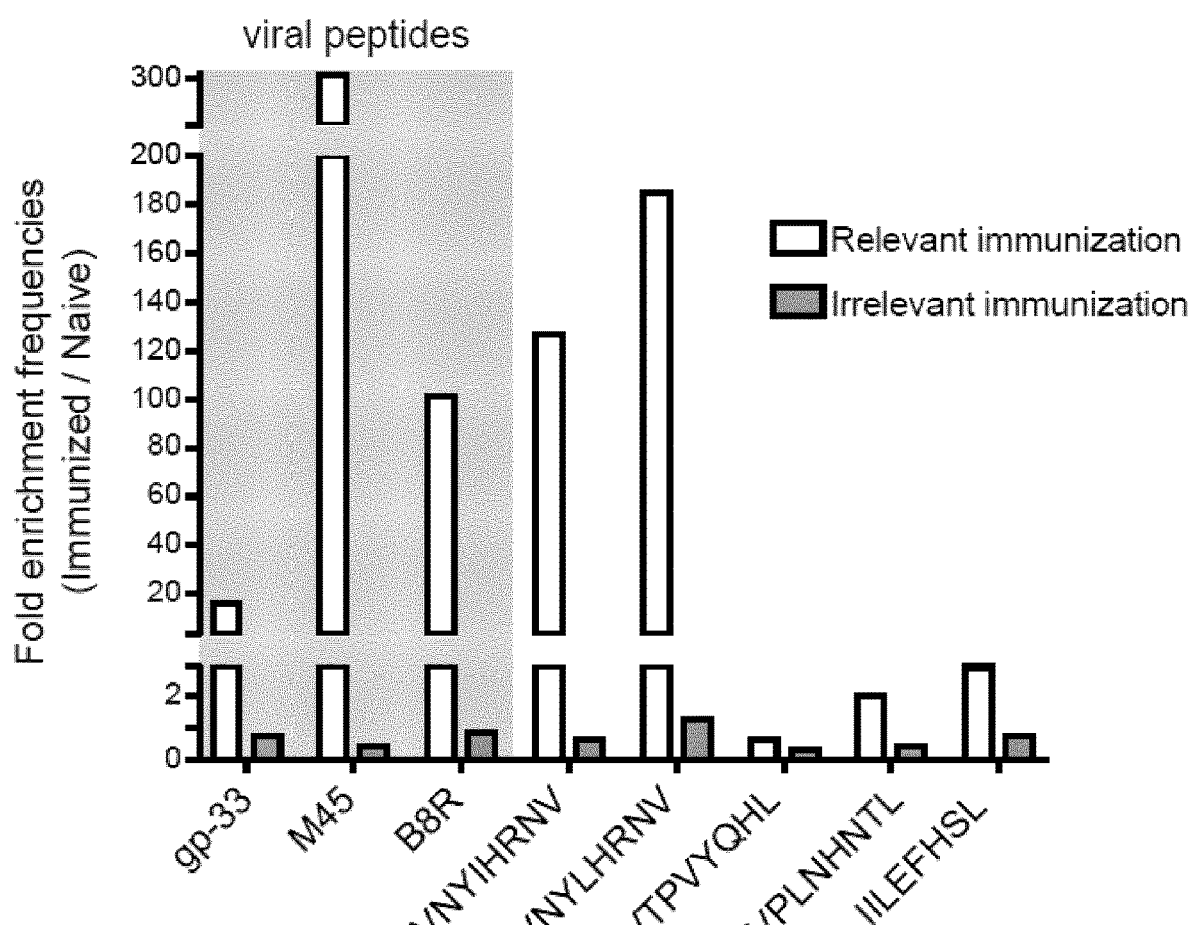

FIGS. 4A-D are graphs showing the frequency of and IFN-γ secretion by TSA-specific T cells in naive and immunized mice. FIG. 4A: Number of tetramer$^+$CD8$^+$ T cells per $10^6$ CD8$^+$ T cells in naive mice. Each circle represents one mouse (n=5 to 9 mice). Dotted line represents a frequency of 1 tetramer$^+$ T cell per $10^6$ CD8$^+$ T cells. p-values were calculated using two-tailed Mann-Whitney tests (; p<0.01 and *; p<0.001). FIG. 4B: Expansion of antigen-specific CD8$^+$ T cells after immunization. Fold enrichment for tetramer$^+$CD8$^+$ T cells was calculated by dividing the mean frequency in mice immunized with relevant (white bars) or irrelevant (gray bars) peptides by the mean frequency in naive mice. FIGS. 4C, 4D: Sorted CD8$^+$ T cells from immunized mice were incubated for 48 hours in the presence of irradiated peptide-pulsed splenocytes. FIG. 4C: the frequency of IFN-γ secreting antigen-specific cells is expressed as the mean frequency of spot-forming cells (SFC reported per $10^6$ CD8 T cells plated) in immunized mice minus that in naive mice. Three independent experiments with circles representing technical replicates. p-values were calculated using unpaired two-tailed Student's t-tests, all p<0.05 (range: 0.0025-0.0143). FIG. 4D: Functional avidity of antigen-specific T cells was calculated by normalizing the frequency of SFC to maximum value and by calculating an $EC_{50}$ for each peptide using a dose-response curve. Functional avidity values for H7$^a$ and H13$^a$ were previously published and used for comparative purposes. Three independent experiments. On all relevant panels, full horizontal lines and numbers above each condition represent the mean values. Viral peptides used as control are highlighted in gray. IILEFHSL=SEQ ID NO:12, TVPLNHNTL=SEQ ID NO:14, VNYL/IHRNV=SEQ ID NO:15, VTPVYQHL=SEQ ID NO:16.

Figure 5C:
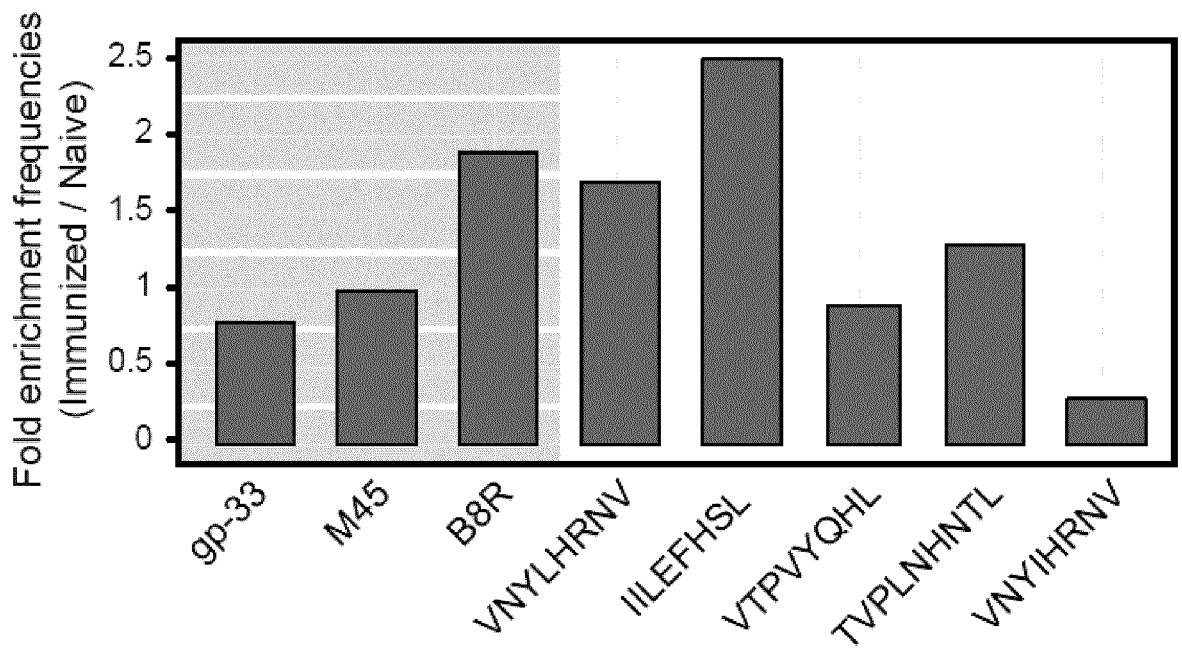
Figure 5D:
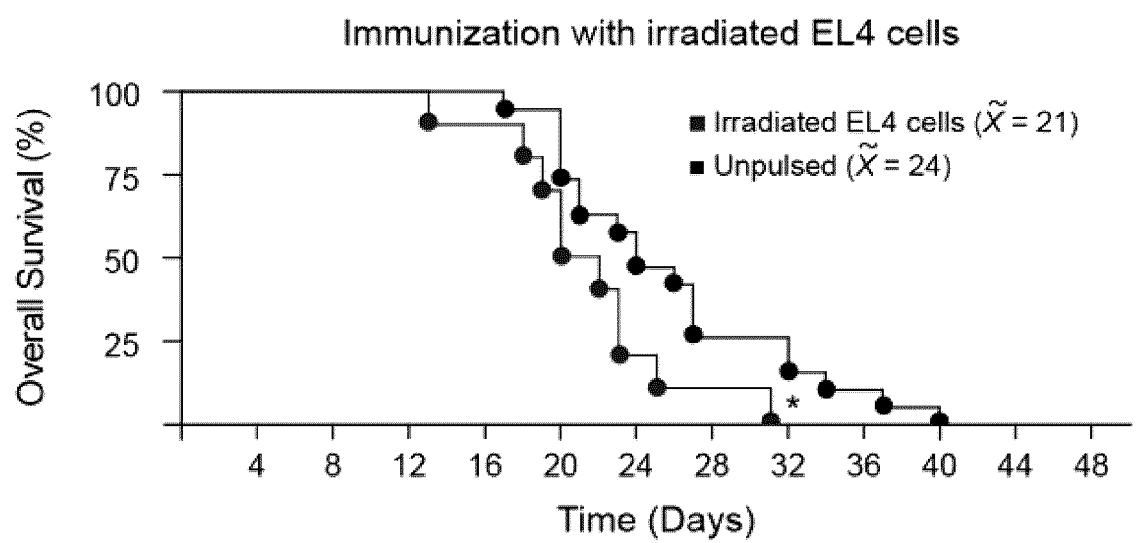

FIGS. 5A-D are graphs showing that high expression of EL4-derived TSAs is important but not sufficient to induce anti-leukemic responses. FIGS. 5A, B: Analysis of TSA expression at the RNA and the peptide level was performed on EL4 cells injected at day 0 or 150, respectively. FIG. 5A: Barplot representing the number of EL4 RNA-Seq reads fully overlapping the MCS encoding each of the five EL4 TSAs. FIG. 5B: TSA copy number per cell, as estimated by PRM MS using $^{13}$C-synthetic peptide analogs of the five EL4 TSAs. Three replicates of EL4 cells per TSA. Average number of TSA copy number per cell is indicated on the left-hand side of the graph. N.D.: not detected. FIG. 5C: Expansion of TSA-specific CD8$^+$ T cells after injection with live EL4 cells without prior immunization with peptide-pulsed DCs. Fold enrichment for tetramer$^+$CD8$^+$ T cells was calculated by dividing the mean frequency in EL4-injected mice by the mean frequency in naive mice. Fold enrichment for T cells recognizing viral peptides, which are not presented by EL4 cells, are shown as negative controls and are highlighted in gray. FIG. 5D: C57BL/6 female mice were immunized twice with irradiate 592 d (10,000 cGy) EL4 cells (blue line) or unpulsed DCs as control (black line) and then injected i.v. with 5×10$^5$ live EL4 cells. X̂ represents the median survival. 10 mice for irradiated EL4 cell immunization, 19 mice for control group. IILEFHSL=SEQ ID NO:12, TVPLNHNTL=SEQ ID NO:14, VNYL/IHRNV=SEQ ID NO:15, VTPVYQHL=SEQ ID NO:16.

Figure 6A:
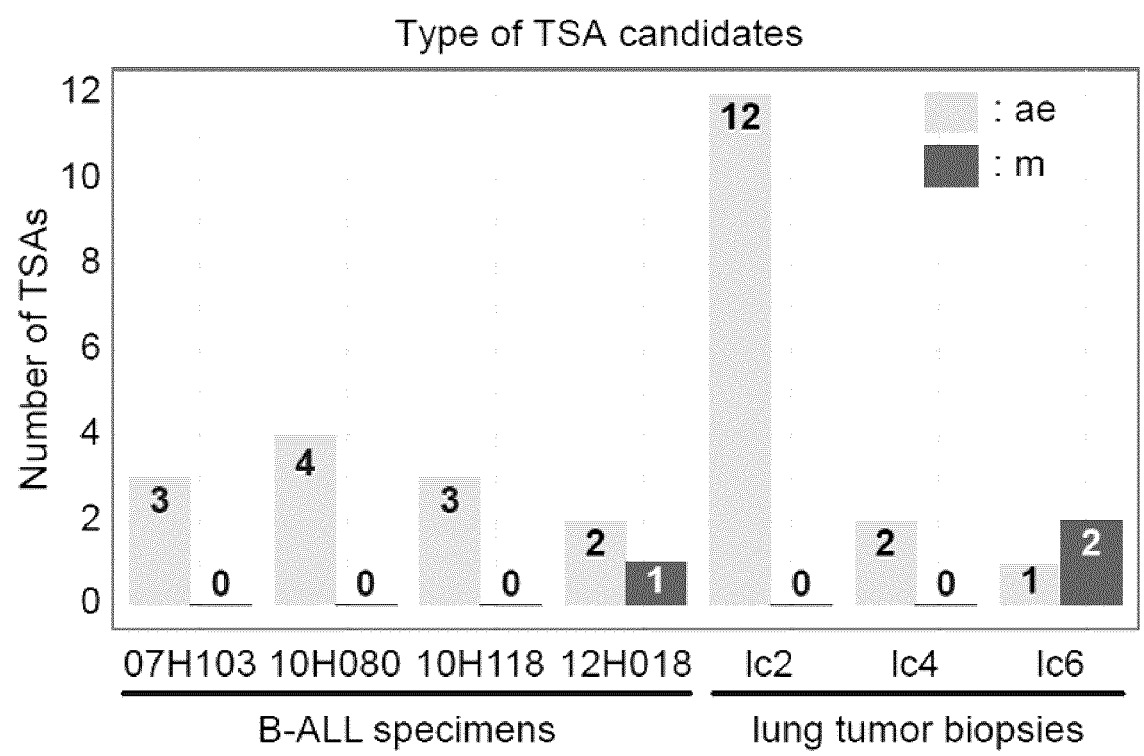
Figure 6B:
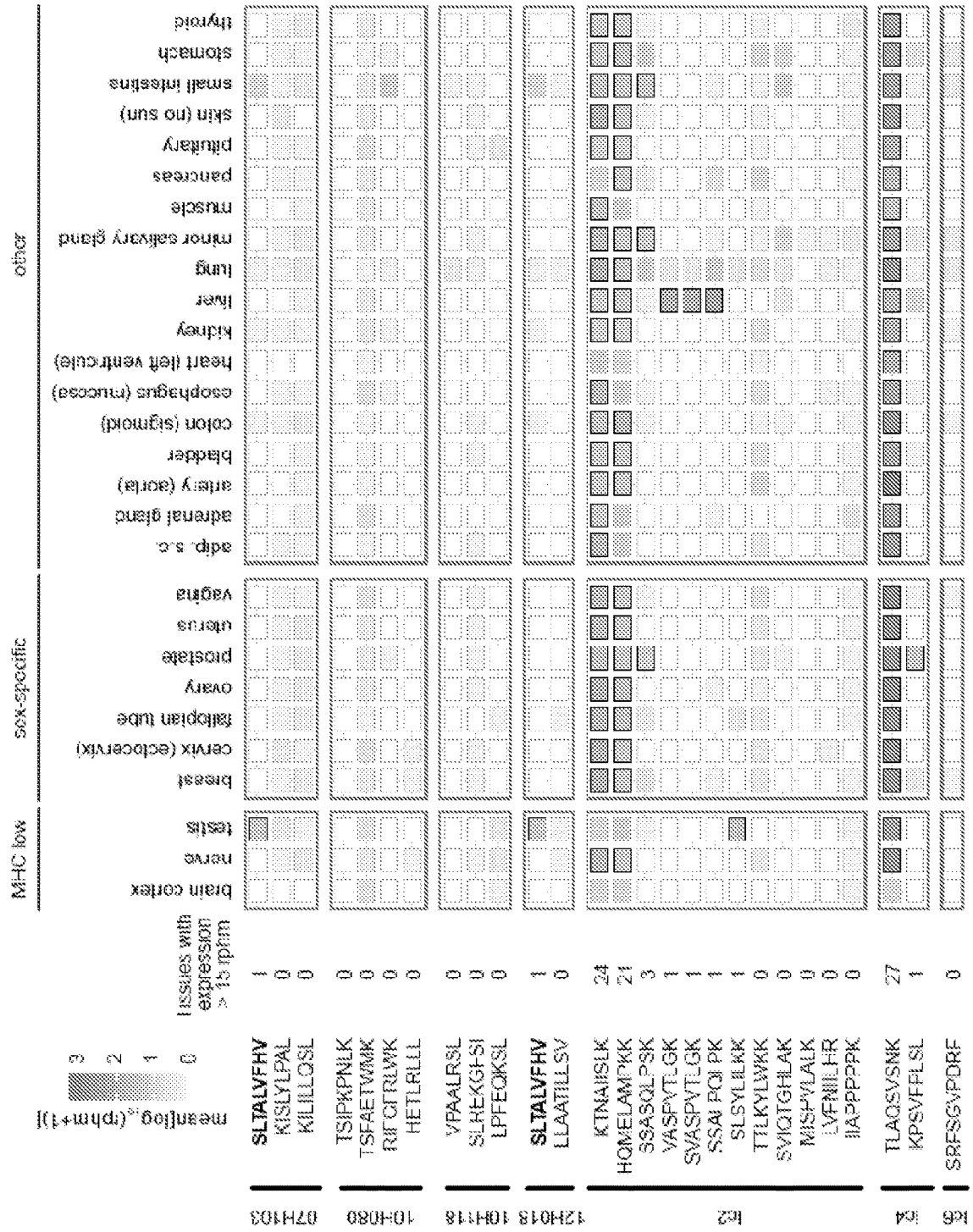
Figure 6B:
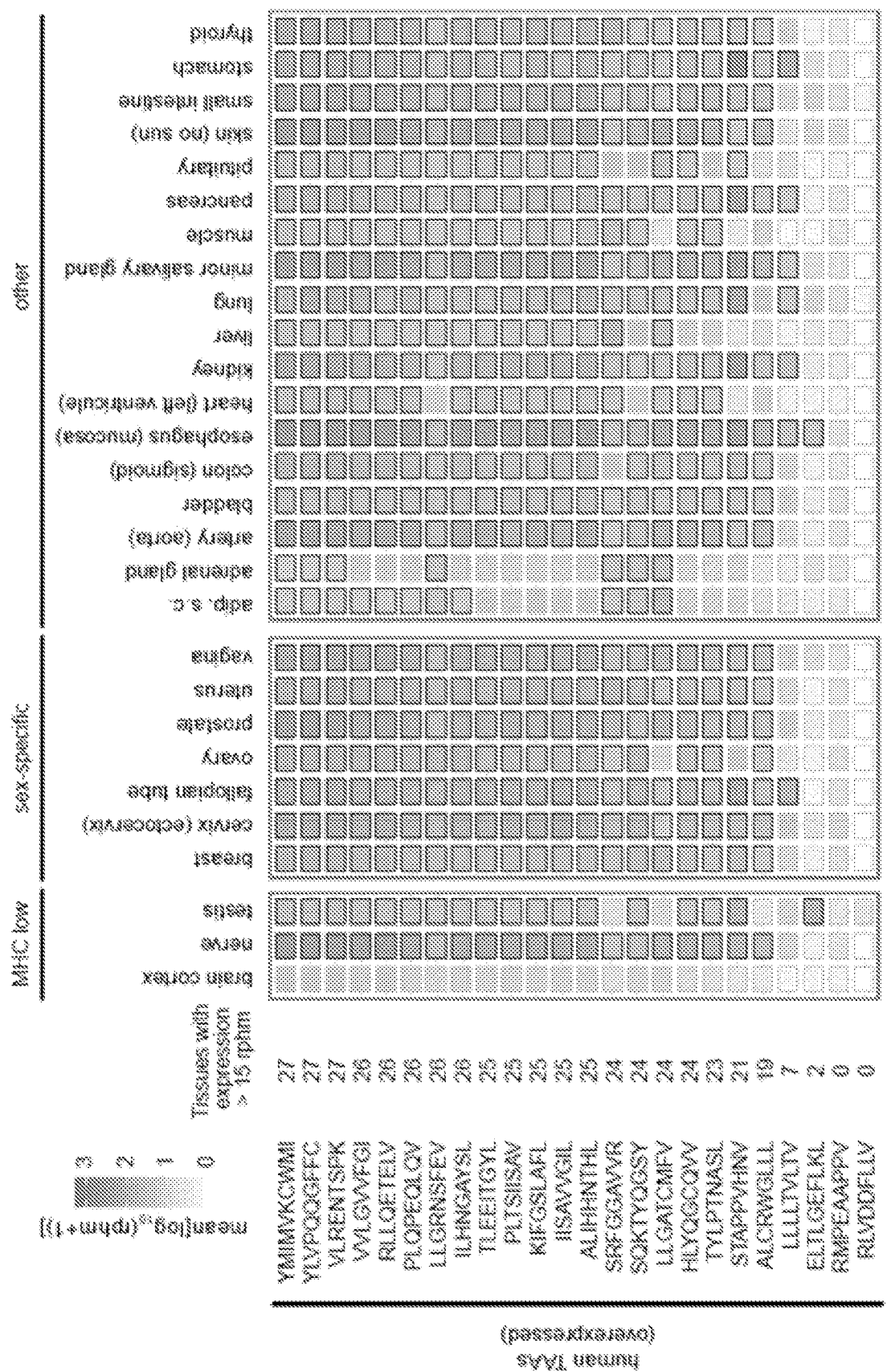
Figure 6C:
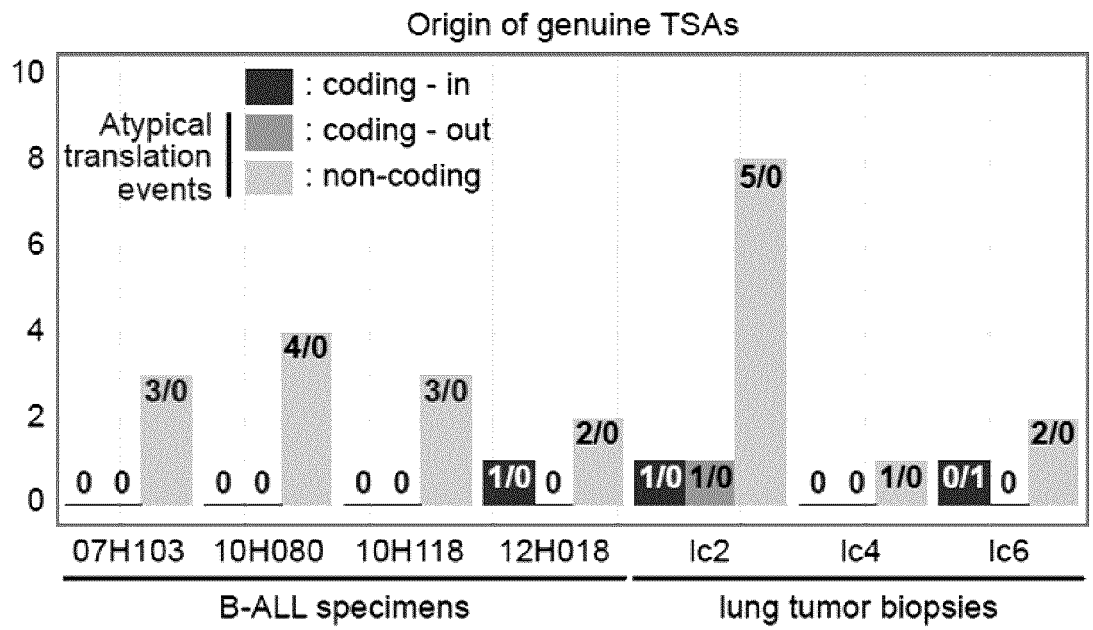

FIGS. 6A-C show that most TSAs detected in human primary tumors derive from the translation of non-coding regions. FIG. 6A: Most human TSAs are aeTSAs. Barplot showing the number of aeTSAs candidates (ae) and mTSAs (m) in each primary sample analyzed. FIG. 6B: Peripheral expression of human aeTSAs candidates and TAAs. Heatmap showing the expression of MCS for the 27 aeTSAs and 24 overexpressed TAAs, obtained from Cancer Immunity Peptide database[48], across a panel of 28 human tissues for which RNA-Seq data were publicly available (see Table 6). Expression values were normalized to rphm (see section Peripheral expression of MCS in Example 1 below for details) and averaged across all RNA-Seq experiments available for each tissue. For each antigen, the number of tissues in which its MCS is expressed at >15 rphm is shown to the left-hand side of the heatmap. Adip. s.c.: adipose subcutaneous. SLTALVFHV=SEQ ID NO:19, KISLYLPAL=SEQ ID NO:18, KILILLQSL=SEQ ID NO:17, TSIPKPNLK=SEQ ID NO:23, TSFAETWMK=SEQ ID NO:22, RIFGFRLWK=SEQ ID NO:21, HETLRLLL=SEQ ID NO:20, VPAALRSL=SEQ ID NO:26, SLREKGFSI=SEQ ID NO:25, LPFEQKSL=SEQ ID NO:24, LLAATILLSV=SEQ ID NO:27, KTNAIISLK=SEQ ID NO:51, HQMELAMPKK=SEQ ID NO:52, SSASQLPSK=SEQ ID NO:33, VASPVTLGK=SEQ ID NO:53, SVASPVTLGK=SEQ ID NO:54, SSALPQLPK=SEQ ID NO:55, SLSYLILKK=SEQ ID NO: 32, TTLKYLWKK=SEQ ID NO:35, SVIQTGHLAK=SEQ ID NO:34, MISPVLALK=SEQ ID NO:31, LVFNIILHR=SEQ ID NO: 30, IIAPPPPPK=SEQ ID NO:29, TLAQSVSNK=SEQ ID NO:56, KPSVFPLSL=SEQ ID NO:36, SRFSGVPDRF=SEQ ID NO:38, YMIMVKCWMI=SEQ ID NO:57, YLVPQQGFFC=SEQ ID NO:58, VLRENTSPK=SEQ ID NO:59, VVLGVVFGI=SEQ ID NO:60, RLLQETELV=SEQ ID NO:61, PLQPEQLQV=SEQ ID NO:62, LLGRNSFEV=SEQ ID NO:63, ILHNGAYSL=SEQ ID NO:64, TLEEITGYL=SEQ ID NO:65, PLTSIISAV=SEQ ID NO:66, KIFGSLAFL=SEQ ID NO:67, IISAVVGIL=SEQ ID NO:68, ALIHHNTHL=SEQ ID NO:69, SRFGGAVVR=SEQ ID NO:70, SQKTYQGSY=SEQ ID NO:71, LLGATCMFV=SEQ ID NO:72, HLYQGCQVV=SEQ ID NO:73, TYLPTNASL=SEQ ID NO:74, STAPPVHNV=SEQ ID NO:75, ALCRWGLLL=SEQ ID NO:76, LLLLTVLTV=SEQ ID NO:77, ELTLGEFLKL=SEQ ID NO:78, RMPEAAPPV=SEQ ID NO:79, RLVDDFLLV=SEQ ID NO:80. FIG. 6C: Most human TSAs derive from non-coding regions. Barplot depicting the number of human TSAs derived from in-frame translation of coding exons (coding—in), out-of-frame translation of coding exons (coding—out) and translation of allegedly non-coding regions (non-coding). Features of human TSAs identified in each sample can be found in Tables 2a-d and 3a-c.

Figures 7A, 7B:
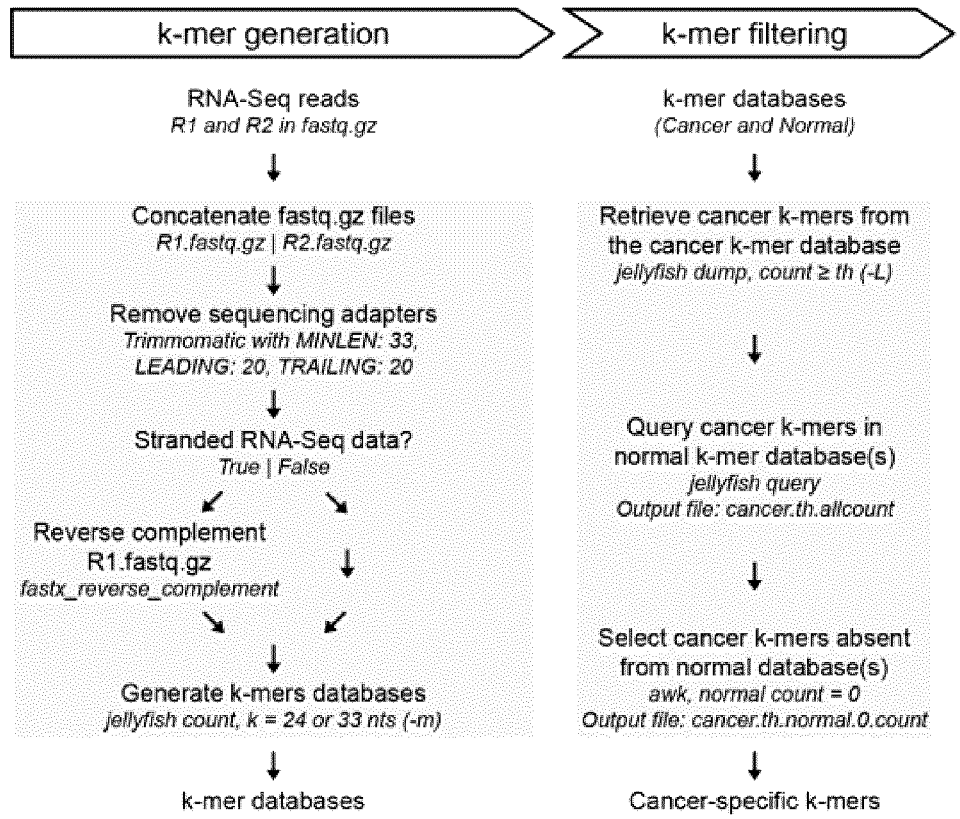

FIGS. 7A-D are schematics of the architecture of the codes used for the k-mer profiling workflow. Details pertaining to the codes used to generate k-mers from RNA-seq reads (FIG. 7A), filter k-mers (FIG. 7B), assemble k-mers into contigs (FIG. 7C) and translate contigs (FIG. 7D).

Figure 8A:
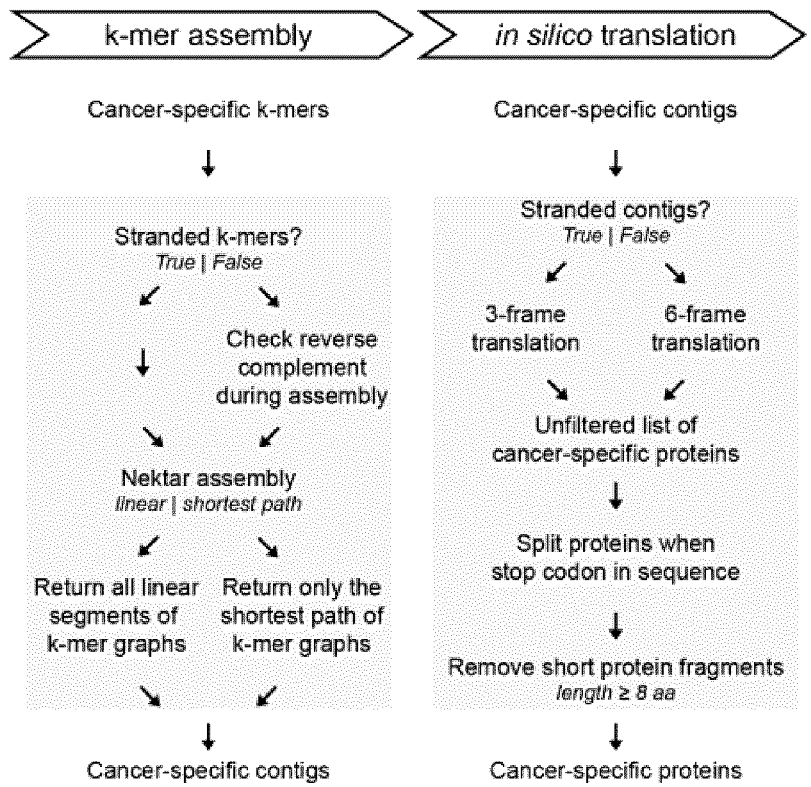
Figure 8A:
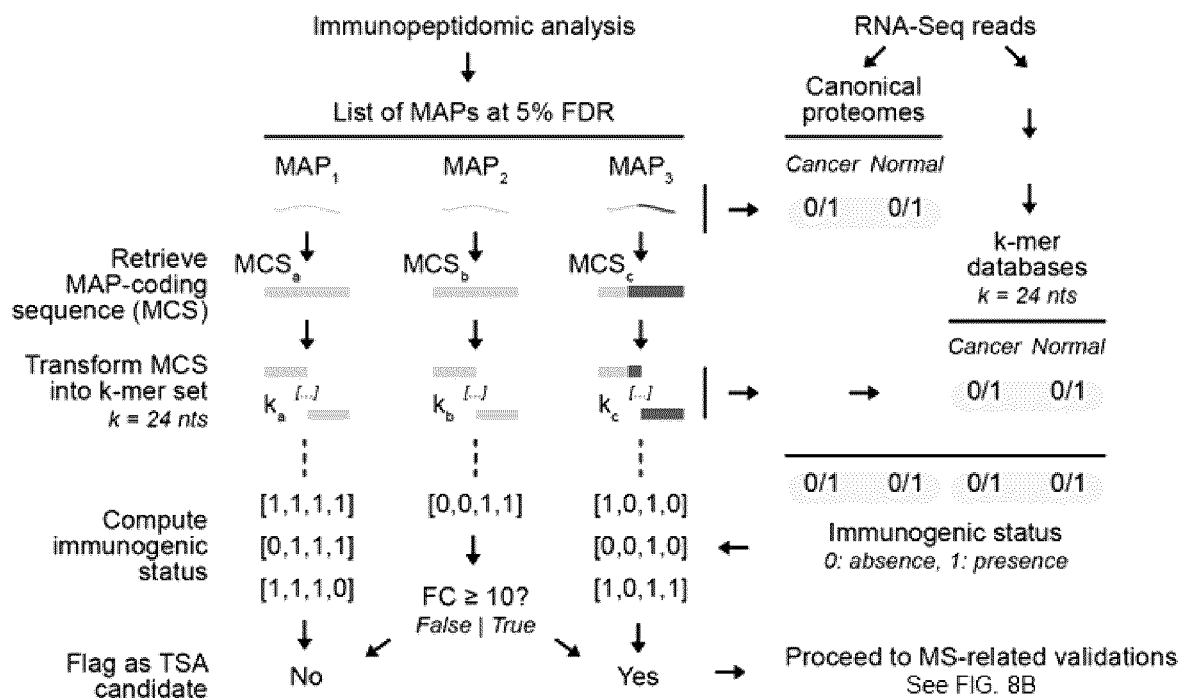
Figure 8B:
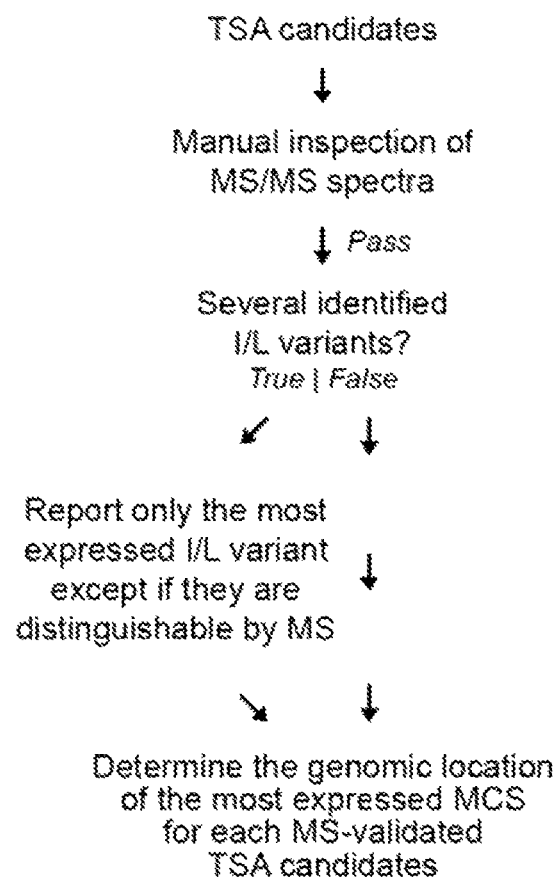
Figure 8C:

FIGS. 8A-C show the TSA validation process. FIG. 8A: Schematic detailing the computation of the immunogenic status for pairs of MAP/protein. FC: Tumor/syngeneic mTEC$^{hi}$ (murine samples) or TEC/mTEC (human samples). FIG. 8B: Strategy used to perform the MS-related validations of MAPs flagged as TSA candidates. FIG. 8C: Schematic summarizing the strategy used to assign a genomic location to MS-validated murine TSA candidates (CT26 and EL4) as well as MS-validated human TSA candidates for B-ALL specimens and lung cancers.

FIGS. 9A-D are graphs showing the detection of antigen-specific CD8$^+$ T cells in naive and pre-immunized mice.

Figure 9A:
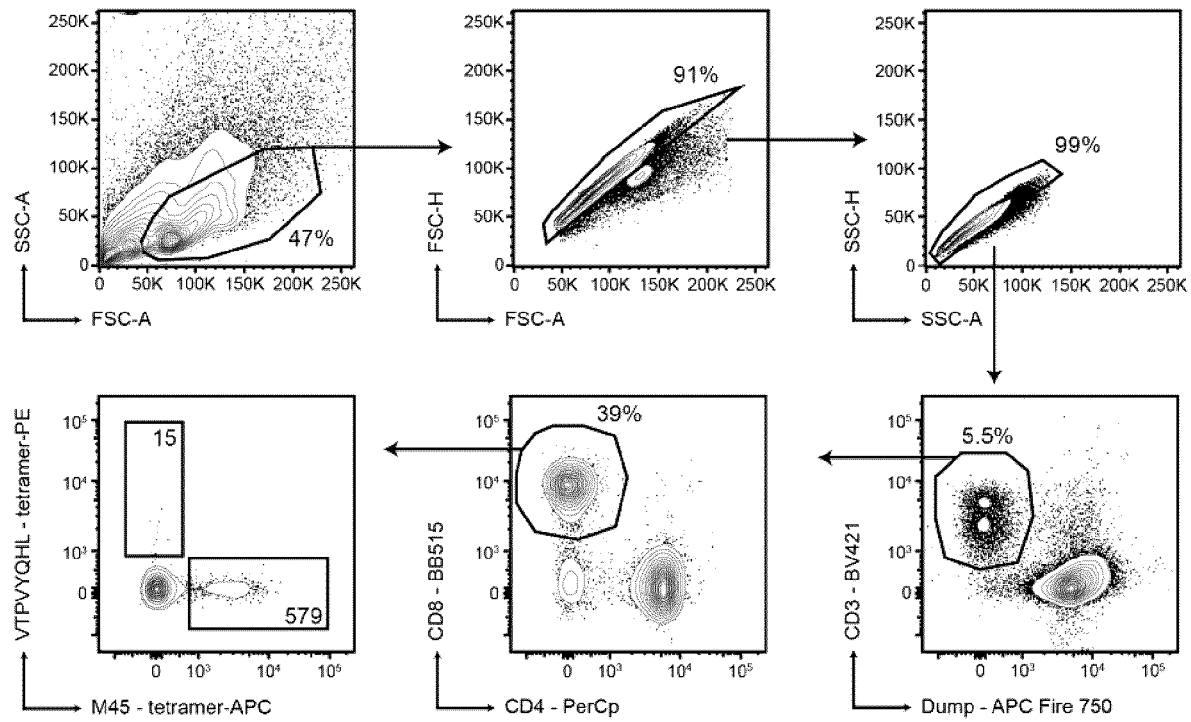
Figure 9B:
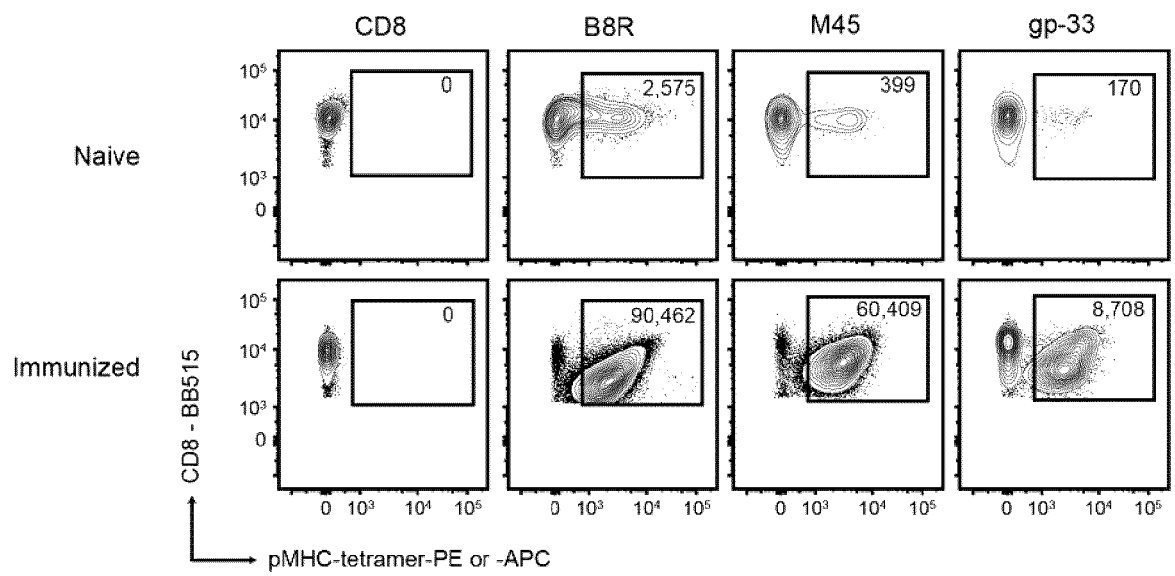
Figure 9C:
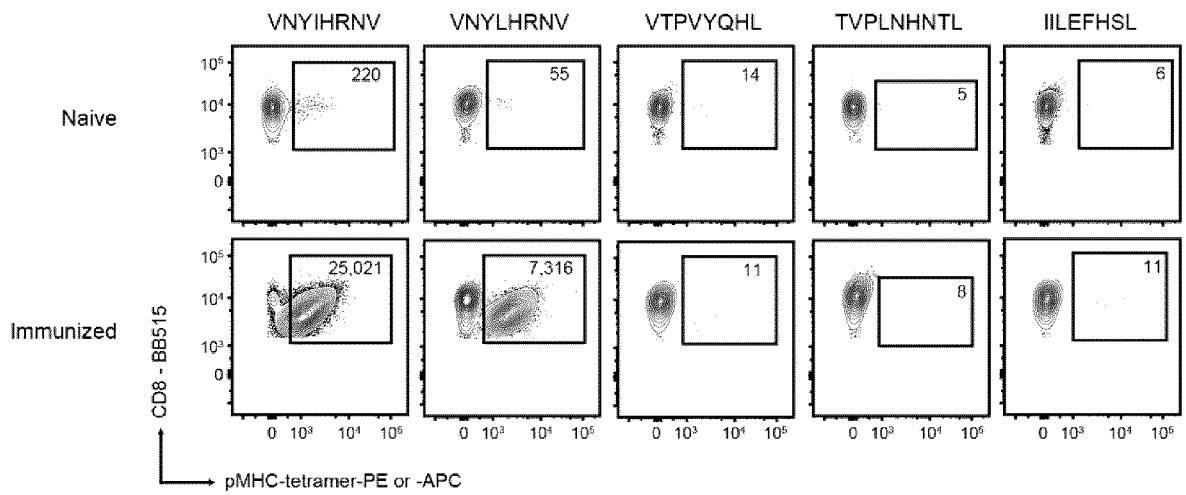
Figure 9D:
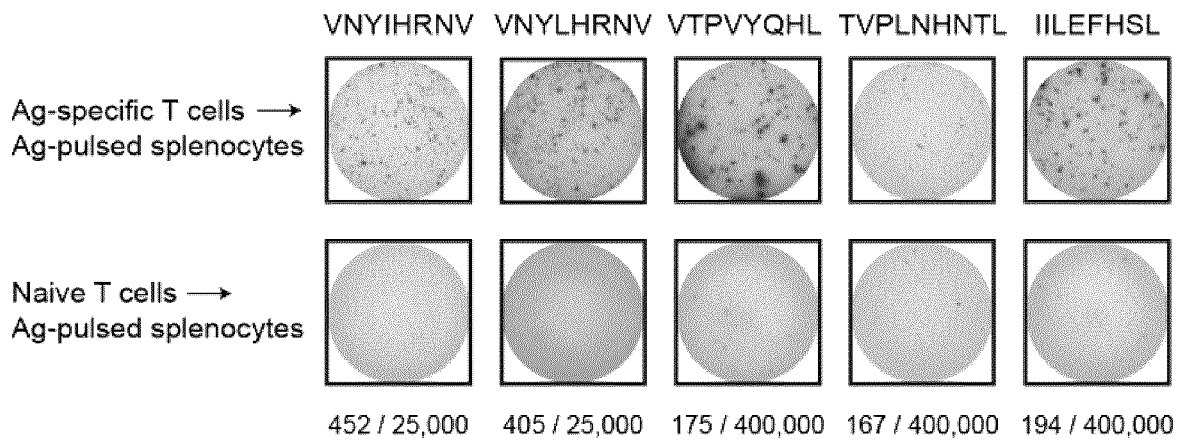

FIG. 9A: Gating strategy for the detection of pMHC tetramer+CD8+ T cells ex vivo. Tetramer enrichment were performed on single-cell suspensions isolated from the spleen and lymph nodes of each mice. After doublets exclusion, Dump−CD3+ cells were analyzed for CD8 and CD4 expression and pMHC I tetramer+ cells were analyzed in the CD8+ compartment. A representative staining obtained following VTPV/H-2K$^b$-PE and M45/H-2D$^b$-APC tetramers enrichment in a naive mouse is shown. Absolute numbers of tetramer+CD8+ T cells detected for each specificity are indicated. The Dump channel corresponds to pooled events positive for dead cells, CD45R and CD19, F4/80, CD11b, CD11c. FIGS. 9B, C: Representative analysis of CD44 expression on antigen-specific CD8 T cells in naive (upper row) and pre-immunized (lower row) mice. The CD44 status of CD8+ cells before magnetic enrichment (FIG. 9B, left panel) and after ex vivo enrichment for tetramer viral specificities (FIG. 9B) and TSA specificities (FIG. 9C) are represented. Percentages and number of CD44-positive or -negative cells are indicated. FIG. 9D: One representative experiment of the frequency of IFN-γ-secreting CD8+ T cells in immunized and naive mice. The number of spot forming units (SFUs) relative to the number of the number of plated CD8+ T cells in each condition are indicated below each well. IILEFHSL=SEQ ID NO:12, TVPLNHNTL=SEQ ID NO:14, VNYL/IHRNV=SEQ ID NO:15, VTPVYQHL=SEQ ID NO:16.

Figure 10A:
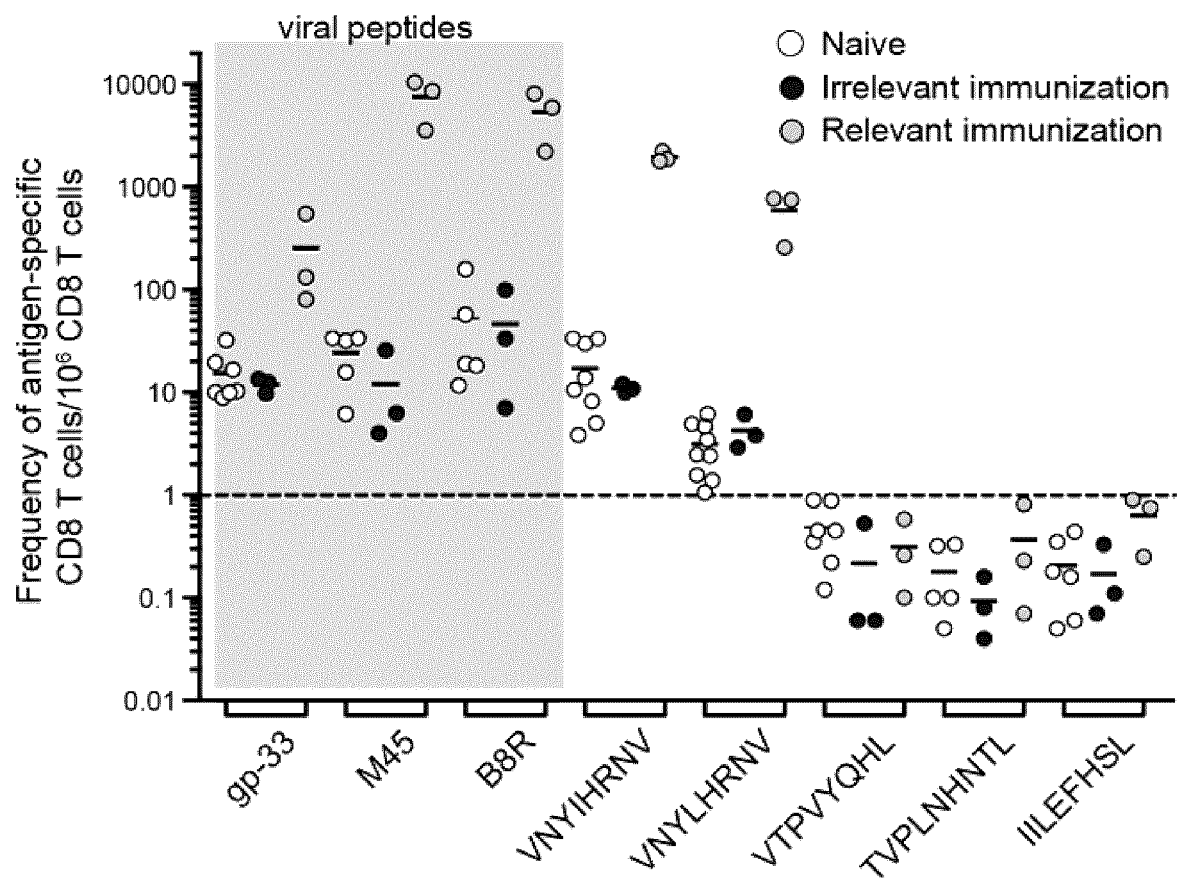
Figure 10B:
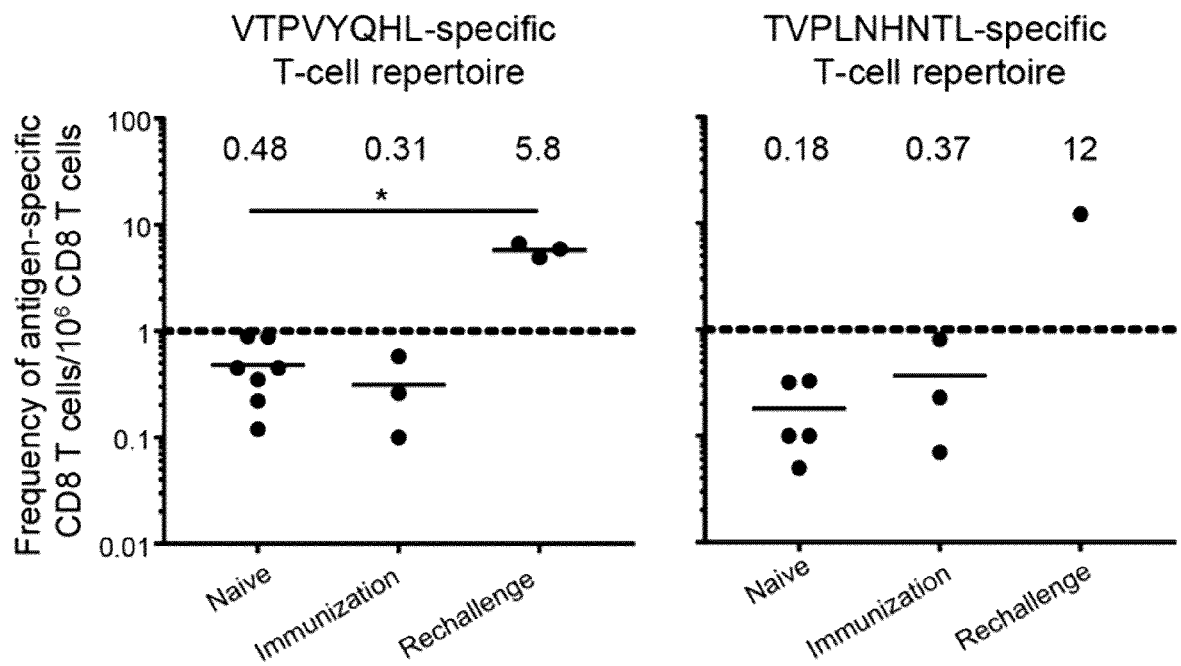
Figure 10C:
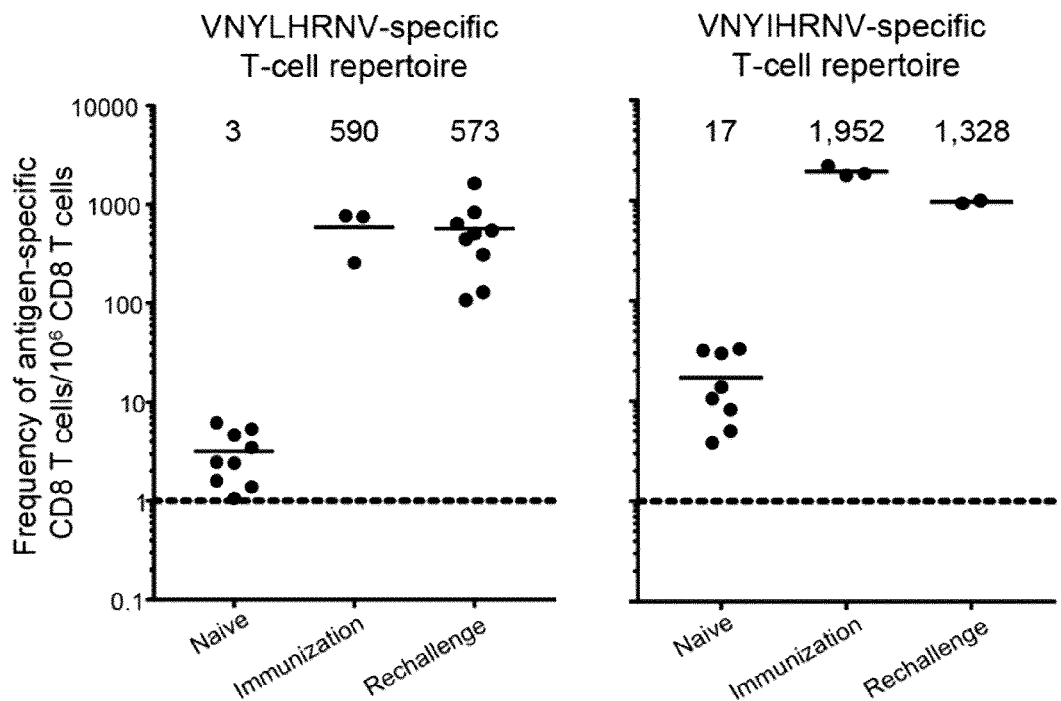
Figure 10D:
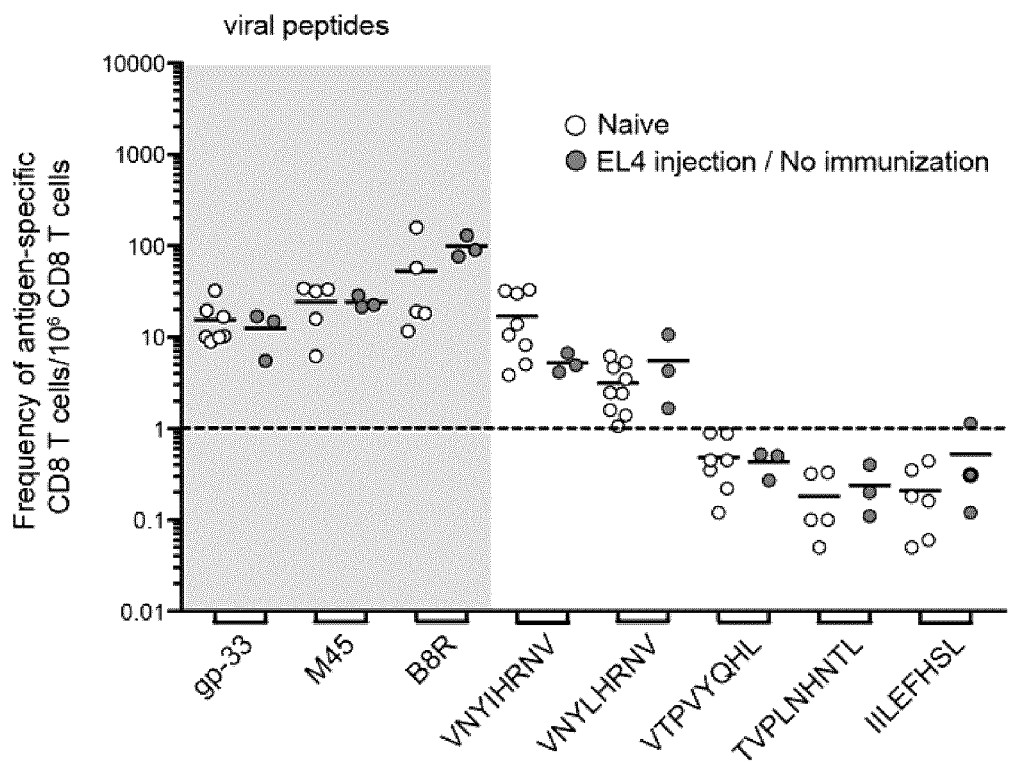

FIGS. 10A-D are graphs showing the frequencies of antigen-specific T cells. FIG. 10A: Frequencies of antigen-specific T cells in naive or mice immunized with relevant or irrelevant peptides. FIGS. 10B, C: Frequencies of antigen-specific CD8+ T cells in mice immunized against VTPVYQHL (SEQ ID NO:16) or TVPLNHNTL (SEQ ID NO:14) (FIG. 10B) or against VNYLHRNV (SEQ ID NO:15) or VNYIHRNV (SEQ ID NO:15) (FIG. 10C) that were rechallenged with EL4 cells at day 150. For comparison purposes, frequencies of antigen-specific T cells in naive and immunized mice reported in FIG. 10A are reproduced. FIG. 10D: Frequencies of antigen-specific T cells in non-immunized mice injected with EL4 cells. All calculated frequencies of tetramers+CD8+ T cells are expressed as the number of antigen-specific CD8+ T cells per $10^6$ CD8+ T cell. Each symbol represents one mouse (n=1 to 9 mice). Dotted line represents a minimal detection level of one tetramer T cell per $10^6$ CD8+ T cells. Viral peptides used as controls are highlighted in gray. p-values were calculated using two-tailed Mann-Whitney tests (*p≤0.05).

Figure 11A:
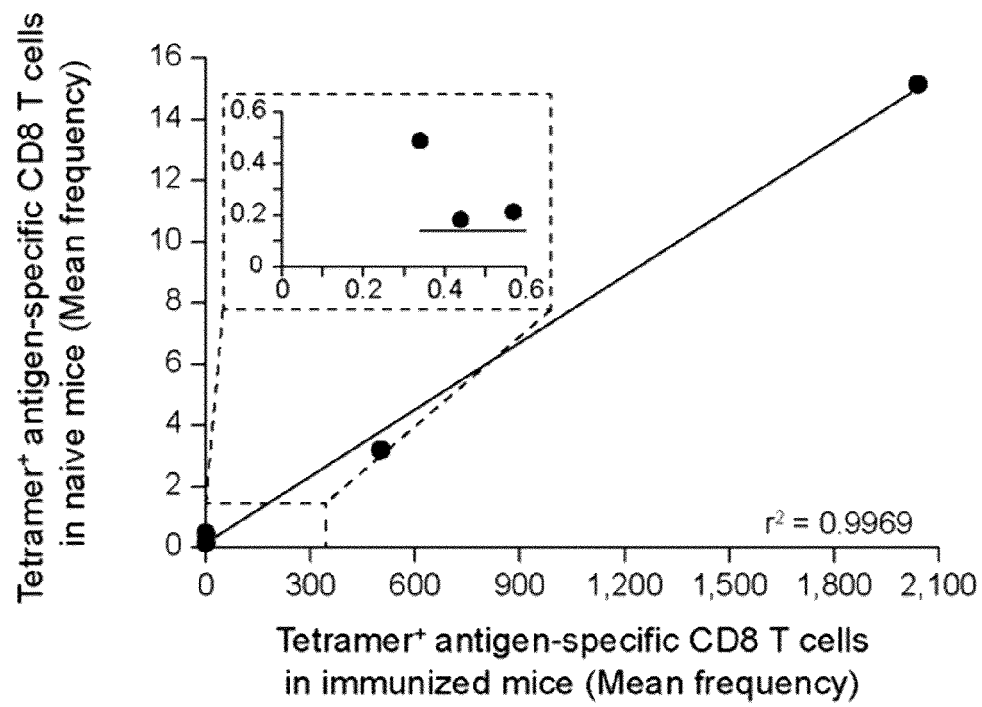
Figure 11B:
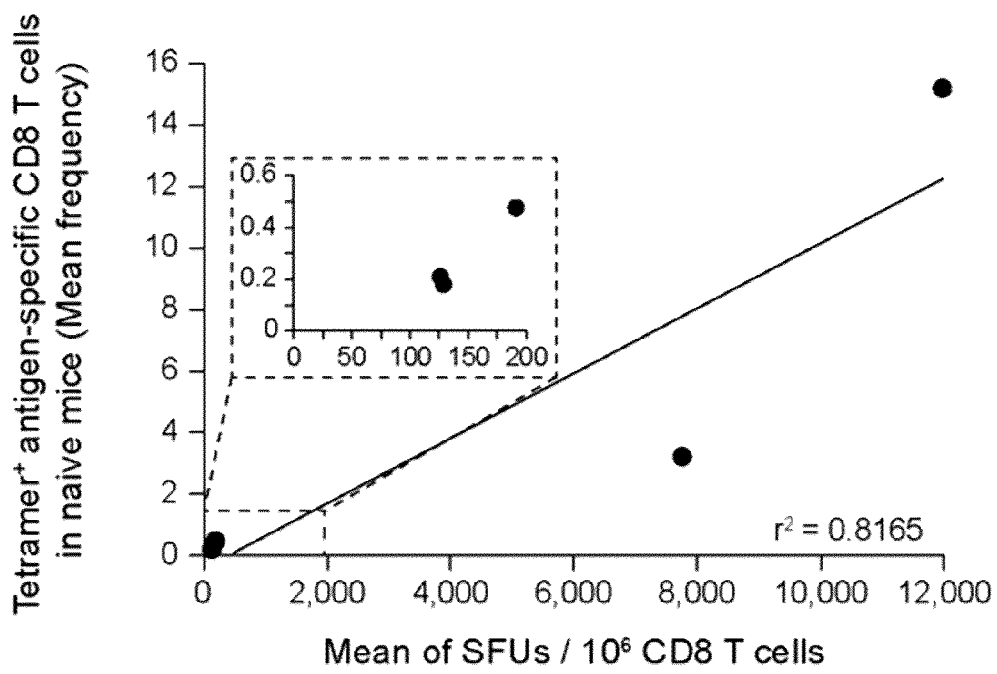
Figure 11C:
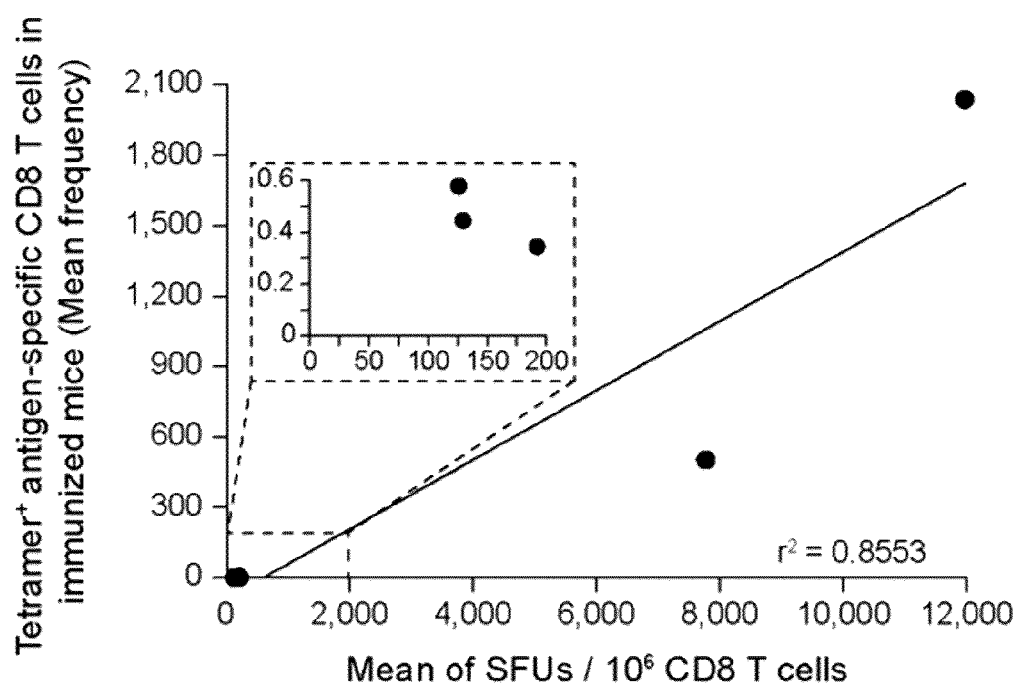

FIGS. 11A-C are graphs showing the correlation between antigen-specific T cell frequencies in naive and pre-immunized mice. Correlation between the frequencies of antigen-specific CD8+ T cells in the naive repertoire and in immunized mice as calculated by tetramer staining (FIG. 11A) and IFN-γ ELISpot assays (FIG. 11B). FIG. 11C: Correlation between the frequencies of antigen-specific CD8+ T cells in immunized mice as calculated by tetramer staining and IFN-γ ELISpot assays. Average frequencies were used for plotting data. Fitness of curves was determined by the coefficient of determination ($r^2$).

Figure 12A:
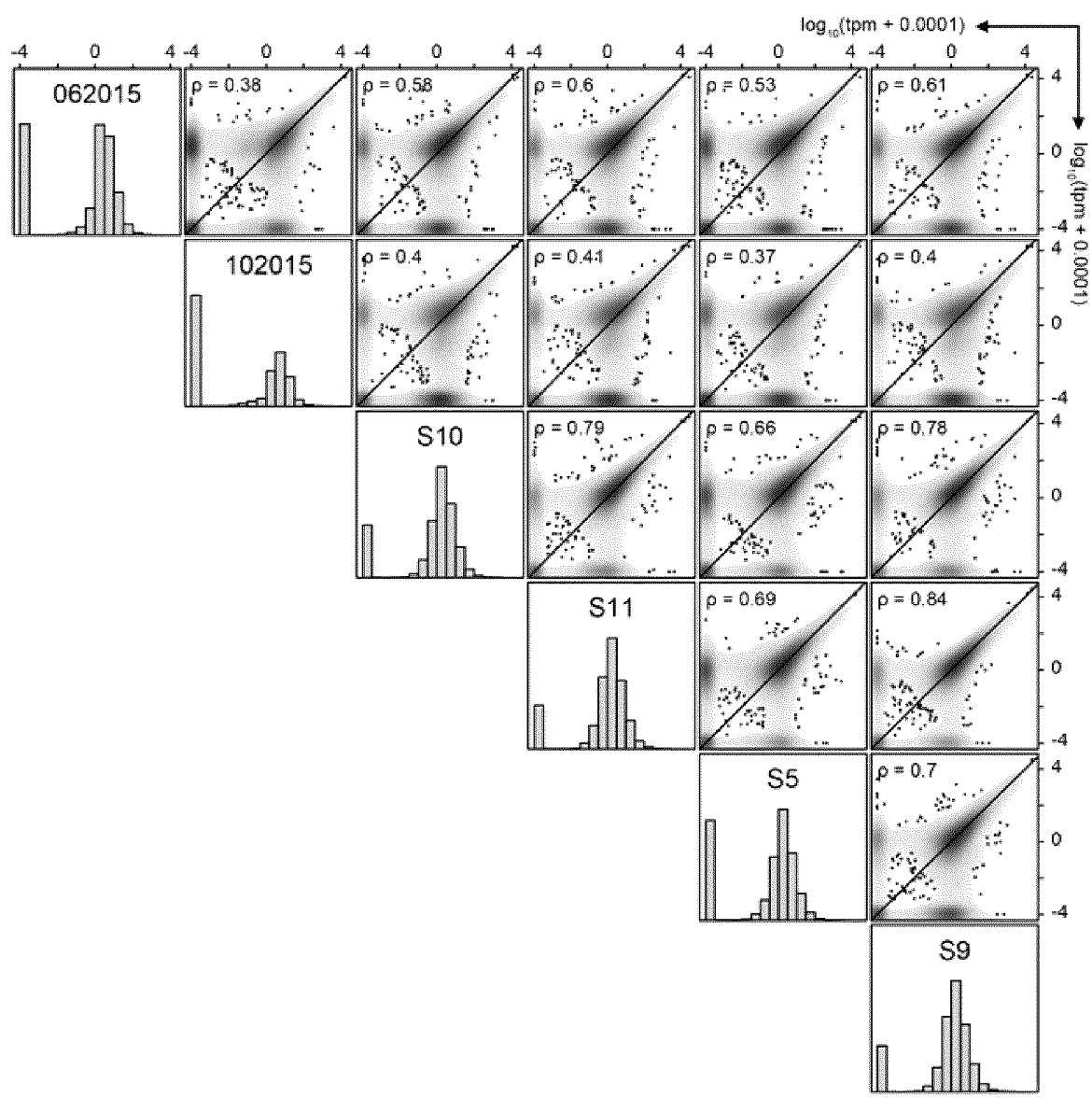
Figure 12B:
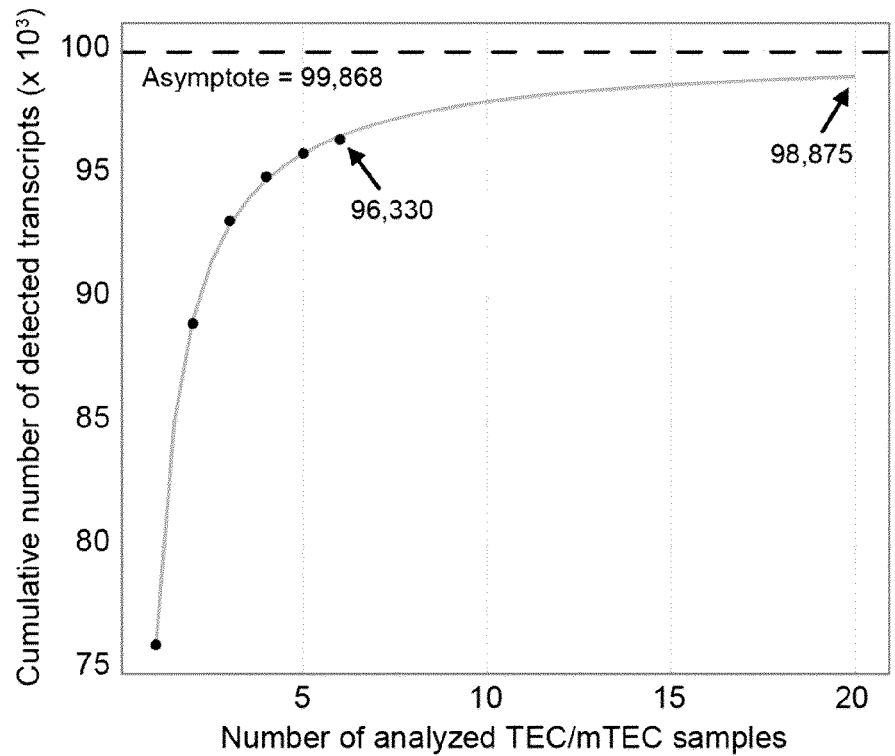

FIGS. 12A-B depict an overview of the human TEC and mTEC transcriptomic landscapes. FIG. 12A: Human TEC (062015 and 102015) and mTEC (S5 to S11) isolated from unrelated donors display similar transcriptomic profiles. Following RNA-Seq, transcripts expressed in at least one donor with a tpm>1, as estimated by kallisto, were selected to plot all one-to-one scatter plots. The Spearman's rank correlation coefficient (p) is indicated at the top left corner of each graph and the black line represents identical expression of transcripts. FIG. 12B: RNA-Seq of additional human TEC/mTEC samples should result in a minimal gain of information. Using the set of expressed transcripts (tpm>1 in at least one sample), the cumulative number of transcripts (cT) that should be detected by adding additional samples to the cohorts (nS, see section Cumulative number of transcripts detected in TEC and mTEC samples of Example 1 below) was extrapolated using the following function:

$$cT = \frac{a(nS-1)}{[b+(nS-1)]} + c$$

with a=23,892.73, b=0.8243389 and c=75,976.11 (grey line). On the graph, the cumulative number of transcripts detected by analyzing nS=6 (the present cohort, black dots) or nS=20 samples, as well as the total number of transcripts that should be detected, which corresponds to $$\lim_{nS \to \infty} \left( \frac{a(nS-1)}{[b+(nS-1)]} + c \right) = a + c = 99,868$$

(asymptote value), is indicated.

Figure 13A:
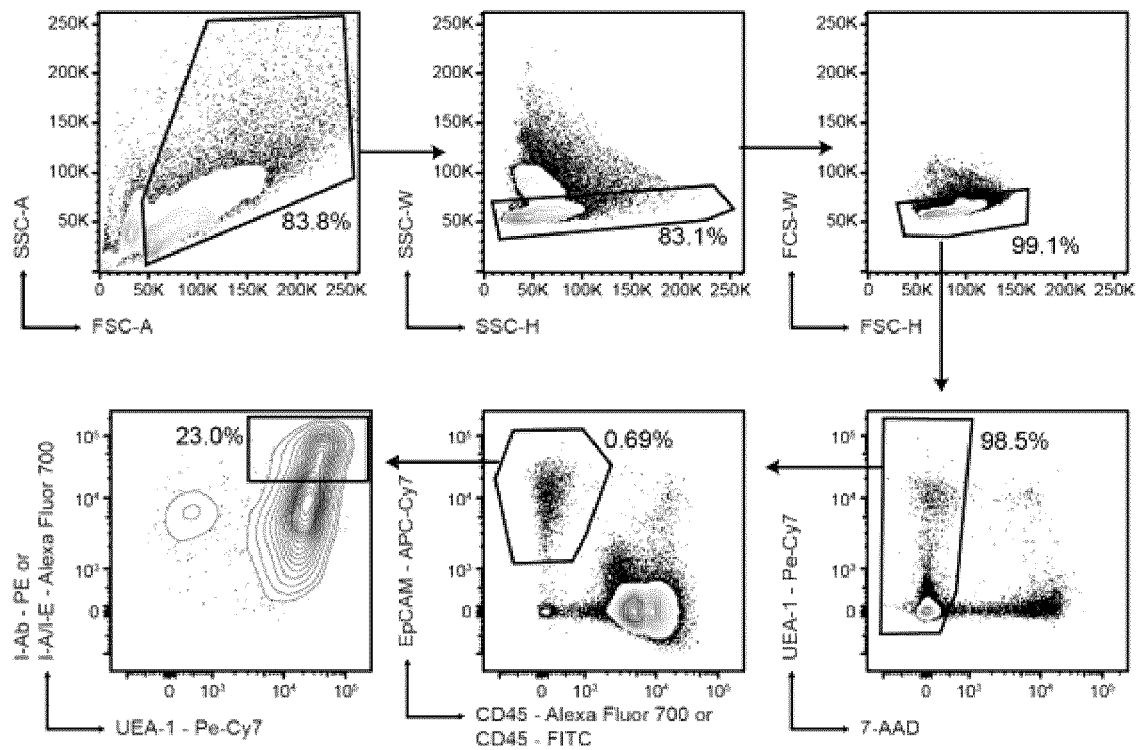
Figure 13B:
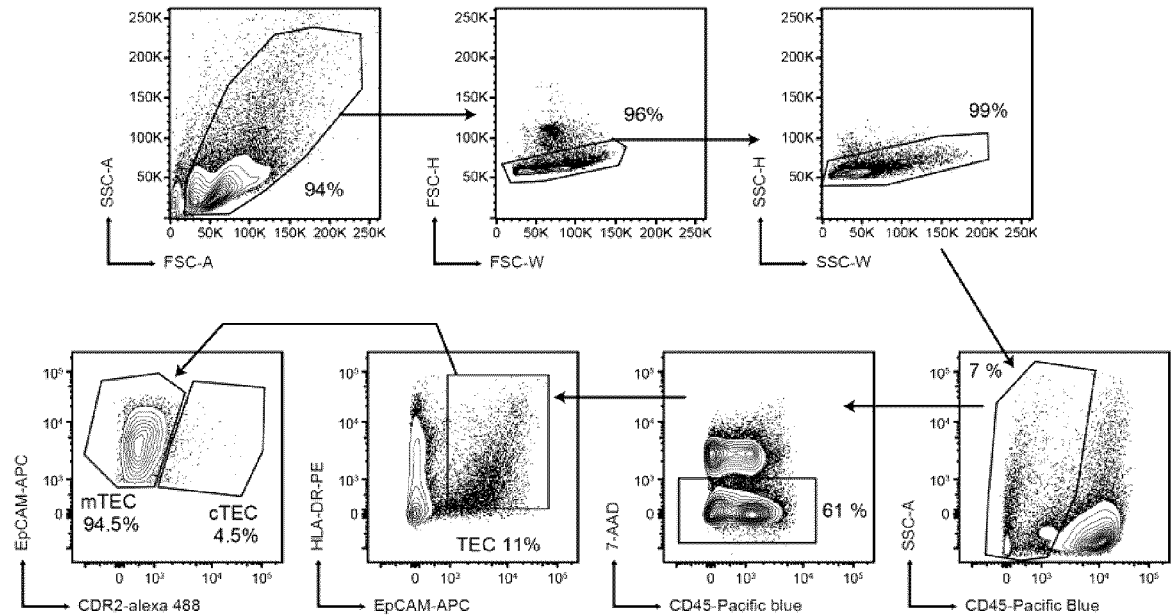
Figure 13C:
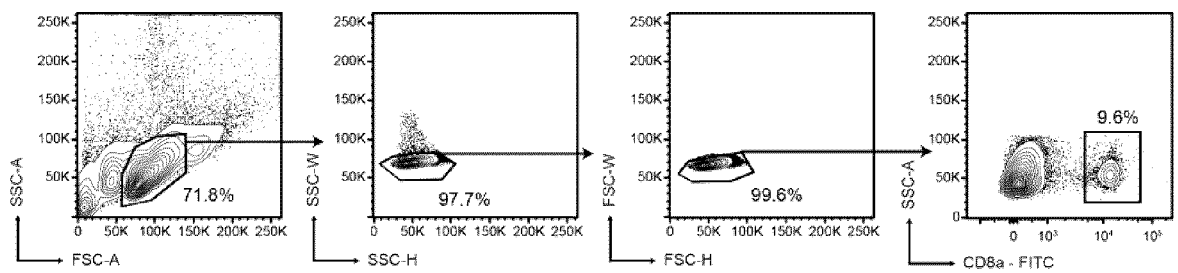

FIGS. 13A-C are graphs showing the gating strategies for cells isolated by FACS sorting. FIG. 13A: Gating strategy for the isolation of murine mTEC$^{hi}$. mTEC$^{hi}$ isolation was performed on single-cell suspensions isolated from thymi of C57BL/6 or Balb/c mice. After doublets exclusion, mTEC$^{hi}$ cells were defined as 7-AAD−, EpCAM+, CD45−(Alexa Fluor 700 for C57BL/6 or FITC for Balb/c mice), UEA-1+ and I-Ab+ (C57BL/6 mice) or I-A/I-E+ (Balb/c mice). FIG. 13B: Gating strategy for the isolation of human TECs and mTECs. Cell sorting was performed on single-cell suspensions isolated from thymi that were obtained from 3-month-old to 7-year-old individuals undergoing corrective cardiovascular surgery. After doublets exclusion, TECs were defined as CD45−, 7-AAD−, EpCAM+ and HLA-DR+. For sorting of mTECs, cells were further defined as CDR2−. FIG. 13C: Gating strategy for the isolation of CD8+ T cells for IFN-γ ELISpot assays. CD8+ T cell isolation was performed on single-cell suspensions isolated from the spleen of naive or immunized C57BL/6 mice. After doublets exclusion, the CD8a marker was used to enrich for CD8+ T cells.

DISCLOSURE OF INVENTION

Terms and symbols of genetics, molecular biology, biochemistry and nucleic acid used herein follow those of standard treatises and texts in the field, e.g. Kornberg and Baker, DNA Replication, Second Edition (W.H. Freeman & Co, New York, 1992); Lehninger, Biochemistry, Sixth Edition (W.H. Freeman & Co, New York, 2012); Strachan and Read, Human Molecular Genetics, fifth Edition (CRC Press, 2018); Eckstein, editor, Oligonucleotides and Analogs: A Practical Approach (Oxford University Press, New York, 1991); and the like. All terms are to be understood with their typical meanings established in the relevant art.

The articles "a" and "an" are used herein to refer to one or to more than one (i.e. to at least one) of the grammatical object of the article. By way of example, "an element" means one element or more than one element. Throughout this specification, unless the context requires otherwise, the words "comprise," "comprises" and "comprising" will be understood to imply the inclusion of a stated step or element or group of steps or elements but not the exclusion of any other step or element or group of steps or elements.

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein.

All methods described herein can be performed in any suitable order unless otherwise indicated herein or otherwise clearly contradicted by context.

The use of any and all examples, or exemplary language (e.g., "such as") provided herein, is intended merely to better illustrate the invention and does not pose a limitation on the scope of the invention unless otherwise claimed.

No language in the specification should be construed as indicating any non-claimed element as essential to the practice of the invention.

Herein, the term "about" has its ordinary meaning. The term "about" is used to indicate that a value includes an inherent variation of error for the device or the method being employed to determine the value, or encompass values close to the recited values, for example within 10% or 5% of the recited values (or range of values).

Considerable efforts are being devoted to discovering actionable TSAs that can be used in therapeutic cancer vaccines. The most common strategy hinges on reverse immunology: i) exome sequencing is performed on tumor cells to identify mutations, and ii) MHC-binding prediction software tools are used to identify which mutated MAPs might be good MHC binders[11,12]. While reverse immunology can enrich for TSA candidates, at least 90% of these candidates are false positives[5,13] because available computational methods may predict MHC binding, but they cannot predict other steps involved in MAP processing[14,15]. To overcome this limitation, a few studies have included mass spectrometry (MS) analyses in their TSA discovery pipeline[16], thereby providing a rigorous molecular definition of several TSAs[17,19]. However, the yield of these approaches has been extremely meager: in melanoma, one of the most mutated tumor type, an average of 2 TSAs per individual tumors have been validated by MS[19], while only a handful of TSAs has been found for other cancer types[15]. The paucity of TSAs is puzzling because injection of TILs or immune checkpoint inhibitors would not cause tumor regression if tumors did not express immunogenic antigens[20]. It was surmised that approaches based on exonic mutations have failed to identify TSAs because they did not take into account two crucial elements. First, these approaches focus only on mTSAs and neglect aeTSAs, essentially because there is currently no method for high-throughput identification of aeTSAs. This represents a major shortcoming because, while mTSAs are private antigens, aeTSAs would be preferred targets for vaccine development since they can be shared by multiple tumors[7,9]. Second, focusing on the exome as the only source of TSAs is very restrictive. The exome (i.e., all protein-coding genes) represents only 2% of the human genome, while up to 75% of the genome can be transcribed and potentially translated[22].

In the studies described herein, the present inventors have developed a proteogenomic workflow able to identify non-tolerogenic TSAs, whether they derive from coding or non-coding regions, simple or complex rearrangements or simply cancer-restricted EREs. To identify non-tolerogenic sequences, rather than trying to map all RNA-sequencing reads and reconstruct potential mutations present in there, the right normal-matched signal, i.e. the one of mTEC', was subtracted to the cancer signal and used the in silico translation of the resulting sequences as a database for MS. Compared to other techniques, the k-mer profiling workflow described herein has several advantages: (i) It is fast. Generating the k-mer-derived portion of the augmented cancer database typically takes less than half a day. (ii) It is unbiased. It captures all cancer-specific sequences regardless of their nature as demonstrated by the identification of TSAs derived from non-coding regions as well as one TSA derived from a deletion of ~7,500 base pairs. (iii) It is modular. To enrich for non-tolerogenic sequences, the cancer data were filtered on mTECh', which were shown to be a good proxy for peripheral expression of antigens, but the data may be filtered otherwise, for example by removing all ENCODE data or adding dbSNP to the mix. The associated k-mer database is generated and added to the collection of normal samples to be filtered against.

In an aspect, the present disclosure provides a method for identifying a tumor antigen candidate in a tumor cell sample, the method comprising:
(a) generating a tumor-specific proteome database by:
  (i) extracting a set of subsequences (k-mers) comprising at least 33 base pairs from tumor RNA-sequences (e.g., RNA sequences obtaining by whole transcriptome sequencing of the tumor cell sample);
  (ii) comparing the set of tumor subsequences of (i) to a set of corresponding control subsequences comprising at least 33 base pairs extracted from RNA-sequences from normal cells;
  (iii) extracting the tumor subsequences that are absent, or underexpressed by at least 4-fold, in the corresponding control subsequences, thereby obtaining tumor-specific subsequences; and
  (iv) in silico translating the tumor-specific subsequences, thereby obtaining the tumor-specific proteome database;
(b) generating a personalized tumor proteome database by:
  (i) comparing the tumor RNA-sequences to a reference genome sequence to identify single-base mutations in said tumor RNA-sequences;
  (ii) inserting the single-base mutations identified in (i) in the reference genome sequence, thereby creating a personalized genome sequence;
  (iii) in silico translating the expressed protein-coding transcripts from said personalized genome sequence, thereby obtaining the personalized proteome database;
(c) comparing the sequences of major histocompatibility complex (MHC)-associated peptides (MAPs) from said tumor with the sequences of the tumor-specific proteome database of (a) and the personalized tumor proteome database of (b) to identify the MAPs; and
(d) identifying a tumor antigen candidate among the MAPs identified in (c), wherein a tumor antigen candidate is a peptide whose sequence and/or encoding sequence is overexpressed in tumor cells relative to normal cells.

In an embodiment, the above-noted method further comprises isolating and sequencing major histocompatibility complex (MHC)-associated peptides (MAPs) from the tumor cell sample.

In an embodiment, the above-noted method further comprises performing whole transcriptome sequencing on the tumor cell sample, thereby obtaining the tumor RNA-sequences.

The term "tumor antigen candidate" as used herein refers to a peptide that binds to a major histocompatibility molecule (MHC) and is present at the surface of tumor cells only, or present at significantly higher levels/frequencies (at least 2-times, preferably at least 4, 5 or 10-times) at the surface of tumor cells relative to non-tumor cells. Such tumor antigen candidate may be targeted to induce a T-cell response against tumor cells expressing the antigen at their surface.

Methods for isolating MHC-associated peptides (MAPs) from a cell sample are well known in the art. The most commonly used technique is mild acid elution (MAE) of MHC-associated peptides from living cells, as described in Fortier et al. (*J. Exp. Med.* 205(3): 595-610, 2008). Another technique is immunoprecipitation or affinity purification of peptide-MHC class I complexes followed by peptide elution (see, e.g., Gebreselassie et al., *Hum Immunol.* 2006 November; 67(11): 894-906). Two high-throughput strategies based on the latter approach have been implemented. The first is based on transfection of cell lines with expression vectors coding soluble secreted MHCs (lacking a functional transmembrane domain) and elution of peptides associated with secreted MHCs (Barnea et al., *Eur J Immunol.* 2002 January; 32(1):213-22; and Hickman H D et al., *J Immunol.* 2004 Mar. 1; 172(5):2944-52). The second approach hinges on chemical or metabolic labeling to provide quantitative profiles of MHC-associated peptides (Weinzierl A O et al., *Mol Cell Proteomics.* 2007 January; 6(1):102-13. Epub 2006 Oct. 29; Lemmel C et al., *Nat Biotechnol.* 2004 April; 22(4):450-4. Epub 2004 Mar. 7; Milner E, *Mol Cell Proteomics.* 2006 February; 5(2):357-65. Epub 2005 Nov. 4).

Eluted MAPs may be subjected to any purification/enrichment steps, including size exclusion chromatography or ultrafiltration (using a filter with a cut-off of about 5000 Da, for example about 3000 Da), reverse-phase chromatography (hydrophobic chromatography) and/or ion exchange chromatography (e.g., cation exchange chromatography), prior to further analysis. The sequence of the eluted MAPs may be determined using any method known in the art for sequencing peptides/proteins, such as mass spectroscopy (Tandem mass spectrometry or MS/MS, as described below) and the Edman degradation reaction.

Whole transcriptome sequencing (also referred to as "total RNA sequencing", "RNA sequencing" or RNA-seq) refers to the sequencing of all RNAs present in a sample (tumor sample, normal cell sample), including coding RNAs as well as multiple forms of noncoding RNAs such as miRNAs, snRNAs and tRNA. Methods for performing whole transcriptome sequencing, e.g., Next Generation Sequencing (NGS) methods, are well known in the art. Multiple NGS platforms which are commercially available (e.g., from Illumina (NextSeg™, HiSeq™), Thermofisher (Ion Total™ RNA-Seq Kit), Clontech (SMARTer™) or which are mentioned in the literature can be used in the method described herein, e.g. those described in detail in Zhang et al. 2011: The impact of next-generation sequencing on genomics. *J. Genet Genomics* 38(3), 95-109; or in Voelkerding et al. 2009: Next generation sequencing: From basic research to diagnostics. *Clinical chemistry* 55, 641-658.

Preferably, RNA preparations serve as starting material for NGS. Such nucleic acids can be easily obtained from samples such as biological material, e.g. from fresh, flash-frozen or formalin-fixed paraffin embedded tumor tissues or from freshly isolated cells or from circulating tumor cells (CTCs) which are present in the peripheral blood of patients. Normal or control RNAs can be extracted from normal, somatic tissue or germline cells. The RNA sequences from normal cells may correspond to a collection of RNA sequences from different types of normal cells, e.g. normal cells from different tissues. The RNA sequences from normal cells may also be obtained from thymic cells, preferably medullary thymic epithelial cells (mTEC) such as MHC $II^{high}$ medullary thymic epithelial cells ($mTEC^{hi}$). $mTEC^{hi}$ cells advantageously have a unique promiscuous gene expression profile as they express ~70 to 90% of protein-coding sequences of somatic cells, and their MAPs can induce central immune tolerance.

The method described herein comprises generating a tumor-specific proteome database using an alignment-free RNA-seq analysis workflow, called k-mer profiling, which comprises sequences derived from the translation of structural variants (any type of mutations including large insertions or deletions (InDels) or fusions) and non-coding regions. The tumor and normal RNA sequences (RNA-seq reads) are "chopped" or "split" into k-mers, i.e. subsequences of length k with k≥33 nucleotides. Since peptides bound to MHC class I molecules (MAPs) are generally not more than 11 amino-acid-long (and thus encoded by 33 nucleotide-long sequences), splitting the RNA sequences into subsequences of at least 33 nucleotides minimizes the risk of missing potential MAPs. The skilled person would understand that to minimize the size of the tumor-specific proteome database, splitting the RNA sequences into sub-sequences of 33 nucleotides (i.e., k=33 nucleotides) is preferred for identifying MHC class I-restricted tumor antigens. The skilled person would also understand that to identify MHC class II-restricted tumor antigens, the minimal k-mer length should be increased from 33 to 54 nucleotides (k≥54 nucleotides), MHC II-associated peptides generally ranging from 13 to 18 amino acid-long. The tumor subsequences are then compared to a set of corresponding control subsequences (from RNA sequences of normal cells) to extract tumor subsequences that are absent, or underexpressed by at least 4-fold (preferably at least 5-, 6-, 7-, 8-, 9- or 10-fold), in the corresponding control subsequences. In an embodiment, to minimize the redundancy inherent to the k-mer space, the method further comprises assembling overlapping tumor-specific subsequences into longer tumor subsequences (typically referred to as contigs). The tumor-specific subsequences or contigs are then in silico translated (e.g., 3-frame or 6-frame translated, depending on whether the subsequences or contigs are derived from the coding or non-coding strand) to obtain the tumor-specific proteome database. In an embodiment, the protein fragments of less than 8 amino acids (the minimal length of MHC class I peptides) or 13 amino acids (the minimal length of MHC class II peptides) are removed from the tumor-specific proteome database.

In an embodiment, the method further comprises generating a k-mer database with k=24 nucleotides (for MHC class I peptides) or k=39 (for MHC class II peptides) from the RNA sequences (from normal and tumor cells) to obtain cancer/tumor and normal 24 (or 39) nucleotide-long k-mer databases. These databases may be used for comparison with the MAP-coding sequences (MCS) to determine whether the MCS that are overexpressed or overrepresented in the tumor cells, as described below.

The method also comprises the generation of a personalized tumor proteome database. To do so, the tumor RNA-sequences (tumor RNA-seq reads) are compared to a reference genome sequence to identify single-base mutations in the tumor RNA-sequences. These mutations are then inserted in the reference genome to obtain a personalized tumor genome, from which it is possible to obtain the corresponding personalized tumor proteome database containing the canonical translation product sequences of all expressed protein-coding transcript sequences. The generation of a personalized tumor proteome database, which permits to identify WT MAPs and mutated TSAs (neoantigens) coded by the canonical frame of the exome, also improves the reliability of the databases used for MS analysis by not overly biasing the database towards tumor-specific sequences, which would result in the identification of several false-positives.

In an embodiment, the method also comprises the generation of a personalized normal proteome database. To do so, RNA-sequences from normal cells (normal RNA-seq reads) are compared to a reference genome sequence to identify single-base mutations in the normal RNA-sequences. These mutations are then inserted in the reference genome to obtain a personalized normal genome, from which it is possible to obtain the corresponding personalized normal proteome database containing the canonical translation product sequences of all expressed protein-coding transcript sequences. This personalized normal proteome database may be used to filter MAPs expressed in normal (non-tumor) cells, which are not suitable TSA candidates.

The term "reference genome" as used herein refers to the human genome assemblies reported in the literature, and includes for example the Genome Reference Consortium Human Build 38 (GRCh38, RefSeq: accession No. GCF_000001405.37), Hs_Celera_WGSA (Celera Genomics; Istrail S. et al., *Proc Natl Acad Sci USA*. 2004; 101(7): 1916-21). Epub 2004 Feb. 9), HuRef and HuRef Prime (J. Craig Venter Institute; Levy S, et al. *PLoS Biology*. 2007; 5: 2113-2144), YH1 and BGIAF (Beijing Genomics Institute; Li R, et al. *Genome Research*. 2010; 20: 265-272), HsapALLPATHS1 (Broad Institute), and the like. A list of reference human genome assemblies may be found in the "Assembly" database of the National Center for Biotechnology Information (NCBI). In an embodiment, the reference genome is GRCh38.

The sequences of the MAPs obtained in step (a) of the method are then compared with (e.g., blasted against) the sequences of the tumor-specific proteome database and the personalized tumor proteome database, which allows the identification of MAPs.

The tumor antigen candidates may be identified among the MAPs identified above. Such tumor antigen candidates correspond to peptides whose sequences and/or encoding sequences are overexpressed in tumor cells relative to normal cells.

In an embodiment, the method further comprises eliminating or discarding MAPs whose sequences are detected in the normal personalized proteome database.

In an embodiment, the method comprises retrieving the coding sequences of the MAPs identified i.e. the MAP-coding sequence (MCS). In another embodiment, the method comprises transforming the MCS into k-mer sets of 24 (for MHC class I peptides) or 39 (for MHC class II peptides) nucleotides. In another embodiment, these k-mer sets derived from MCS are compared to the cancer/tumor and normal 24- (or 39-) nucleotides k-mer databases.

In an embodiment, the method comprises:
(a) isolating and sequencing major histocompatibility complex (MHC)-associated peptides (MAPs) in a tumor cell sample;
(b) performing whole transcriptome sequencing on said tumor cell sample, thereby obtaining tumor RNA-sequences;
(c) generating a tumor-specific proteome database by:
   (i) extracting a set of subsequences (k-mers) comprising at least 33 nucleotides from said tumor RNA-sequences;
   (ii) comparing the set of tumor subsequences of (i) to a set of corresponding control subsequences comprising at least 33 nucleotides extracted from RNA-sequences from normal cells;
   (iii) extracting the tumor subsequences that are absent, or underexpressed by at least 4-fold, in the corresponding control subsequences, thereby obtaining tumor-specific subsequences; and
   (iv) in silico translating the tumor-specific subsequences, thereby obtaining the tumor-specific proteome database;
(d) generating a personalized tumor proteome database by:
   (i) comparing the tumor RNA-sequences to a reference genome sequence to identify single-base mutations in said tumor RNA-sequences;
   (ii) inserting the single-base mutations identified in (i) in the reference genome sequence, thereby creating a personalized tumor genome sequence;
   (iii) in silico translating the expressed protein-coding transcripts from said personalized tumor genome sequence, thereby obtaining the personalized tumor proteome database;
(e) generating a personalized normal proteome database by:
   (i) comparing RNA-sequences from normal cells to a reference genome sequence to identify single-base mutations in said normal RNA-sequences;
   (ii) inserting the single-base mutations identified in (i) in the reference genome sequence, thereby creating a personalized normal genome sequence;
   (iii) in silico translating the expressed protein-coding transcripts from said personalized normal genome sequence, thereby obtaining the personalized normal proteome database;
(f) generating a normal and a tumor k-mer database by (i) extracting a set of subsequences comprising at least 24 nucleotides from said RNA-sequences from normal cells and said tumor RNA-sequences;
(g) comparing the sequences of the MAPs obtained in (a) with the sequences of the tumor-specific proteome database of (c) and the personalized tumor proteome database of (d) to identify the MAPs; and
(h) identifying a tumor antigen candidate among the MAPs identified in (f), wherein a tumor antigen candidate corresponds to a MAP (1) whose sequence is not present in the personalized normal proteome database; and (2) (i) whose sequence is present in the personalized tumor proteome database; and/or (i) whose encoding sequence is overexpressed or overrepresented in said tumor k-mer database relative to said normal k-mer database.

In an embodiment, the encoding sequence is transformed into a set of MAP-derived k-mers (e.g., 24 nts k-mers), and the expression or representation of the MAP-derived k-mers in the tumor and normal k-mer databases is determined. Overexpressed or overrepresented as used herein means that the sequence is present in the tumor k-mer database at a level that is at least 2-fold, preferably at least 3-, 4- or 5-fold, and more preferably at least 10-fold, relative to the normal k-mer database. In an embodiment, the encoding sequence or MAP-derived k-mer is absent from the normal k-mer database.

In an embodiment, referring to FIG. 7A, the identification and validation of the TSA candidate is achieved as follows.

Each MAP and its associated MAP-coding sequence(s) (MCS) is queried to the relevant cancer and normal personalized proteome or cancer and normal 24 nucleotide-long k-mer databases. MAPs detected in the normal personalized proteome were excluded. MAPs only present in the cancer personalized proteome and/or cancer k-mer database are identified/selected as TSA candidates. For the MAPs absent from both personalized proteomes but present in both k-mer databases, they are selected if their MCS is overexpressed (e.g., at least 2-fold, preferably at least 5-fold and more preferably at least 10-fold) in cancer cells relative to normal cells. If the MAP is encoded by several MCS, it is identified/selected as a TSA candidate if their respective MCSs were concordant, i.e. if it is consistently flagged as a TSA candidate. In an embodiment, since they are difficult to distinguish by MS, TSA candidates with I/L variants are excluded as TSA candidates.

In an embodiment, prior to the comparison, eluted MAPs are filtered to select for 8 to 11 amino acid-long peptides. In another embodiment, prior to the comparison, eluted MAPs are filtered to select for those that have a percentile rank <2% for at least one on the relevant MHC I molecules, as predicted by NetMHC software version 4.0 (Andreatta M, Nielsen M, *Bioinformatics* (2016) February 15; 32(4):511-7; Nielsen M, et al., *Protein Sci.*, (2003) 12:1007-17).

In an embodiment, the method further comprises comparing the coding sequence of the tumor antigen candidate to sequences from normal tissues. In embodiments, the sequences of at least 5, 10, 15, 20 or 25 different tissues are used. The sequences from normal tissues may be obtained from public databases such as Expression Atlas (Petryszak et al., *Nucleic Acids Research*, Volume 44, Issue D1, 4 Jan. 2016, Pages D746-D752), scRNASeqDB (Cao Y, et al. (2017). Genes 8(12), 368), RNA-Seq Atlas (Krupp et al., *Bioinformatics*, Volume 28, Issue 8, 15 Apr. 2012, Pages 1184-1185) and Encode, or may be generated by performing RNA-seq on normal tissues. In an embodiment, the method further comprising selecting the tumor antigen candidate if (1) its coding sequence is not expressed in any of the normal tissues assessed, or if it is expressed only in MHC class I-negative tissues, or (2) its coding sequence is expressed is less than 50%, preferably less than 45%, 40%, 35% or 30% of MHC class I-positive tissues assessed. In an embodiment, the tumor antigen candidate is selected if its coding sequence is expressed in less than 7, preferably less than 6, 5, 4 or 3 of the normal tissues assessed.

In an embodiment, the method further comprises determining the genomic location of the coding sequence of the TSA candidate, and selecting the TSA candidate if (1) the coding sequence matches to a concordant genomic location; (2) the coding sequence does not match to an hypervariable region (such as the H2, Ig of TCR genes) or to multiple genes; and (3) does not overlap synonymous mutations. Such determination may be performed using the BLAT tool from the UCSC Genome Browser (Kent W J. *Genome Res.* 2002 April; 12(4):656-64) and/or the Integrative genomics viewer (IGV) tool (Robinson et al., *Nat Biotechnol.* 2011 January; 29(1):24-6).

In an embodiment, the method further comprises determining or predicting the binding of the tumor antigen candidate (TSA candidate) identified to an MHC class I molecule. The binding may be a predicted binding affinity ($IC_{50}$) of peptides to the allelic products, which may be obtained using tools such as the NetMHC. An overview of the various available MHC class I peptide binding tools is provided in Peters B et al., *PLoS Comput Biol* 2006, 2(6):e65; Trost et al., *Immunome Res* 2007, 3(1):5; Lin et al., *BMC Immunology* 2008, 9:8). The binding of the TSA candidate identified to a MHC class I molecule may be determined using other known methods, for example the T2 Peptide Binding Assay. T2 cell lines are deficient in TAP but still express low amounts of MHC class I on the surface of the cells. The T2 binding assay is based upon the ability of peptides to stabilize the MHC class I complex on the surface of the T2 cell line. T2 cells are incubated with a specific peptide (e.g., a TSA candidate), stabilized MHC class I complexes are detected using a pan-HLA class I antibody, an analysis is carried out (by flow cytometry, for example) and binding is assessed in relation to a non-binding negative control. The presence of stabilized peptide/MHC class I complexes at the surface is indicative that the peptide (e.g., candidate TSA) binds to MHC class I molecules.

The binding of a peptide of interest (e.g., TSA candidate) to MHC may also be assessed based on its ability to inhibit the binding of a radiolabeled probe peptide to MHC molecules. MHC molecules are solubilized with detergents and purified by affinity chromatography. They are then incubated for 2 days at room temperature with the peptide of interest (e.g., TSA candidate) and an excess of a radiolabeled probe peptide, in the presence of a cocktail of protease inhibitors. At the end of the incubation period, MHC-peptide complexes are separated from unbound radiolabeled peptide by size-exclusion gel-filtration chromatography, and the percent bound radioactivity is determined. The binding affinity of a particular peptide for an MHC molecule may be determined by co-incubation of various doses of unlabeled competitor peptide with the MHC molecules and labeled probe peptide. The concentration of unlabeled peptide required to inhibit the binding of the labeled peptide by 50% ($IC_{50}$) can be determined by plotting dose versus % inhibition (see, e.g., *Current Protocols in Immunology* (1998) 18.3.1-18.3.19, John Wiley & Sons, Inc.).

The binding of the TSA candidate identified to a MHC class I molecule may also be determined using a T-cell epitope discovery system/tool, such as the ProImmune REVEAL® & ProVE® T cell epitope discovery systems or the NetMHC tool (see, e.g., Desai and Kulkarni-Kale, *Methods Mol Biol.* 2014; 1184: 333-64).

In an embodiment, the method further comprises assessing the number or frequency of T cells recognizing the tumor antigen candidate in a cell population, for example in a cell sample (e.g., PBMCs) from a subject. The number or frequency of T cells recognizing a given antigen may be assessed using various methods known in the art, for example by contacting the cell population with multimeric MHC class I molecules (e.g., MHC tetramers) comprising said tumor antigen candidate in their peptide binding groove, and determining the number of cells labelled with the multimeric MHC class I molecules. The multimeric MHC class I molecules may be detectably labelled with a fluorophore (direct labelling), or may be tagged with a moiety that is recognized by a labelled ligand (indirect or secondary labelling). Alternatively, the number or frequency of T cells recognizing the TSA candidate may be assessed by determining the number/frequency of T cells activated in the presence of the TSA candidate under suitable conditions for T cell activation. The number/frequency of activated T cells may be assessed by detecting the cells secreting a cytokine induced by T cell activation, e.g., IFN-γ or IL-2 (e.g., by ELISpot or flow cytometry).

In an embodiment, the method further comprises assessing the ability of the tumor antigen candidate to induce T cell activation, for example by contacting a T cell population with cells (e.g., APCs such as dendritic cells) having the tumor antigen candidate bound to MHC class I molecules at their cell surface, and measuring at least one parameter of T cell activation, such as proliferation, cytokine/chemokine production (e.g., IFN-γ or IL-2 production), cytotoxic killing, and the like.

In an embodiment, the method further comprises assessing the ability of the tumor antigen candidate to T-cell-mediated tumor cell killing and/or to inhibit tumor growth. This may be achieved in vitro using tumor cells, or in vivo using a suitable animal model.

In an embodiment, the tumor antigen candidate has a length of about 7 to 20 amino acids, and more particularly of about 8 to 18 amino acids, preferably a length of 8 to 11 (for MHC class I tumor antigens) or 13 to 18 (for MHC class II tumor antigens) amino acids.

The methods described herein may be useful for identifying tumor antigen candidate for any type of cancers by performing the whole transcriptome sequencing on the tumor/cancer cell sample of interest. Examples of such cancers include, but are not limited to, carcinoma, lymphoma, blastoma, sarcoma, and leukemia, and more particularly bone cancer, blood/lymphoid cancer such as leukemia (AML, CML, ALL), myeloma, lymphoma, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. Thus, in an embodiment, the tumor cell sample using in step (a) of the method described herein is a sample comprising cells of any of the above-noted cancers.

In another aspect, the present disclosure relates to a tumor antigen peptide (or tumor-specific peptide) identified herein, i.e. comprising one of the amino acid sequences disclosed in Tables 1a, 1b, 2a-2d, or 3a-3c (SEQ ID NOs: 1-39), preferably Tables 2a-2d, or 3a-3c (SEQ ID NOs: 17-39), or a variant thereof having one or more mutations relative to the sequences of SEQ ID NOs: 1-39.

In general, peptides such as tumor antigen peptides presented in the context of HLA class I vary in length from about 7 or 8 to about 15, or preferably 8 to 14 amino acid residues. In some embodiments of the methods of the disclosure, longer peptides comprising the tumor antigen peptide sequences defined herein are artificially loaded into cells such as antigen presenting cells (APCs), processed by the cells and the tumor antigen peptide is presented by MHC class I molecules at the surface of the APC. In this method, peptides/polypeptides longer than 15 amino acid residues (i.e. a tumor antigen precursor peptide) can be loaded into APCs, are processed by proteases in the APC cytosol providing the corresponding tumor antigen peptide as defined herein for presentation. In some embodiments, the precursor peptide/polypeptide that is used to generate the tumor antigen peptide defined herein is for example 1000, 500, 400, 300, 200, 150, 100, 75, 50, 45, 40, 35, 30, 25, 20 or 15 amino acids or less. Thus, all the methods and processes using the tumor antigen peptides described herein include the use of longer peptides or polypeptides (including the native protein), i.e. tumor antigen precursor peptides/ polypeptides, to induce the presentation of the "final" 8-14 tumor antigen peptide following processing by the cell (APCs). In some embodiments, the herein-mentioned tumor antigen peptide is about 8 to 14, 8 to 13, or 8 to 12 amino acids long (e.g., 8, 9, 10, 11, 12 or 13 amino acids long), small enough for a direct fit in an HLA class I molecule. In an embodiment, the tumor antigen peptide comprises 20 amino acids or less, preferably 15 amino acids or less, more preferably 14 amino acids or less. In an embodiment, the tumor antigen peptide comprises at least 7 amino acids, preferably at least 8 amino acids, more preferably at least 9 amino acids.

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of tumor antigen peptides. Examples of naturally occurring amino acids are glycine, alanine, valine, leucine, isoleucine, serine, threonine, etc. Other amino acids include for example non-genetically encoded forms of amino acids, as well as a conservative substitution of an L-amino acid. Naturally-occurring non-genetically encoded amino acids include, for example, beta-alanine, 3-amino-propionic acid, 2,3-diaminopropionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienyl-alanine, methionine sulfoxide, L-homoarginine (Hoarg), N-acetyl lysine, 2-amino butyric acid, 2-amino butyric acid, 2,4,-diaminobutyric acid (D- or L-), p-aminophenylalanine, N-methylvaline, homocysteine, homoserine (HoSer), cysteic acid, epsilon-amino hexanoic acid, delta-amino valeric acid, or 2,3-diaminobutyric acid (D- or L-), etc. These amino acids are well known in the art of biochemistry/peptide chemistry. In an embodiment, the tumor antigen peptide comprises only naturally-occurring amino acids.

In embodiments, the tumor antigen peptides described herein include variant peptides with altered sequences containing substitutions of functionally equivalent amino acid residues, relative to the herein-mentioned sequences. For example, one or more amino acid residues within the sequence can be substituted by another amino acid of a similar polarity (having similar physico-chemical properties) which acts as a functional equivalent, resulting in a silent alteration. Substitution for an amino acid within the sequence may be selected from other members of the class to which the amino acid belongs. For example, positively charged (basic) amino acids include arginine, lysine and histidine (as well as homoarginine and ornithine). Nonpolar (hydrophobic) amino acids include leucine, isoleucine, alanine, phenylalanine, valine, proline, tryptophan and methionine. Uncharged polar amino acids include serine, threonine, cysteine, tyrosine, asparagine and glutamine. Negatively charged (acidic) amino acids include glutamic acid and aspartic acid. The amino acid glycine may be included in either the nonpolar amino acid family or the uncharged (neutral) polar amino acid family. Substitutions made within a family of amino acids are generally understood to be conservative substitutions. The herein-mentioned tumor antigen peptide may comprise all L-amino acids, all D-amino acids or a mixture of L- and D-amino acids. In an embodiment, the herein-mentioned tumor antigen peptide comprises all L-amino acids.

In an embodiment, in the sequences of the tumor antigen peptides comprising one of sequences set forth in SEQ ID NOs: 1-39, the amino acid residues that do not substantially contribute to interactions with the T-cell receptor may be modified by replacement with other amino acid whose incorporation does not substantially affect T-cell reactivity and does not eliminate binding to the relevant MHC molecule. In an embodiment, the tumor antigen peptide variant is sequence-optimized to improve MHC binding, i.e. comprises one or more mutations (e.g. 1, 2 or 3 mutations), for example amino acid substitutions, that enhance the binding to the MHC molecule. The binding affinities of tumor antigen peptide variant may be assessed, e.g., using MHC binding prediction tools such as NetMHC4.0; NetMHCpan4.0; and MHCflurry 1.2.0. Sequence-optimized tumor antigen peptide variants can be considered, for example, if predicting binding affinity to a specific HLA is equivalent, or preferably stronger, than the native tumor antigen peptide. Selected sequence-optimized target peptides can then be screened for in vitro binding to specific HLAs using methods known in the art, for example using ProImmune's REVEAL assay.

The tumor antigen peptide may also be N- and/or C-terminally capped or modified to prevent degradation, increase stability, affinity and/or uptake, and thus the present disclosure provides a variant of the tumor antigen peptide having the formula $Z^1$-X-$Z^2$, wherein X is the sequences of the tumor antigen peptides set forth in SEQ ID NOs: 1-39, preferably 17-39. In an embodiment, the amino terminal residue (i.e., the free amino group at the N-terminal end) of the tumor antigen peptide is modified (e.g., for protection against degradation), for example by covalent attachment of a moiety/chemical group ($Z^1$). $Z^1$ may be a straight chained or branched alkyl group of one to eight carbons, or an acyl group (R—CO—), wherein R is a hydrophobic moiety (e.g., acetyl, propionyl, butanyl, iso-propionyl, or iso-butanyl), or an aroyl group (Ar—CO—), wherein Ar is an aryl group. In an embodiment, the acyl group is a $C_1$-$C_{16}$ or $C_3$-$C_{16}$ acyl group (linear or branched, saturated or unsaturated), in a further embodiment, a saturated $C_1$-$C_6$ acyl group (linear or branched) or an unsaturated $C_3$-$C_6$ acyl group (linear or branched), for example an acetyl group ($CH_3$—CO—, Ac). In an embodiment, $Z^1$ is absent. The carboxy terminal residue (i.e., the free carboxy group at the C-terminal end of the tumor antigen peptide) of the tumor antigen peptide may be modified (e.g., for protection against degradation), for example by covalent attachment of a moiety/chemical group ($Z^2$), for example by amidation (replacement of the OH group by a $NH_2$ group), thus in such a case $Z^2$ is a $NH_2$ group. In an embodiment, $Z^2$ may be an hydroxamate group, a nitrile group, an amide (primary, secondary or tertiary) group, an aliphatic amine of one to ten carbons such as methyl amine, iso-butylamine, iso-valerylamine or cyclohexylamine, an aromatic or arylalkyl amine such as aniline, napthylamine, benzylamine, cinnamylamine, or phenylethylamine, an alcohol or $CH_2OH$. In an embodiment, $Z^2$ is absent. In an embodiment, the tumor antigen peptide comprises one of the sequences disclosed in SEQ ID NOs: 1-39, preferably 17-39. In an embodiment, the tumor antigen peptide consists of one of the sequences disclosed in SEQ ID NOs: 1-39, preferably 17-39, i.e. wherein $Z^1$ and $Z^2$ are absent.

In an embodiment, the present disclosure provides a tumor antigen peptide binding to an HLA molecule of the HLA-A2 allele, preferably of the HLA-A*02:01 allele, and comprises or consists of one of the amino acid sequences set forth in any one of SEQ ID NOs: 17-19, 27 and 28.

In an embodiment, the present disclosure provides a tumor antigen peptide binding to an HLA molecule of the HLA-B40 allele, preferably of the HLA-B*40:01 allele, and comprises or consists of the amino acid sequence set forth in SEQ ID NO: 20.

In an embodiment, the present disclosure provides a tumor antigen peptide binding to an HLA molecule of the HLA-A11 allele, preferably of the HLA-A*11:01 allele, and comprises or consists of one of the amino acid sequences set forth in any one of SEQ ID NOs: 21-23 and 29-35.

In an embodiment, the present disclosure provides a tumor antigen peptide binding to an HLA molecule of the HLA-B08 allele, preferably of the HLA-B*08:01 allele, and comprises or consists the amino acid sequences set forth in SEQ ID NO: 24 or 25.

In an embodiment, the present disclosure provides a tumor antigen peptide binding to an HLA molecule of the HLA-B07 allele, preferably of the HLA-B*07:02 allele, and comprises or consists of the amino acid sequence set forth in SEQ ID NO: 26 or 36.

In an embodiment, the present disclosure provides a tumor antigen peptide binding to an HLA molecule of the HLA-A24 allele, preferably of the HLA-A*24:02 allele, and comprises or consists the amino acid sequences set forth in SEQ ID NO: 38 or 39.

In an embodiment, the present disclosure provides a tumor antigen peptide binding to an HLA molecule of the HLA-007 allele, preferably of the HLA-C*07:01 allele, and comprises or consists of the amino acid sequence set forth in SEQ ID NO: 37.

In an embodiment, the tumor antigen peptide is a leukemia tumor antigen peptide and comprises or consists of one of the amino acid sequences set forth in any one of SEQ ID NOs: 17-28.

In an embodiment, the tumor antigen peptide is a lung tumor antigen peptide and comprises or consists of one of the amino acid sequences set forth in any one of SEQ ID NOs: 29-39.

In an embodiment, the tumor antigen peptide is encoded by a sequence located in a non-coding region of the genome. In an embodiment, the tumor antigen peptide is encoded by a sequence located in an untranslated transcribed region (UTR), i.e. a 3'-UTR or 5'-UTR region. In another embodiment, the tumor antigen peptide is encoded by a sequence located in an intron. In another embodiment, the tumor antigen peptide is encoded by a sequence located in an intergenic region. In an embodiment, the tumor antigen peptide is encoded by a sequence located in an endogenous retroelement (ERE). In another embodiment, the tumor antigen peptide is encoded by a sequence located in an exon and originates from a frameshift.

The tumor antigen peptides of the disclosure may be produced by expression in a host cell comprising a nucleic acid encoding the tumor antigen peptides (recombinant expression) or by chemical synthesis (e.g., solid-phase peptide synthesis). Peptides can be readily synthesized by manual and/or automated solid phase procedures well known in the art. Suitable syntheses can be performed for example by utilizing "T-boc" or "Fmoc" procedures. Techniques and procedures for solid-phase synthesis are described in for example Solid Phase Peptide Synthesis: A Practical Approach, by E. Atherton and R. C. Sheppard, published by IRL, Oxford University Press, 1989. Alternatively, the tumor antigen peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the tumor antigen peptides are described in Nakagawa et al., *J. Am. Chem. Soc.* 107: 7087-7092, 1985. In an embodiment, the tumor antigen peptide is chemically synthesized (synthetic peptide). Another embodiment of the present disclosure relates to a non-naturally occurring peptide wherein said peptide consists or consists essentially of an amino acid sequences defined herein and has been synthetically produced (e.g., synthesized) as a pharmaceutically acceptable salt. The salts of the tumor antigen peptides according to the present disclosure differ substantially from the peptides in their state(s) in vivo, as the peptides as generated in vivo are no salts. The non-natural salt form of the peptide may modulate the solubility of the peptide, in particular in the context of pharmaceutical compositions comprising the peptides, e.g. the peptide vaccines as disclosed herein. Preferably, the salts are pharmaceutically acceptable salts of the peptides.

In an embodiment, the herein-mentioned tumor antigen peptide is substantially pure. A compound is "substantially pure" when it is separated from the components that naturally accompany it. Typically, a compound is substantially pure when it is at least 60%, more generally 75%, 80% or 85%, preferably over 90% and more preferably over 95%, by weight, of the total material in a sample. Thus, for example, a polypeptide that is chemically synthesized or produced by recombinant technology will generally be substantially free from its naturally associated components, e.g. components of its source macromolecule. A nucleic acid molecule is substantially pure when it is not immediately contiguous with (i.e., covalently linked to) the coding sequences with which it is normally contiguous in the naturally occurring genome of the organism from which the nucleic acid is derived. A substantially pure compound can be obtained, for example, by extraction from a natural source; by expression of a recombinant nucleic acid molecule encoding a peptide compound; or by chemical synthesis. Purity can be measured using any appropriate method such as column chromatography, gel electrophoresis, HPLC, etc. In an embodiment, the tumor antigen peptide is in solution. In another embodiment, the tumor antigen peptide is in solid form, e.g., lyophilized.

In another aspect, the disclosure further provides a nucleic acid (isolated) encoding the herein-mentioned tumor antigen peptides or a tumor antigen precursor-peptide. In an embodiment, the nucleic acid comprises from about 21 nucleotides to about 45 nucleotides, from about 24 to about 45 nucleotides, for example 24, 27, 30, 33, 36, 39, 42 or 45 nucleotides. "Isolated", as used herein, refers to a peptide or nucleic molecule separated from other components that are present in the natural environment of the molecule or a naturally occurring source macromolecule (e.g., including other nucleic acids, proteins, lipids, sugars, etc.). "Synthetic", as used herein, refers to a peptide or nucleic molecule that is not isolated from its natural sources, e.g., which is produced through recombinant technology or using chemical synthesis. A nucleic acid of the disclosure may be used for recombinant expression of the tumor antigen peptide of the disclosure, and may be included in a vector or plasmid, such as a cloning vector or an expression vector, which may be transfected into a host cell. In an embodiment, the disclosure provides a cloning or expression vector or plasmid comprising a nucleic acid sequence encoding the tumor antigen peptide of the disclosure. Alternatively, a nucleic acid encoding a tumor antigen peptide of the disclosure may be incorporated into the genome of the host cell. In either case, the host cell expresses the tumor antigen peptide or protein encoded by the nucleic acid. The term "host cell" as used herein refers not only to the particular subject cell, but to the progeny or potential progeny of such a cell. A host cell can be any prokaryotic (e.g., *E. coli*) or eukaryotic cell (e.g., insect cells, yeast or mammalian cells) capable of expressing the tumor antigen peptides described herein. The vector or plasmid contains the necessary elements for the transcription and translation of the inserted coding sequence, and may contain other components such as resistance genes, cloning sites, etc. Methods that are well known to those skilled in the art may be used to construct expression vectors containing sequences encoding peptides or polypeptides and appropriate transcriptional and translational control/regulatory elements operably linked thereto. These methods include in vitro recombinant DNA techniques, synthetic techniques, and in vivo genetic recombination. Such techniques are described in Sambrook. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y. "Operably linked" refers to a juxtaposition of components, particularly nucleotide sequences, such that the normal function of the components can be performed. Thus, a coding sequence that is operably linked to regulatory sequences refers to a configuration of nucleotide sequences wherein the coding sequences can be expressed under the regulatory control, that is, transcriptional and/or translational control, of the regulatory sequences. "Regulatory/control region" or "regulatory/control sequence", as used herein, refers to the non-coding nucleotide sequences that are involved in the regulation of the expression of a coding nucleic acid. Thus, the term regulatory region includes promoter sequences, regulatory protein binding sites, upstream activator sequences, and the like. In embodiment, the nucleic acid (DNA, RNA) encoding the tumor antigen peptide of the disclosure is comprised or encapsulated within a vesicle, such as a liposome.

In another aspect, the present disclosure provides an MHC class I molecule comprising (i.e. presenting or bound to) a tumor antigen peptide. In an embodiment, the MHC class I molecule is an HLA-A2 molecule, in a further embodiment an HLA-A*02:01 molecule. In an embodiment, the MHC class I molecule is an HLA-A11 molecule, in a further embodiment an HLA-A*11:01 molecule. In an embodiment, the MHC class I molecule is an HLA-A24 molecule, in a further embodiment an HLA-A*24:02 molecule. In another embodiment, the MHC class I molecule is an HLA-B07 molecule, in a further embodiment an HLA-B*07:02 molecule. In another embodiment, the MHC class I molecule is an HLA-B08 molecule, in a further embodiment an HLA-B*08:01 molecule. In another embodiment, the MHC class I molecule is an HLA-B40 molecule, in a further embodiment an HLA-B*40:01. In another embodiment, the MHC class I molecule is an HLA-007 molecule, in a further embodiment an HLA-C*07:01 molecule. In an embodiment, the tumor antigen peptide is non-covalently bound to the MHC class I molecule (i.e., the tumor antigen peptide is loaded into, or non-covalently bound to the peptide binding groove/pocket of the MHC class I molecule). In another embodiment, the tumor antigen peptide is covalently attached/bound to the MHC class I molecule (alpha chain). In such a construct, the tumor antigen peptide and the MHC class I molecule (alpha chain) are produced as a synthetic fusion protein, typically with a short (e.g., 5 to 20 residues, preferably about 8-12, e.g., 10) flexible linker or spacer (e.g., a polyglycine linker). In another aspect, the disclosure provides a nucleic acid encoding a fusion protein comprising a tumor antigen peptide defined herein fused to an MHC class I molecule (alpha chain). In an embodiment, the MHC class I molecule (alpha chain)—peptide complex is multimerized. Accordingly, in another aspect, the present disclosure provides a multimer of MHC class I molecule loaded (covalently or not) with the herein-mentioned tumor antigen peptide. Such multimers may be attached to a tag, for example a fluorescent tag, which allows the detection of the multimers. A great number of strategies have been developed for the production of MHC multimers, including MHC dimers, tetramers, pentamers, octamers, etc. (reviewed in Bakker and Schumacher, *Current Opinion in Immunology* 2005, 17:428-433). MHC multimers are useful, for example, for the detection and purification of antigen-specific T cells. Thus, in another aspect, the present disclosure provides a method for detecting or purifying (isolating, enriching) CD8$^+$ T lymphocytes specific for a tumor antigen peptide defined herein, the method comprising contacting a cell population with a multimer of MHC class I molecule loaded (covalently or not) with the tumor antigen peptide; and detecting or isolating the CD8$^+$ T lymphocytes bound by the MHC class I multimers. CD8$^+$ T lymphocytes bound by the MHC class I multimers may be isolated using known methods, for example fluorescence activated cell sorting (FACS) or magnetic activated cell sorting (MACS).

In yet another aspect, the present disclosure provides a cell (e.g., a host cell), in an embodiment an isolated cell, comprising the herein-mentioned tumor antigen peptide, nucleic acid, vector or plasmid of the disclosure, i.e. a nucleic acid or vector encoding one or more tumor antigen peptides. In another aspect, the present disclosure provides a cell expressing at its surface an MHC class I molecule (e.g., an MHC class I molecule of one of the alleles disclosed above) bound to or presenting a tumor antigen peptide according to the disclosure. In one embodiment, the host cell is a eukaryotic cell, such as a mammalian cell, preferably a human cell. a cell line or an immortalized cell. In another embodiment, the cell is an antigen-presenting cell (APC), such as a dendritic cell (DC) or a monocyte/macropage. In one embodiment, the host cell is a primary cell, a cell line or an immortalized cell. Nucleic acids and vectors can be introduced into cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (supra), and other laboratory manuals. Methods for introducing nucleic acids into mammalian cells in vivo are also known, and may be used to deliver the vector or plasmid of the disclosure to a subject for gene therapy.

Cells such as APCs can be loaded with one or more tumor antigen peptides using a variety of methods known in the art. As used herein "loading a cell" with a tumor antigen peptide means that RNA (mRNA) or DNA encoding the tumor antigen peptide, or the tumor antigen peptide, is transfected into the cells or alternatively that the APC is transformed with a nucleic acid encoding the tumor antigen peptide. The cell can also be loaded by contacting the cell with exogenous tumor antigen peptides that can bind directly to MHC class I molecule present at the cell surface (e.g., peptide-pulsed cells). The tumor antigen peptides may also be fused to a domain or motif that facilitates its presentation by MHC class I molecules, for example to an endoplasmic reticulum (ER) retrieval signal, a C-terminal Lys-Asp-Glu-Leu sequence (see Wang et al., *Eur J Immunol.* 2004 December; 34(12):3582-94).

In another aspect, the present disclosure provides a composition or peptide combination/pool comprising any one of, or any combination of, the tumor antigen peptides defined herein (or a nucleic acid encoding said peptide(s)). In an embodiment, the composition comprises any combination of the tumor antigen peptides defined herein (any combination of 2, 3, 4, 5, 6, 7, 8, 9, 10 or more tumor antigen peptides), or a combination of nucleic acids encoding said tumor antigen peptides. Compositions comprising any combination/sub-combination of the tumor antigen peptides defined herein are encompassed by the present disclosure. In an embodiment, the composition or peptide combination/pool comprises at least 2, 3, 4, 5, 6, 7, 8, 9, 10 of the tumor antigen peptides comprising or consisting of the sequences set forth in SEQ ID NOs: 17-28. In an embodiment, the composition or peptide combination/pool comprises at least 2, 3, 4, 5, 6, 7, 8, 9, 10 of the tumor antigen peptides comprising or consisting of the sequences set forth in SEQ ID NOs: 29-39. In another embodiment, the combination or pool may comprise one or more known tumor antigens.

Thus, in another aspect, the present disclosure provides a composition comprising any one of, or any combination of, the tumor antigen peptides defined herein and a cell expressing a MHC class I molecule (e.g., a MHC class I molecule of one of the alleles disclosed above). APC for use in the present disclosure are not limited to a particular type of cell and include professional APCs such as dendritic cells (DCs), Langerhans cells, macrophages/monocytes and B cells, which are known to present proteinaceous antigens on their cell surface so as to be recognized by CD8$^+$ T lymphocytes. For example, an APC can be obtained by inducing DCs from peripheral blood monocytes and then contacting (stimulating) the tumor antigen peptides, either in vitro, ex vivo or in vivo. APC can also be activated to present a tumor antigen peptide in vivo where one or more of the tumor antigen peptides of the disclosure are administered to a subject and APCs that present a tumor antigen peptide are induced in the body of the subject. The phrase "inducing an APC" or "stimulating an APC" includes contacting or loading a cell with one or more tumor antigen peptides, or nucleic acids encoding the tumor antigen peptides such that the tumor antigen peptides are presented at its surface by MHC class I molecules. As noted herein, according to the present disclosure, the tumor antigen peptides may be loaded indirectly for example using longer peptides/polypeptides comprising the sequence of the tumor antigen peptides (including the native protein), which is then processed (e.g., by proteases) inside the APCs to generate the tumor antigen peptide/MHC class I complexes at the surface of the cells. After loading APCs with tumor antigen peptides and allowing the APCs to present the tumor antigen peptides, the APCs can be administered to a subject as a vaccine. For example, the ex vivo administration can include the steps of: (a) collecting APCs from a first subject, (b) contacting/loading the APCs of step (a) with a tumor antigen peptide to form MHC class I/tumor antigen peptide complexes at the surface of the APCs; and (c) administering the peptide-loaded APCs to a second subject in need for treatment.

The first subject and the second subject may be the same subject (e.g., autologous vaccine), or may be different subjects (e.g., allogeneic vaccine). Alternatively, according to the present disclosure, use of a tumor antigen peptide described herein (or a combination thereof) for manufacturing a composition (e.g., a pharmaceutical composition) for inducing antigen-presenting cells is provided. In addition, the present disclosure provides a method or process for manufacturing a pharmaceutical composition for inducing antigen-presenting cells, wherein the method or the process includes the step of admixing or formulating the tumor antigen peptide, or a combination thereof, with a pharmaceutically acceptable carrier. Cells such as APCs expressing an MHC class I molecule (e.g., an HLA-A2, HLA-A11, HLA-A24, HLA-B07, HLA-B08, HLA-B40 or HLA-007 molecule) loaded with any one of, or any combination of, the tumor antigen peptides defined herein, may be used for stimulating/amplifying CD8$^+$ T lymphocytes, for example autologous CD8$^+$ T lymphocytes. Accordingly, in another aspect, the present disclosure provides a composition comprising any one of, or any combination of, the tumor antigen peptides defined herein (or a nucleic acid or vector encoding same); a cell expressing a MHC class I molecule and a T lymphocyte, more specifically a CD8$^+$ T lymphocyte (e.g., a population of cells comprising CD8$^+$ T lymphocytes).

In an embodiment, the composition further comprises a buffer, an excipient, a carrier, a diluent and/or a medium (e.g., a culture medium). In a further embodiment, the buffer, excipient, carrier, diluent and/or medium is/are pharmaceutically acceptable buffer(s), excipient(s), carrier(s), diluent(s) and/or medium (media). As used herein "pharmaceutically acceptable buffer, excipient, carrier, diluent and/or medium" includes any and all solvents, buffers, binders, lubricants, fillers, thickening agents, disintegrants, plasticizers, coatings, barrier layer formulations, lubricants, stabilizing agent, release-delaying agents, dispersion media, coatings, antibacterial and antifungal agents, isotonic agents, and the like that are physiologically compatible, do not interfere with effectiveness of the biological activity of the active ingredient(s) and that are not toxic to the subject. The use of such media and agents for pharmaceutically active substances is well known in the art (Rowe et al., Handbook of pharmaceutical excipients, 2003, 4$^{th}$ edition, Pharmaceutical Press, London UK). Except insofar as any conventional media or agent is incompatible with the active compound (peptides, cells), use thereof in the compositions of the disclosure is contemplated. In an embodiment, the buffer, excipient, carrier and/or medium is a non-naturally occurring buffer, excipient, carrier and/or medium. In an embodiment, one or more of the tumor antigen peptides defined herein, or the nucleic acids (e.g., mRNAs) encoding said one or more tumor antigen peptides, are comprised within or complexed to a liposome, e.g., a cationic liposome (see, e.g., Vitor M T et al., *Recent Pat Drug Deliv Formul.* 2013 August; 7(2): 99-110).

In another aspect, the present disclosure provides a composition comprising one of more of the any one of, or any combination of, the tumor antigen peptides defined herein (or a nucleic acid encoding said peptide(s)), and a buffer, an excipient, a carrier, a diluent and/or a medium. For compositions comprising cells (e.g., APCs, T lymphocytes), the composition comprises a suitable medium that allows the maintenance of viable cells. Representative examples of such media include saline solution, Earl's Balanced Salt Solution (Life Technologies®) or PlasmaLyte® (Baxter International®). In an embodiment, the composition (e.g., pharmaceutical composition) is an "immunogenic composition", "vaccine composition" or "vaccine". The term "Immunogenic composition", "vaccine composition" or "vaccine" as used herein refers to a composition or formulation comprising one or more tumor antigen peptides or vaccine vector and which is capable of inducing an immune response against the one or more tumor antigen peptides present therein when administered to a subject. Vaccination methods for inducing an immune response in a mammal comprise use of a vaccine or vaccine vector to be administered by any conventional route known in the vaccine field, e.g., via a mucosal (e.g., ocular, intranasal, pulmonary, oral, gastric, intestinal, rectal, vaginal, or urinary tract) surface, via a parenteral (e.g., subcutaneous, intradermal, intramuscular, intravenous, or intraperitoneal) route, or topical administration (e.g., via a transdermal delivery system such as a patch). In an embodiment, the tumor antigen peptide (or a combination thereof) is conjugated to a carrier protein (conjugate vaccine) to increase the immunogenicity of the tumor antigen peptide(s). The present disclosure thus provides a composition (conjugate) comprising a tumor antigen peptide (or a combination thereof) and a carrier protein. For example, the tumor antigen peptide(s) may be conjugated to a Toll-like receptor (TLR) ligand (see, e.g., Zom et al., *Adv Immunol.* 2012, 114: 177-201) or polymers/dendrimers (see, e.g., Liu et al., *Biomacromolecules.* 2013 Aug. 12; 14(8): 2798-806). In an embodiment, the immunogenic composition or vaccine further comprises an adjuvant. "Adjuvant" refers to a substance which, when added to an immunogenic agent such as an antigen (tumor antigen peptides and/or cells according to the present disclosure), nonspecifically enhances or potentiates an immune response to the agent in the host upon exposure to the mixture. Examples of adjuvants currently used in the field of vaccines include (1) mineral salts (aluminum salts such as aluminum phosphate and aluminum hydroxide, calcium phosphate gels), squalene, (2) oil-based adjuvants such as oil emulsions and surfactant based formulations, e.g., MF59 (microfluidised detergent stabilised oil-in-water emulsion), QS21 (purified saponin), AS02 [SBAS2] (oil-in-water emulsion+MPL+QS-21), (3) particulate adjuvants, e.g., virosomes (unilamellar liposomal vehicles incorporating influenza haemagglutinin), ASO4 ([SBAS4] aluminum salt with MPL), ISCOMS (structured complex of saponins and lipids), polylactide co-glycolide (PLG), (4) microbial derivatives (natural and synthetic), e.g., monophosphoryl lipid A (MPL), Detox (MPL+*M. Phlei* cell wall skeleton), AGP [RC-529] (synthetic acylated monosaccharide), DC_Chol (lipoidal immunostimulators able to self-organize into liposomes), OM-174 (lipid A derivative), CpG motifs (synthetic oligonucleotides containing immunostimulatory CpG motifs), modified LT and CT (genetically modified bacterial toxins to provide non-toxic adjuvant effects), (5) endogenous human immunomodulators, e.g., hGM-CSF or hIL-12 (cytokines that can be administered either as protein or plasmid encoded), Immudaptin (C3d tandem array) and/or (6) inert vehicles, such as gold particles, and the like.

In an embodiment, the tumor antigen peptide(s) or composition comprising same is/are in lyophilized form. In another embodiment, the tumor antigen peptide(s) or composition comprising same is/are in a liquid composition. In a further embodiment, the tumor antigen peptide(s) is/are at a concentration of about 0.01 µg/mL to about 100 µg/mL in the composition. In further embodiments, the tumor antigen peptide(s) is/are at a concentration of about 0.2 µg/mL to about 50 µg/mL, about 0.5 µg/mL to about 10, 20, 30, 40 or 50 µg/mL, about 1 µg/mL to about 10 µg/mL, or about 2 µg/mL, in the composition.

As noted herein, cells such as APCs that express an MHC class I molecule loaded with or bound to any one of, or any combination of, the tumor antigen peptides defined herein, may be used for stimulating/amplifying $CD8^+$ T lymphocytes in vivo or ex vivo. Accordingly, in another aspect, the present disclosure provides T cell receptor (TCR) molecules capable of interacting with or binding the herein-mentioned MHC class I molecule/tumor antigen peptide complex, and nucleic acid molecules encoding such TCR molecules, and vectors comprising such nucleic acid molecules. A TCR according to the present disclosure is capable of specifically interacting with or binding a tumor antigen peptide loaded on, or presented by, a MHC class I molecule, preferably at the surface of a living cell in vitro or in vivo. A TCR and in particular nucleic acids encoding a TCR of the disclosure may for instance be applied to genetically transform/modify T lymphocytes (e.g., $CD8^+$ T lymphocytes) or other types of lymphocytes generating new T lymphocyte clones that specifically recognize an MHC class I/tumor antigen peptide complex. In a particular embodiment, T lymphocytes (e.g., $CD8^+$ T lymphocytes) obtained from a patient are transformed to express one or more TCRs that recognize a tumor antigen peptide and the transformed cells are administered to the patient (autologous cell transfusion). In a particular embodiment, T lymphocytes (e.g., $CD8^+$ T lymphocytes) obtained from a donor are transformed to express one or more TCRs that recognize a tumor antigen peptide and the transformed cells are administered to a recipient (allogenic cell transfusion). In another embodiment, the disclosure provides a T lymphocyte e.g., a $CD8^+$ T lymphocyte transformed/transfected by a vector or plasmid encoding a tumor antigen peptide-specific TCR. In a further embodiment the disclosure provides a method of treating a patient with autologous or allogenic cells transformed with a tumor antigen peptide-specific TCR. In yet a further embodiment the use of a tumor antigen-specific TCR in the manufacture of autologous or allogenic cells for the treating of cancer is provided.

In some embodiments, patients treated with the compositions (e.g., pharmaceutical compositions) of the disclosure are treated prior to or following treatment with allogenic stem cell transplant (ASCL), allogenic lymphocyte infusion or autologous lymphocyte infusion. Compositions of the disclosure include: allogenic T lymphocytes (e.g., $CD8^+$ T lymphocyte) activated ex vivo against a tumor antigen peptide; allogenic or autologous APC vaccines loaded with a tumor antigen peptide; tumor antigen peptide vaccines and allogenic or autologous T lymphocytes (e.g., $CD8^+$ T lymphocyte) or lymphocytes transformed with a tumor antigen-specific TCR. The method to provide T lymphocyte clones capable of recognizing a tumor antigen peptide according to the disclosure may be generated for and can be specifically targeted to tumor cells expressing the tumor antigen peptide in a subject (e.g., graft recipient), for example an ASCT and/or donor lymphocyte infusion (DLI) recipient. Hence the disclosure provides a $CD8^+$ T lymphocyte encoding and expressing a T cell receptor capable of specifically recognizing or binding a tumor antigen peptide/MHC class I molecule complex. Said T lymphocyte (e.g., $CD8^+$ T lymphocyte) may be a recombinant (engineered) or a naturally selected T lymphocyte. This specification thus provides at least two methods for producing $CD8^+$ T lymphocytes of the disclosure, comprising the step of bringing undifferentiated lymphocytes into contact with a tumor antigen peptide/MHC class I molecule complex (typically expressed at the surface of cells, such as APCs) under conditions conducive of triggering T cell activation and expansion, which may be done in vitro or in vivo (i.e. in a patient administered with a APC vaccine wherein the APC is loaded with a tumor antigen peptide or in a patient treated with a tumor antigen peptide vaccine). Using a combination or pool of tumor antigen peptides bound to MHC class I molecules, it is possible to generate a population $CD8^+$ T lymphocytes capable of recognizing a plurality of tumor antigen peptides. Alternatively, tumor antigen-specific or targeted T lymphocytes may be produced/generated in vitro or ex vivo by cloning one or more nucleic acids (genes) encoding a TCR (more specifically the alpha and beta chains) that specifically binds to an MHC class I molecule/tumor antigen peptide complex (i.e. engineered or recombinant $CD8^+$ T lymphocytes). Nucleic acids encoding a tumor antigen peptide-specific TCR of the disclosure, may be obtained using methods known in the art from a T lymphocyte activated against a tumor antigen peptide ex vivo (e.g., with an APC loaded with a tumor antigen peptide); or from an individual exhibiting an immune response against peptide/MHC molecule complex. tumor antigen peptide-specific TCRs of the disclosure may be recombinantly expressed in a host cell and/or a host lymphocyte obtained from a graft recipient or graft donor, and optionally differentiated in vitro to provide cytotoxic T lymphocytes (CTLs). The nucleic acid(s) (transgene(s)) encoding the TCR alpha and beta chains may be introduced into a T cells (e.g., from a subject to be treated or another individual) using any suitable methods such as transfection (e.g., electroporation) or transduction (e.g., using viral vector). The engineered $CD8^+$ T lymphocytes expressing a TCR specific for a tumor antigen peptide may be expanded in vitro using well known culturing methods.

The present disclosure provides isolated $CD8^+$ T lymphocytes that are specifically induced, activated and/or amplified (expanded) by a tumor antigen peptide (i.e., a tumor antigen peptide bound to MHC class I molecules expressed at the surface of cell), or a combination of tumor antigen peptides. The present disclosure also provides a composition comprising $CD8^+$ T lymphocytes capable of recognizing a tumor antigen peptide, or a combination thereof, according to the disclosure (i.e., one or more tumor antigen peptides bound to MHC class I molecules) and said tumor antigen peptide(s). In another aspect, the present disclosure provides a cell population or cell culture (e.g., a $CD8^+$ T lymphocyte population) enriched in $CD8^+$ T lymphocytes that specifically recognize one or more MHC class I molecule/tumor antigen peptide complex(es) as described herein. Such enriched population may be obtained by performing an ex vivo expansion of specific T lymphocytes using cells such as APCs that express MHC class I molecules loaded with (e.g. presenting) one or more of the tumor antigen peptides disclosed herein. "Enriched" as used herein means that the proportion of tumor antigen-specific $CD8^+$ T lymphocytes in the population is significantly higher relative to a native population of cells, i.e. which has not been subjected to a step of ex vivo-expansion of specific T lymphocytes. In a further embodiment, the proportion of tumor antigen peptide-specific $CD8^+$ T lymphocytes in the cell population is at least about 0.5%, for example at least about 1%, 1.5%, 2% or 3%. In some embodiments, the proportion of tumor antigen peptide-specific CD8+T lymphocytes in the cell population is about 0.5 to about 10%, about 0.5 to about 8%, about 0.5 to about 5%, about 0.5 to about 4%, about 0.5 to about 3%, about 1% to about 5%, about 1% to about 4%, about 1% to about 3%, about 2% to about 5%, about 2% to about 4%, about 2% to about 3%, about 3% to about 5% or about 3% to about 4%. Such cell population or culture (e.g., a $CD8^+$ T lymphocyte population) enriched in $CD8^+$ T lymphocytes that specifically recognizes one or more MHC class I molecule/peptide (tumor antigen peptide) complex(es) of interest may be used in tumor antigen-based cancer immunotherapy, as detailed below. In some embodiments, the population of tumor antigen peptide-specific CD8+ T lymphocytes is further enriched, for example using affinity-based systems such as multimers of MHC class I molecule loaded (covalently or not) with the tumor antigen peptide(s) defined herein. Thus, the present disclosure provides a purified or isolated population of tumor antigen peptide-specific CD8+ T lymphocytes, e.g., in which the proportion of tumor antigen peptide-specific CD8+ T lymphocytes is at least about 50%, 60%, 70%, 80%, 85%, 90%, 95%, 96%, 97%, 98%, 99% or 100%.

The present disclosure further relates to the use of any tumor antigen peptide, nucleic acid, expression vector, T cell receptor, cell (e.g., T lymphocyte, APC), and/or composition according to the present disclosure, or any combination thereof, as a medicament or in the manufacture of a medicament. In an embodiment, the medicament is for the treatment of cancer, e.g., cancer vaccine. The present disclosure relates to any tumor antigen peptide, nucleic acid, expression vector, T cell receptor, cell (e.g., T lymphocyte, APC), and/or composition (e.g., vaccine composition) according to the present disclosure, or any combination thereof, for use in the treatment of cancer e.g., as a cancer vaccine (e.g., therapeutic cancer vaccine). The tumor antigen peptide sequences identified herein may be used for the production of synthetic peptides suitable i) for in vitro priming and expansion of tumor antigen-specific T cells to be injected into tumor patients and/or ii) as vaccines to induce or boost the anti-tumor T cell response in cancer patients.

In another aspect, the present disclosure provides the use of a tumor antigen peptide described herein, or a combination thereof (e.g. a peptide pool), as a vaccine for treating cancer in a subject. The present disclosure also provides the tumor antigen peptide described herein, or a combination thereof (e.g. a peptide pool), for use as a vaccine for treating cancer in a subject. In an embodiment, the subject is a recipient of tumor antigen peptide-specific CD8+ T lymphocytes. Accordingly, in another aspect, the present disclosure provides a method of treating cancer (e.g., of reducing the number of tumor cells, killing tumor cells), said method comprising administering (infusing) to a subject in need thereof an effective amount of CD8+ T lymphocytes recognizing (i.e. expressing a TCR that binds) one or more MHC class I molecule/tumor antigen peptide complexes (expressed at the surface of a cell such as an APC). In an embodiment, the method further comprises administering an effective amount of the tumor antigen peptide, or a combination thereof, and/or a cell (e.g., an APC such as a dendritic cell) expressing MHC class I molecule(s) loaded with the tumor antigen peptide(s), to said subject after administration/infusion of said CD8+ T lymphocytes. In yet a further embodiment, the method comprises administering to a subject in need thereof a therapeutically effective amount of a dendritic cell loaded with one or more tumor antigen peptides. In yet a further embodiment the method comprises administering to a patient in need thereof a therapeutically effective amount of an allogenic or autologous cell that expresses a recombinant TCR that binds to a tumor antigen peptide presented by an MHC class I molecule.

In another aspect, the present disclosure provides the use of CD8+ T lymphocytes that recognize one or more MHC class I molecules loaded with (presenting) a tumor antigen peptide, or a combination thereof, for treating cancer (e.g., of reducing the number of tumor cells, killing tumor cells) in a subject. In another aspect, the present disclosure provides the use of CD8+ T lymphocytes that recognize one or more MHC class I molecules loaded with (presenting) a tumor antigen peptide, or a combination thereof, for the preparation/manufacture of a medicament for treating cancer (e.g., for reducing the number of tumor cells, killing tumor cells) in a subject. In another aspect, the present disclosure provides CD8+ T lymphocytes (cytotoxic T lymphocytes) that recognize one or more MHC class I molecule(s) loaded with (presenting) a tumor antigen peptide, or a combination thereof, for use in the treatment of cancer (e.g., for reducing the number of tumor cells, killing tumor cells) in a subject. In a further embodiment, the use further comprises the use of an effective amount of a tumor antigen peptide (or a combination thereof), and/or of a cell (e.g., an APC) that expresses one or more MHC class I molecule(s) loaded with (presenting) a tumor antigen peptide, after the use of said tumor antigen peptide-specific CD8+ T lymphocytes.

The present disclosure also provides a method of generating an immune response against tumor cells expressing human class I MHC molecules loaded with any of the tumor antigen peptide disclosed herein or combination thereof in a subject, the method comprising administering cytotoxic T lymphocytes that specifically recognizes the class I MHC molecules loaded with the tumor antigen peptide or combination of tumor antigen peptides. The present disclosure also provides the use of cytotoxic T lymphocytes that specifically recognizes class I MHC molecules loaded with any of the tumor antigen peptide or combination of tumor antigen peptides disclosed herein for generating an immune response against tumor cells expressing the human class I MHC molecules loaded with the tumor antigen peptide or combination thereof.

In an embodiment, the methods or uses described herein further comprise determining the HLA class I alleles expressed by the patient prior to the treatment/use, and administering or using tumor antigen peptides that bind to one or more of the HLA class I alleles expressed by the patient. For example, if it is determined that a patient suffering from B-ALL expresses HLA-A2*01 and HLA-B*08:01, any combinations of the tumor antigen peptides of (i) SEQ ID NOs: 17-19, 27 and/or 28 (that bind to HLA-A2*01), and (ii) SEQ ID NO: 24 or 25 (that binds to HLA-B08*01) may be administered or used in the patient.

In an embodiment, the tumor cells of the cancer to be treated, e.g., leukemia or lung cancer, express one or more of the tumor antigen peptides disclosed herein (SEQ ID NOs: 17-39). In another embodiment, the methods or uses described herein further comprise determining whether the tumor cells from the patient express one or more of the tumor antigen peptides disclosed herein (SEQ ID NOs: 17-39), and administering or using one or more of the tumor antigen peptide(s) expressed by the tumor cells from the patient to treat the cancer.

In an embodiment, the cancer is a blood or hematologic cancer, e.g., leukemia, lymphoma and myeloma. In an embodiment, the cancer is leukemia, including but not limited to acute lymphoblastic leukemia (ALL), acute myeloid leukemia (AML), chronic lymphocytic leukemia (CLL) chronic myeloid leukemia (CML), Hairy cell leukemia (HCL), T-cell prolymphocytic leukemia (T-PLL), Large granular lymphocytic leukemia or Adult T-cell leukemia. In another embodiment, the cancer is lymphoma including but not limited to Hodgkin lymphoma (HL), non-Hodgkin lymphoma (NHL), Burkitt's lymphoma, Precursor T-cell leukemia/lymphoma, Follicular lymphoma, Diffuse large B cell lymphoma, Mantle cell lymphoma, B-cell chronic lymphocytic leukemia/lymphoma or MALT lymphoma. In a further embodiment, the cancer is a B-cell leukemia, such as B-ALL.

In another embodiment, the cancer is a solid cancer, such as lung cancer. In a further embodiment, the lung cancer is non-small cell lung cancer (NSCLC). In an embodiment, the lung cancer is a squamous cell lung cancer (SQCLC), an adenocarcinoma, or a large cell anaplastic carcinoma (LCAC).

In an embodiment, the tumor antigen peptides, nucleic acids, vectors, compositions disclosed herein may be used in combination with other therapies (e.g., anti-tumor therapies), such as chemotherapy, immunotherapy (e.g., CAR T/NK cell-based therapy, checkpoint inhibitor-based therapy, antibody-based therapy), radiotherapy or surgery. Examples of immune checkpoint inhibitors include agents that inhibits PD-1, PD-L1, CTLA-4, KIR, CD40, TIM-3 or LAG-3, such as blocking antibodies. Examples of agents for chemotherapy include, for example, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil (5-FU), gemcitabine, gliadelimplants, hydroxycarbamide, idarubicin, ifosfamide, irinotecan, leucovorin, liposomaldoxorubicin, liposomaldaunorubicin, lomustine, melphalan, mercaptopurine, mesna, methotrexate, mitomycin, mitoxantrone, oxaliplatin, paclitaxel (Taxol), pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Alternatively, the agent for chemotherapy may be a biologic agent, including Herceptin® (trastuzumab) against the HER2 antigen, Avastin® (bevacizumab) against VEGF, or antibodies to the EGF receptor, such as Erbitux® (cetuximab), and Vectibix® (panitumumab). Such additional agents or treatments may be administered/used before, during and/of after the administration/use of the tumor antigen peptides, nucleic acids, vectors, compositions disclosed herein.

Current treatments for ALL typically include vincristine, dexamethasone or prednisone, and an anthracycline drug such as doxorubicin (Adriamycin) or daunorubicin. Allogeneic stem cell transplantation (allo-SCT) is also performed in high-risk patients and patients with relapsed/refractory disease. Other agents under clinical development for the treatment of B-ALL include anti-CD22, anti-CD20 and anti-CD19 antibodies, as well as proteasome inhibitors (Bortezomib), JAK/STAT signaling pathway inhibitors (ruxolitinib), hypomethylating agent (Decitabine) and PI3K/mTOR inhibitors (see, e.g., Terwilliger and Abdul-Hay, *Blood Cancer J.* 2017 June; 7(6): e577).

Current treatments for lung cancer typically include surgery, radiotherapy, chemotherapy with small molecular tyrosine kinase inhibitors (erlotinib, crizotinib) as well as immunotherapy with checkpoint inhibitors such as anti-PD1 antibodies (pembrolizumab) (see, e.g., Dholaria et al., *J Hematol Oncol.* 2016; 9: 138).

MODE(S) FOR CARRYING OUT THE INVENTION

The present invention is illustrated in further details by the following non-limiting examples.

EXAMPLE 1: MATERIALS AND METHODS

Mice. C57BL/6 mice were obtained from the Jackson Laboratory (Bar Harbor, Me.). Mice were housed under specific pathogen-free conditions.

Cell lines. The EL4 T-lymphoblastic lymphoma cell line, the CT26 colorectal cancer cell line and the B-cell hybridoma HB-124 were obtained from the American Type Culture Collection (ATCC). EL4 and CT26 cells were cultured in RPMI 1640/HEPES supplemented with 10% heat-inactivated fetal bovine serum, 1% L-glutamine and 1% penicillin-streptomycin. Cell culture media were further supplemented with 1% non-essential amino acids and 1% sodium-pyruvate or 1% sodium-pyruvate only for EL4 and CT26 cells, respectively. To produce the anti-CDR2 antibody, HB-124 cells were cultured in IMDM supplemented with 10% heat-inactivated fetal bovine serum. Unless stated otherwise, all reagents were purchased from Gibco®.

Human primary samples. Primary leukemic samples (four B-ALL specimens: 07H103, 10H080, 10H118 and 12H018) used in this study were collected and cryopreserved at the Banque de Cellules Leucémiques du Québec (BCLQ) at Hôpital Maisonneuve-Rosemont. Primary leukemic samples were expanded in vivo after transplantation in NSG mice as previously described[1a]. Briefly, 1-2×10$^6$ B-ALL cells were thawed and transplanted via i.v. injection into 8-12 week-old sub-lethally irradiated (250 cGy, 137 Cs-gamma source) NSG mice. Mice were sacrificed at signs of disease and cell suspensions were prepared from mechanically disrupted spleens or, for 07H103, from a mix of splenocytes, bone marrow and peritoneal ascites. From there, Ficoll™ gradients were used to enrich for B-ALL cells prior to MAP isolation (see section MAP isolation). Lung tumor biopsies (Ic2, Ic4 and Ic6) were purchased from Tissue Solutions and homogenized prior to MAP isolation (see section MAP isolation). For all samples, HLA typing was obtained using Optitype version 1.0, running with default parameters for RNA-sequencing (RNA-Seq) data (see section RNA extraction, library preparation and sequencing).

Peptides. Native and $^{13}$C-labelled versions of TSAs were synthesized by GenScript. Purity, as determined by the manufacturer, was greater than 95% and 75% for native and $^{13}$C-labelled peptides, respectively.

Murine mTEC$^{hi}$ extraction. Thymi were isolated from 5-8 week-old C57BL/6 or Balb/c mice and mechanically disrupted to extract thymocytes. Stromal cell enrichment was performed as previously described[2a]. Thymic stromal cells were stained with biotinylated *Ulex europaeus* lectin 1 (UEA1; Vector Laboratories), PE-Cy7—conjugated streptavidin (BD Biosciences), and the following antibodies: Alexa Fluor™ 700 anti-CD45, PE anti—I-Ab (BD Biosciences), allophycocyanin-Cy7 anti-EpCAM (BioLegend). Cell viability was assessed using 7-aminoactinomycin D (7-AAD; BD Biosciences). Live mature mTEC (mTEC$^{hi}$) were gated as 7-AAD$^-$CD45$^-$EpCAM$^+$UEA1$^+$ MHC II$^{hi}$. mTEC$^{hi}$ were sorted on a three-laser FACS Arialllu (BD Biosciences, FIG. 13A).

Human TEC and mTEC extraction. Thymi were obtained from 3-month-old to 7-year-old individuals undergoing corrective cardiovascular surgery (CHU Saint Justine Research Ethic Board, protocol and biobank #2126). Briefly, thymi were kept at 4° C. in 50 ml conical tubes containing media and cut in 2-5 mm cubes within hours following their surgical resection. For long-term preservation, thymic cubes were frozen in cryovials containing heat-inactivated human serum/10% DMSO and kept in liquid nitrogen for a maximum of 3 years.

Cryopreserved thymic samples were transferred on dry ice and used to isolate human TEC and mTEC following a protocol adapted from C. Stoeckle et al.[3a]. Thymic tissue was cut into small fragments, then digested at 37° C. using a solution of 2 mg/mL Collagenase A (Roche) and 0.1 mg DNase I/ml (Sigma-Aldrich) in RPMI-1640 (Gibco) for three to five periods of 40 min. After the second digestion, a solution of Trypsin/EDTA (Gibco) was added, for which the activity was neutralized by adding FBS (Invitrogen) 15 min before the end of incubation. For TEC and mTEC sorting (FIG. 13B), cell suspensions were stained with Pacific blue-conjugated anti-CD45 (BioLegend), PE-conjugated anti-HLA-DR (BioLegend), APC-conjugated anti-EpCAM (BioLegend), Alexa 488-conjugated anti-CDR2 (produced with the HB-124 hybridoma—see section Cell lines— and conjugated with the Dylight 488 Fast conjugation kit from Abcam, only for mTEC samples) and cell viability was assessed using 7-AAD (BD Biosciences).

RNA extraction, library preparation and sequencing. For EL4 and CT26 cells, one replicate of 5×10$^6$ cells was used to perform RNA-sequencing. For C57BL/6 and Balb/c mTEC$^{hi}$, RNA-sequencing was performed in triplicate on a minimum of 31,686 or 16,338 FACS-sorted cells extracted from 2 females and 2 males. For primary leukemic cells, RNA-Seq was performed on a single replicate of 2.0 to 4.0×10$^6$ cells. For human TEC and mTEC, one RNA-Seq replicate per donor were performed with 33,076 to 84,198 FACS-sorted TECs or 50,058 to 100,719 mTECs. In all cases, total RNA was isolated using TRIzol (Invitrogen), further purified using the RNeasy kit or RNeasy micro kit (Qiagen) as recommended by each manufacturer. For each lung tumor biopsy (three in total), total RNA was isolated from ~30 mg of tissues using the AllPrep DNA/RNA/miRNA Universal kit (Qiagen) as recommended by the manufacturer and was used to perform one replicate of RNA-Seq per sample. Each murine sample (EL4, CT26 and murine mTEC$^{hi}$) were quantified on a Nanodrop 2000 (Thermo Fisher Scientific) and RNA quality was assessed on a 2100 Bioanalyzer (Agilent Genomics) in order to select samples with an RNA integrity number ≥9. For human samples (B-ALLs, lung tumor biopsies and human TEC/mTEC), quantification of total RNA was made by QuBit (ABI) and quality of total RNA was assessed with the 2100 BioAnalyzer (Agilent Genomics) in order to select samples with an RNA integrity number ≥7. cDNA libraries were prepared from 2-4 μg for EL4 and CT26 cells, 50-100 ng for murine mTEC$^{hi}$, 500 ng for B-ALLs specimens, 4 μg for lung tumor biopsies, 8-13 ng for human TECs or 41-68 ng for human mTECs of total RNA using the TruSeq Stranded Total RNA Library Prep Kit (EL4 cells), KAPA Stranded mRNA-Seq Kit (CT26 cells, C57BL/6 mTEC', human mTEC, lung tumors and B-ALL specimens) or KAPA RNA HyperPrep Kit (Balb/c mTEC$^{hi}$, human TEC). These libraries were further amplified by 9-16 cycles of PCR before sequencing. Paired-end RNA-sequencing was performed on an Illumina NextSeg™ 500 (Balb/c mTEC$^{hi}$, human TEC and mTEC) or HiSeg™ 2000 (any other sample) and yielded an average of 175 and 199×10$^6$ reads per murine and human sample, respectively.

Generation of canonical cancer and normal proteomes. For all samples, RNA-Seq reads were trimmed for sequencing adapters and low quality 3' bases using Trimmomatic version 0.35 and then aligned to the reference genome, GRCm38.87 for murine samples and GRCh38.88 for human samples, using STAR version 2.5.1b[4a] running with default parameters except for—alignSJoverhangMin,—alignMatesGapMax,—alignIntronMax, and —alignSJstitchMismatchNmax parameters for which default values were replaced by 10, 200,000, 200,000 and 5-1 5 5, respectively. Single-base mutations with a minimum alternate count setting of 5 were identified using freeBayes version 1.0.2-16-gd466dde [arXiv:1207.3907] and exported in a VCF, which was converted to an agnostic SNP file format compatible with pyGeno[5a]. Finally, transcript expression was quantified in transcripts per million (tpm) with kallisto version 0.43.1 [Nicolas L Bray, Harold Pimentel, Páll Melsted and Lior Pachter, Near-optimal probabilistic RNA-seq quantification, Nature Biotechnology 34, 525-527 (2016)] running with default parameters. Of note, kallisto index was constructed using the index functionality and using the appropriate *.cdna.all.fa.gz files downloaded from Ensembl. To build each sample's canonical proteome, pyGeno was used to (i) insert high-quality sample-specific single-base mutations (freeB ayes quality >20) in the reference genome, thereby creating a personalized exome, and to (ii) export sample-specific sequence(s) of known proteins generated by expressed transcripts (tpm>0). These protein sequences were written to a fasta file that was subsequently used for mass spectrometry (MS) database searches (Cancer canonical proteome) and/or MHC I-associated peptide (MAP) classification (Cancer and normal canonical proteome). See FIG. 1B for a schematic and Tables 4a-b for statistics.

Generation of cancer and normal k-mer databases. For all cancer and normal samples, both R1 and R2 fastq files were independently downloaded and trimmed for sequencing adapters and low quality 3' bases using Trimmomatic version 0.35. To ensure that all reads were on the transcript-encoding strand, R1 reads were reverse-complemented using using the fastx_reverse_complement function of the FASTX-Toolkit version 0.0.14. Using jellyfish 2.2.3[6a], 33 and 24 nucleotide-long k-mer databases that were used for k-mer profiling and MAP classification, respectively, were generated (see FIG. 7A for details). Of note, when multiple biological replicates (murine mTEC$^{hi}$) or when multiple samples from unrelated donors (human TEC and mTEC) were available, fastq files were concatenated to generate a single normal k-mer database per condition (C57BL/6, Balb/c or human).

k-mer filtering and generation of cancer-specific proteomes. To extract 33 nucleotide-long k-mers that could give rise to TSAs, the analysis was restricted to k-mers seen at least 4 times in the EL4 or CT26 k-mer cells, 7 times in lung tumor biopsies and 10 times in primary leukemic samples. Cancer-specific k-mers were then obtained by selecting those that were not expressed in the relevant mTEC$^{hi}$ or human TEC/mTEC k-mer database (see FIG. 7B). This cancer-specific k-mer set was further assembled into longer linear sequences, called contigs. Briefly, one of the submitted 33-nucleotide-long k-mer is randomly selected to be used as a seed that is then extended from both ends with consecutive k-mers overlapping by 32 nucleotides on the same strand (-r option disabled, as stranded sets of k-mers were used). The assembly process stops when either no k-mers can be assembled, i.e., no 32-nucleotide-overlapping k-mer can be found, or when more than one k-mer fits (-a 1 option for linear assembly). If so, a new seed is selected and the assembly process resumes until all k-mers from the submitted list have been used once (see FIG. 7C). This step is done by the kmer_assembly function of an in-house developed software called NEKTAR. To obtain proteins, 3-frame translation of contigs that were at least 34 nucleotide-long was performed using an in-house python script. Cancer-specific proteins were then split at internal stop codons and any resulting subsequence of at least 8 amino acid-long was given a unique ID before being included in the relevant database (see FIG. 7D). See FIG. 1B for schematic and Tables 4a-b for statistics.

MAP isolation. For EL4 and CT26 cells, three biological replicates of $250 \times 10^6$ exponentially growing cells were prepared from exponentially growing cells. For all primary leukemic samples, three biological replicates of ~450 to $700 \times 10^6$ cells were prepared from freshly harvested leukemic cells (see section Human primary samples). MAPs were obtained as previously described[7a], with minor modifications: following mild acid elution (MAE), peptides were desalted on an Oasis HLB cartridge (30 mg, Waters) and filtered on a 3 kDa molecular weight cut-off (Amicon Ultra-4, Millipore) to remove β2-microglobulin ($\beta_2 M$) proteins. For one of the primary leukemic samples (specimen 10H080), four additional replicates of $100 \times 10^6$ cells were prepared and MAPs were isolated by immunoprecipitation (IP) as previously described[1a]. Finally, lung tumor biopsies (wet weight ranging from 771 to 1,825 mg, see section Human primary samples) were cut in small pieces (cubes of ~3 mm in size) and 5 ml of ice-cold PBS containing protein inhibitor cocktail (Sigma) was added to each tissue sample. Tissues were first homogenized twice using an Ultra Turrax T25 homogenizer (20 seconds at 20,000 rpm, IKA-Labortechnik) and then once using an Ultra Turrax T8 homogenizer (20 seconds at 25,000 rpm, IKA-Labortechnik). Then, 550 µl of ice-cold 10× lysis buffer (10% w/v CHAPS) was added to each sample and MAPs were immunoprecipitated as previously described[1] using 1 mg (1 ml) of covalently cross-linked W6/32 antibody to protein A magnetic beads per sample. Regardless of the MAP isolation technique, MAP extracts were all dried using a Speed-Vac and kept frozen prior to MS analyses.

Mass spectrometry analyses. Dried MAP extracts were all re-suspended in 0.2% formic acid. For EL4 and CT26, MAP extracts were loaded on a home-made C18 pre-column (5 mm×360 µm i.d. packed with 018 Jupiter Phenomenex) and separated on a home-made 018 analytical column (15 cm×150 µm i.d. packed with 018 Jupiter Phenomenex) with a 56-min gradient from 0-40% acetonitrile (0.2% formic acid) and a 600 nl.min$^{-1}$ flow rate on a nEasy-LC II system. For all human samples, MAP extracts were loaded on a home-made 018 analytical column (15 cm×150 µm i.d. packed with 018 Jupiter Phenomenex) with a 56-min gradient from 0-40% acetonitrile (0.2% formic acid, 07H103, 10H080-MAE, 10H118 and 12H018) or with a 100-min gradient from 5-28% acetonitrile (0.2% formic acid, lung tumor biopsies and 10H080-IP) and a 600 nl·min-1 flow rate on a nEasy-LC II system. Samples were analyzed with a Q-Exactive Plus (EL4, Thermo Fisher Scientific) or HF (all other samples, Thermo Fisher Scientific). For the Q-Exactive Plus, each full MS spectrum, acquired with a 70,000 resolution, was followed by 12 MS/MS spectra, where the most abundant multiply charged ions were selected for MS/MS sequencing with a resolution of 17,500, an automatic gain control target of 1e6, an injection time of 50 ms and a collision energy of 25%. For the Q-Exactive HF, each full MS spectrum, acquired with a 60,000 resolution, was followed by 20 MS/MS spectra, where the most abundant multiply charged ions were selected for MS/MS sequencing with a resolution of 15,000 (CT26, 07H103, 10H080-MAE, 10H118, 12H018) or 30,000 (lung tumor biopsies, 10H080-IP), an automatic gain control target of $5 \times 10^4$, an injection time of 100 ms and a collision energy of 25%. Peptides were identified using Peaks 8.5 (Bioinformatics Solution Inc.) and peptide sequences were searched against the relevant global cancer database, obtained by concatenating the canonical cancer proteome and cancer-specific proteome (see sections *Generation of canonical cancer and normal proteomes and k-mer filtering and generation of cancer-specific proteomes*). For peptide identification, tolerance was set at 10 ppm and 0.01 Da for precursor and fragment ions, respectively. Occurrence of oxidation (M) and deamidation (NQ) were considered as post-translational modifications.

Identification of MAPs. To select for MAPs, lists of unique identifications obtained from Peaks were filtered to include 8 to 11 amino acid-long peptides that had a percentile rank 2% as predicted by NetMHC 4.0[8a] for at least one on the relevant MHC I molecules. Moreover, a local 5% false discovery rate (FDR), defined as the number of decoy identifications divided by the number of target identifications above a given Peaks score threshold, was applied in order to limit the number of false positive identifications in the final MAP lists.

Identification and validation of TSA candidates. To identify TSA candidates among all identified MAPs, an immunogenic status was assigned to each pair of MAP/protein. To do so, each MAP and its associated MAP-coding sequence(s) (MCS) were queried to the relevant cancer and normal personalized proteome or cancer and normal 24 nucleotide-long k-mer databases, respectively. MAPs detected in the normal canonical proteome were excluded regardless of their MCS detection status, as they are likely to be tolerogenic. MAPs that were truly cancer-specific, i.e., no detection in the normal canonical proteome nor in normal k-mers, were flagged as TSA candidates. MAPs absent from both canonical proteomes but present in both k-mer databases needed to have their MCS overexpressed by at least 10-fold in cancer cells, with regard to normal cells, in order to be flagged as such (see FIG. 8A). Finally, MAPs encoded by several MCS (from different proteins) could only be flagged as TSA candidate if their respective MCSs were concordant, i.e. if consistently flagged this MAP as a TSA candidate. MS/MS spectra of all TSA candidates were manually inspected to remove any spurious identifications. Besides, sequences presenting with multiple genomically possible I/L variants were further inspected to report both variants when they were distinguishable by MS, or only the most expressed variant when they were not (see FIG. 8B). Finally, a genomic location was assigned to all those MS-validated TSA candidates by mapping MCS-containing reads on the reference genome (GRCm38.87 or GRCh38.88) using BLAT (tool from the UCSC genome browser). TSA candidates for which reads did not match to a concordant genomic location or matched to hypervariable regions (such as the MHC, Ig or TCR genes) or multiple genes were excluded. For those with a concordant genomic location, Integrative Genome Viewer (IGV)[9a] was used to exclude TSA candidates with an MCS overlapping synonymous mutations with regard to their relevant normal counterpart or, for human TSA candidates, those overlapping a known germline polymorphism (i.e., listed in dbSNP v. 149, FIG. 8C). Remaining peptides were classified as mTSAs or aeTSA candidates, depending if their MCS overlapped a cancer-specific mutation or not.

Peripheral expression of MCS. To assess the peripheral expression of TAAs' and aeTSA candidates' MCS, RNA-Seq data from (1) 22 murine tissues for which the RNA had been sequenced by the ENCODE consortium[10a,11a] (Table 5) or (2) 28 peripheral human tissues (~50 donors per tissue), which had been sequenced by the GTEx consortium and downloaded from the GTEx Portal on Apr. 16, 2018 (phs000424.v7.p2, Table 6), was used. Briefly, RNA-sequencing data from each tissue were transformed into 24 nucleotide-long k-mer databases with Jellyfish 2.2.3 (using the −C option) and used to query each MCS's 24 nucleotide-long k-mer set. For each RNA-Seq experiment, the number of reads fully overlapping a given MCS ($r_{overlap}$) was estimated using the k-mer set's minimum occurrence ($k_{min}$). Indeed, it was hypothesized that $k_{min} \sim r_{overlap}$ because, except for low complexity RNA-Seq reads that might generate the same k-mer multiple times, one k-mer always originate from a single RNA-Seq read. Thus, to compare the MCS expression level across all tissues, this $r_{overlap}$ value was transformed into a number of reads detected per $10^8$ reads sequenced ($r_{phm}$) using the following formula: rphm= ($r_{overlap} \times 10^8 / r_{tot}$, with $r_{tot}$ representing the total number of reads sequenced in a given RNA-Seq experiment. Such values were then log-transformed ($\log_{10}(\text{rphm}+1)$) and averaged across all RNA-Seq experiments of a given tissue. aeTSA candidates exhibiting a peripheral expression in 10 or less tissues (at rphm>0) or in less than 5 tissues other than the liver (at rphm>15) for murine and human candidates respectively, were considered as genuine aeTSAs. Features of those aeTSAs, as well as mTSAs are reported in Tables 1a-b, 2a-d and 3a-c.

MS validation of TSA candidates. For CT26 TSA candidates and two EL4 TSA candidates (ATQQFQQL—SEQ ID NO:11 and SSPRGSSTL—SEQ ID NO:13), the previously acquired MS/MS spectra was compared to the relevant $^{12}$C-analog. For the other five EL4 TSA candidates tested in vivo (IILEFHSL—SEQ ID NO:12, TVPLNHNTL—SEQ ID NO:14, VNYIHRNV—SEQ ID NO:15, VNYLHRNV—SEQ ID NO:15, VTPVYQHL—SEQ ID NO:16), MAPs from six additional EL4 replicates (~450 to 1,400×10$^6$ cells per replicate) were eluted and all processed as previously described (see Section MAP isolation and Mass spectrometry analyses). For absolute quantification, three of the six EL4 replicates were spiked with 500 fmol of each $^{13}$C-labelled TSA. For sequence validation, MS/MS spectrum of $^{12}$C TSA candidates were acquired prior to sample analysis by PRM MS. Briefly, the PRM acquisition, which monitored five peptides as scheduled (each peptide is only monitored in a 10-minute window centered on its elution time), consisted of one MS1 scan followed by the targeted MS/MS scans in HCD mode. Automatic gain controls and injection times for the survey scan and the tandem mass spectra were 3e6-50 ms and 2e5-100 ms, respectively. In all cases, Skyline$^{12a}$ was used to extract the endogenous MS/MS spectrum of each TSA candidate and compare it to the relevant $^{12}$C MS/MS spectrum (sequence validation) or to extract the intensity of the endogenous and the relevant synthetic $^{13}$C-labelled peptide (absolute quantification). Using the following formula, these intensities were further used to compute the number of TSA copy per cell for each replicate: ($n_{synthetic} \times I_{endogenous} \times N_A / I_{synthetic}) \times (1/N_{cells})$ with $n_{synthetic}$, initial number of moles spiked for the considered synthetic $^{13}$C-labelled TSA; $I_{endogenous}$ and $I_{synthetic}$, intensity of the relevant endogenous and $^{13}$C-labelled TSA, respectively; $N_A$, Avogadro's number; $N_{cells}$, initial number of cells used for mild acid elution.

Cumulative number of transcripts detected in human TEC and mTEC samples. Restricting the analysis to transcripts expressed at a tpm>1 in at least one of the six samples (2 TECs and 6 mTECs), Spearman's rank correlation coefficient was computed for each 1-to-1 TEC/mTEC comparison. Then, using those same sets of expressed transcripts, the cumulative numbers of transcripts (cT) detected was computed as each additional sample was analyzed. Because the order in which samples are introduced in the analysis can influence cT values, the cT values across all sample permutations was averaged and those average data points were used to fit the following predictive curve (with the R's 'nls' function):

$$cT = \frac{a(nS-1)}{[b+(nS-1)]} + c,$$

with cT, the cumulative numbers of transcripts and nS, the number of analyzed samples. This equation was then used to extrapolate the number of transcripts that would have been detected by studying up to 20 samples and which can be estimated by simply computing $$\lim_{nS \to \infty} (cT).$$

Generation of bone marrow-derived dendritic cells (DCs), mouse immunization and EL4 cell injection. Bone marrow—derived DCs were generated as previously described[13a,14a]. For mouse immunization, DCs from male C57BL/6 mice were pulsed with 2 µM of the selected peptide for 3 hours, then washed. 8- to 12-week old female C57BL/6 mice were injected i.v. with 10$^6$ individually peptide-pulsed DCs at day −14 and −7, or with irradiated EL4 cells (10,000 cGy). As negative control, C57BL/6 female mice were immunized with unpulsed DCs. At day 0 and day 150, mice were injected i.v. with 5×10$^5$ EL4 cells and were monitored for weight loss, paralysis, or tumor outgrowth.

IFN-γ ELISpot and avidity assays. ELISpot and avidity assays were performed as previously described[14]a. Briefly, Millipore MultiScreen PVDF plates were permeabilized with 35% ethanol, washed, and coated overnight using the Mouse IFN-γ ELISpot Ready-SET-Go! reagent set (eBioscience). At day 0 following mice immunization, splenocytes were harvested from immunized or naive mice. 30×10$^6$ splenocytes/mL were stained with FITC-conjugated anti-CD8a (BD Biosciences) for 30 minutes at 4° C., washed, and sorted using a FACSAria™ IIu or a FACSAria™ IIIu apparatus (BD Biosciences, FIG. 13C). Sorted CD8$^+$ T cells were plated and incubated at 37° C. for 48 hours in the presence of irradiated splenocytes (4,000 cGy) from syngeneic mice pulsed with the relevant peptide (4 µM for the ELISpot assay and 10$^{-4}$ to 10$^{-14}$ M for the avidity assay). As a negative control, CD8$^+$ T cells from naive mice were incubated with peptide-pulsed splenocytes. Spots were revealed using the reagent set manufacturer protocol and were enumerated using an ImmunoSpot S5 UV Analyzer (Cellular Technology Ltd). IFN-γ production was expressed as the number of spot-forming units per 10$^6$ CD8$^+$ T cells and the EC$_{50}$ was calculated using a dose-response curve.

Cell isolation from lymphoid tissue and tetramer-based enrichment protocol. The spleen and inguinal, axillary, brachial, cervical and mesenteric lymph nodes were harvested from C57BL/6 mice. Single-cell suspensions were stained with Fc block and 10 nM of PE- or APC-labeled pMHC I tetramers (NIH Tetramer Core Facility) for 30 minutes at 4° C. After washing with ice-cold sorting buffer (PBS with 2% FBS), cells were resuspended in 200 µL of sorting buffer and 50 µL of anti-PE and/or anti-APC antibody conjugated magnetic microbeads (Miltenyi Biotech), then incubated for 20 minutes at 4° C. Cells were then washed and tetramer$^+$ cells were magnetically enriched as previously described[18a,18a]. The resulting tetramer-enriched fractions were stained with APC Fire 750-conjugated anti-B220, F4/80, CD19, CD11b, CD11c (BioLegend), PerCP-conjugated anti-CD4 (BioLegend), BV421-conjugated anti-CD3 (BD Biosciences), BB515-conjugated anti-CD8 (BD Biosciences), BV510-conjugated anti-CD44 (BD Biosciences) antibodies and Zombie NIR Fixable Viability Kit (BioLegend). Anti-CD11b and CD11c were left out for the analysis of post-immunization repertoires because these markers may be expressed by some activated T cells[17a,18a]. The entire stained sample was then analyzed on a FACSCanto™ II cytometer (BD Biosciences) and fluorescent counting beads (Thermo Fisher Scientific) were used to normalize the results. As negative control, the antigen-specific CD8$^+$T-cell repertoires targeting 3 virus-derived antigens was enriched: gp-33 from the lymphocytic choriomeningitis virus (LCMV) protein gp-33 (KAVYNFATC—SEQ ID NO:40; H-2db), M45 from the murine cytomegalovirus protein M45 (HGIRNASFI—SEQ ID NO:41; H-2db) and B8R from the vaccinia virus protein B8R (TSYKFESV—SEQ ID NO:42; H-2Kb).

Figure 1A:
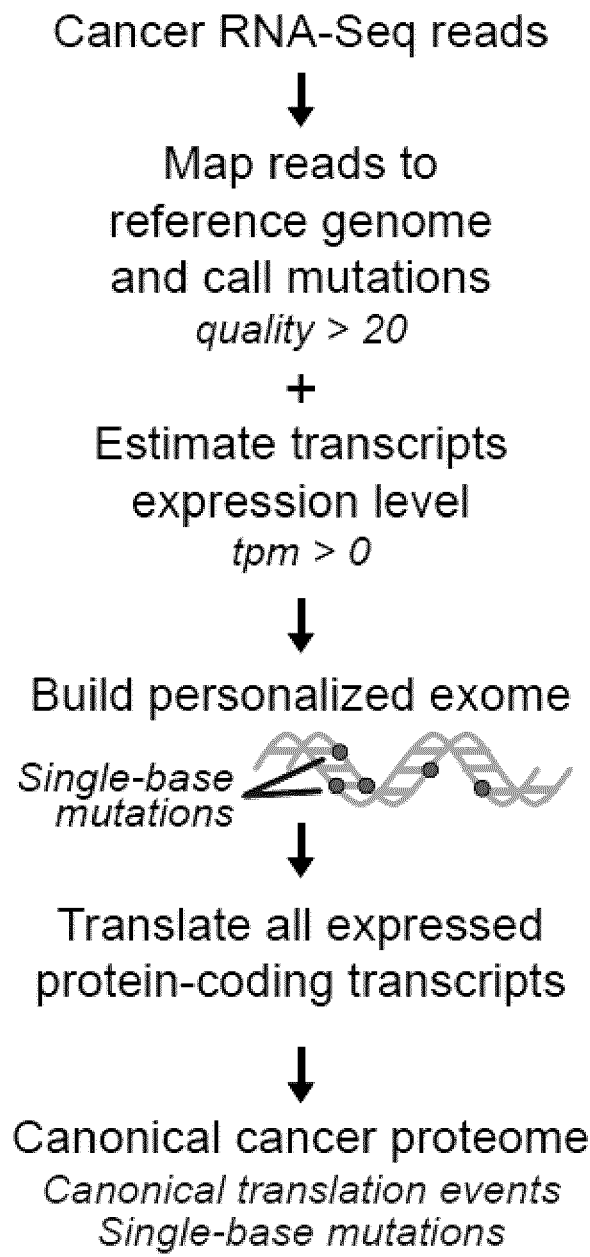
FIGS. 1A-C show the targeted proteogenomic workflow for the identification of tumor-specific antigens (TSAs).

Data. Information regarding all samples used in this study are listed in Table 7. Sequencing and expression data used in FIG. 1 have been deposited to the NCBI's Sequence Read Archive and GEO which can both be accessed from GEO under the SuperSeries accession code GSE113992, containing the GSE111092 and the GSE113972 accession code for murine or human sequencing and expression data, respectively. MS raw data and associated databases used in FIG. 1 have been deposited to the ProteomeXchange Consortium via the PRIDE[19a] partner repository with the following dataset identifier: PXD009065 and 10.6019/PXD009065 (CT26 cell line), PXD009064 and 10.6019/PXD009064 (EL4 cell line), PXD009749 and 10.6019/PXD009749 (07H103), PXD009753 and 10.6019/PXD009753 (10H080, mild acid elution), PXD007935—assay #81756 and 10.6019/PXD007935 (10H080, immunoprecipitation)[1a], PXD009750 and 10.6019/PXD009750 (10H118), PXD009751 and 10.6019/PXD009751 (12H018), PXD009752 and 10.6019/PXD009752 (1c2), PXD009754 and 10.6019/PXD009754 (1c4) and PXD009755 and 10.6019/PXD009755 (1c6).

EXAMPLE 2: RATIONALE AND DESIGN OF A PROTEOGENOMIC METHOD FOR TSA DISCOVERY

Figure 1B:
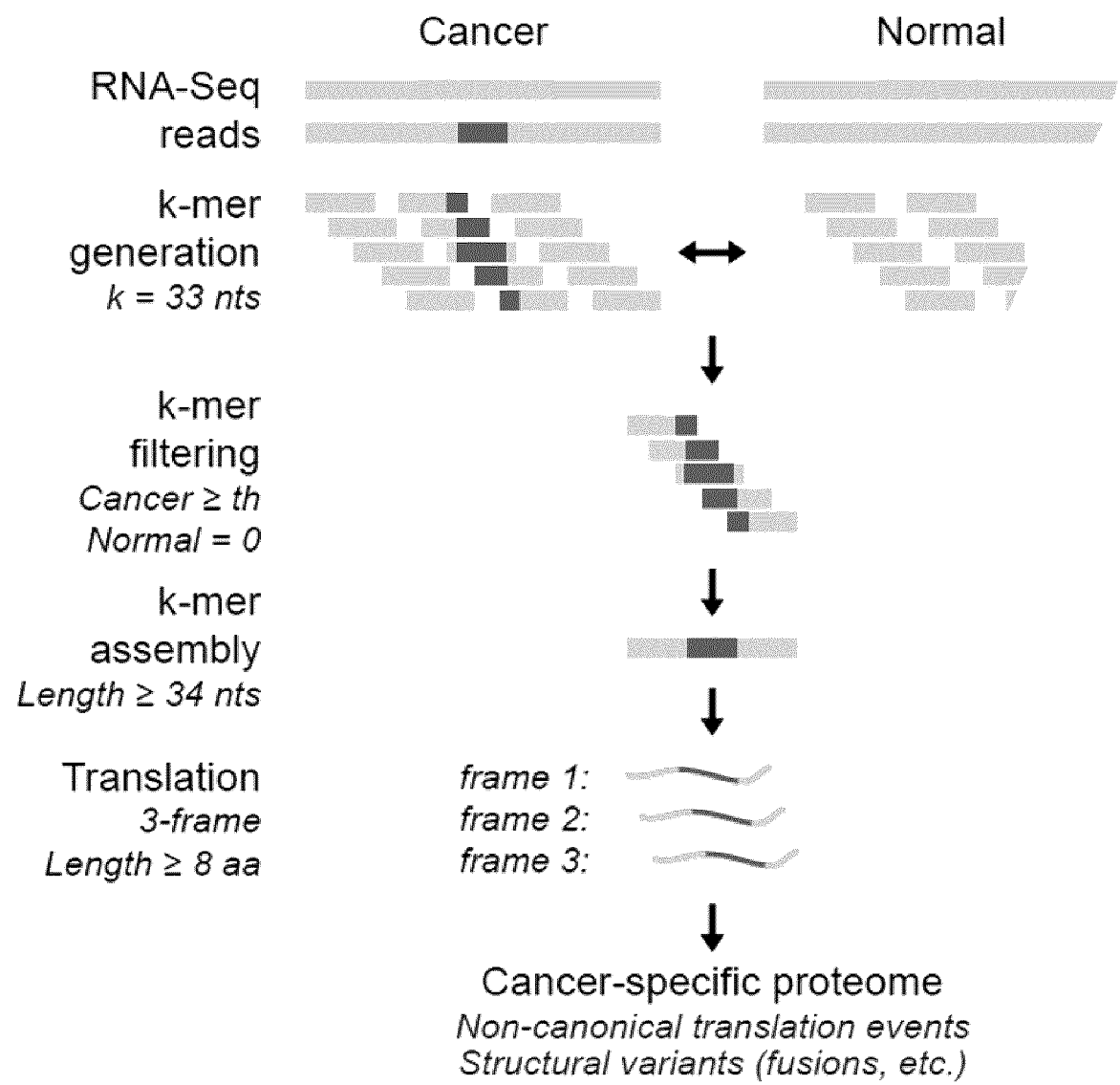
Figure 1C:
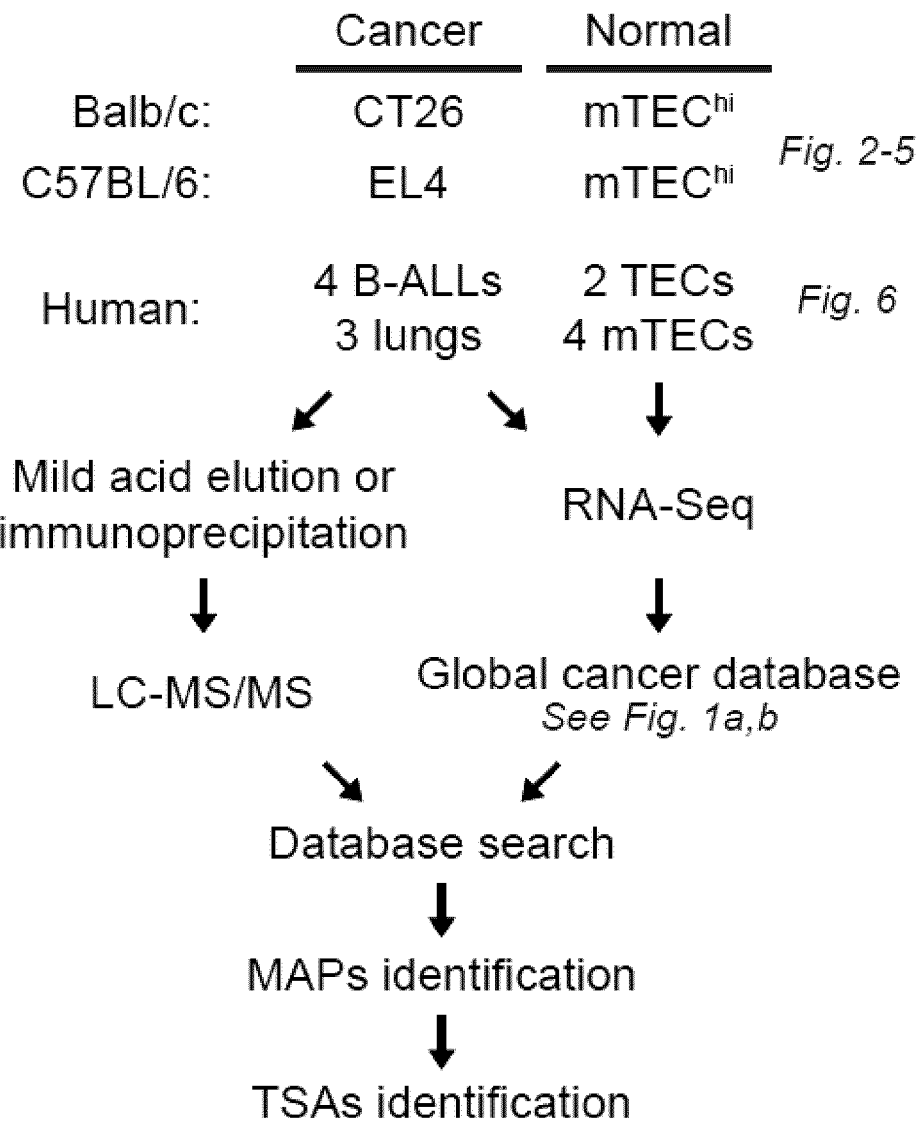

Attempts to computationally predict TSAs using various algorithms are fraught with exceedingly high false discovery rates[27]. Hence, systems-level molecular definition of the MAP repertoire can only be achieved by high-throughput MS studies[3]. Current approaches use MS/MS software tools, such as Peaks[28], which rely on a user-defined protein database to match each acquired MS/MS spectrum to a peptide sequence. Since the reference proteome does not contain TSAs, MS-based TSA discovery workflows must use proteogenomic strategies to build customized databases, derived from tumor RNA-sequencing (RNA-Seq) data[29], that should ideally contain all proteins, even unannotated ones, expressed in the considered tumor sample. As current MS/MS software tools cannot deal with the large search space created by all-frame translating all RNA-Seq reads[30,31], a proteogenomic strategy enriching for cancer-specific sequences was devised in order to comprehensively characterize the landscape of TSAs coded by all genomic regions. The resulting database, termed global cancer database, is composed of two customizable parts. The first part, referred to as the canonical cancer proteome (FIG. 1A), was obtained by in silico translation of expressed protein-coding transcripts in their canonical frame; it therefore contains proteins coded by exonic sequences that are normal or contain single-base mutations. The second part, referred to as the cancer-specific proteome (FIG. 1B), was generated using an alignment-free RNA-Seq workflow, called k-mer profiling, because current mappers and variant callers poorly identify structural variants. This second dataset enabled the detection of peptides encoded by any reading frame of any genomic origin (including structural variants), as long as they were cancer-specific (i.e., absent from normal cells). Here, it was elected to use mTEChi as a "normal control" because they express most known genes and induce central tolerance to MAPs coded by their vast transcriptome[32]. Thus, to identify RNA sequences that were cancer-specific, cancer RNA-Seq reads were chopped into 33-nucleotide-long sequences, called k-mers[33], from which k-mers were removed from syngeneic mTEChi (FIGS. 7A-B). Redundancy inherent to the k-mer space was removed by assembling overlapping cancer specific k-mers into longer sequences, called contigs, which were further in silico 3-frame translated (FIG. 1B and FIGS. 7C-D). The canonical cancer proteome and the cancer-specific proteome were then concatenated to create a global cancer database, one for each analyzed sample. Using such optimized databases, MAPs eluted from two well-characterized mouse tumor cell lines, namely CT26, a colorectal carcinoma from a Balb/c mouse and EL4, a T-lymphoblastic lymphoma from a C57BL/6 mouse that were sequenced by MS were identified (FIG. 1C).

EXAMPLE 3: NON-CODING REGIONS ARE THE MAIN SOURCE OF TSAS

Figure 2A:
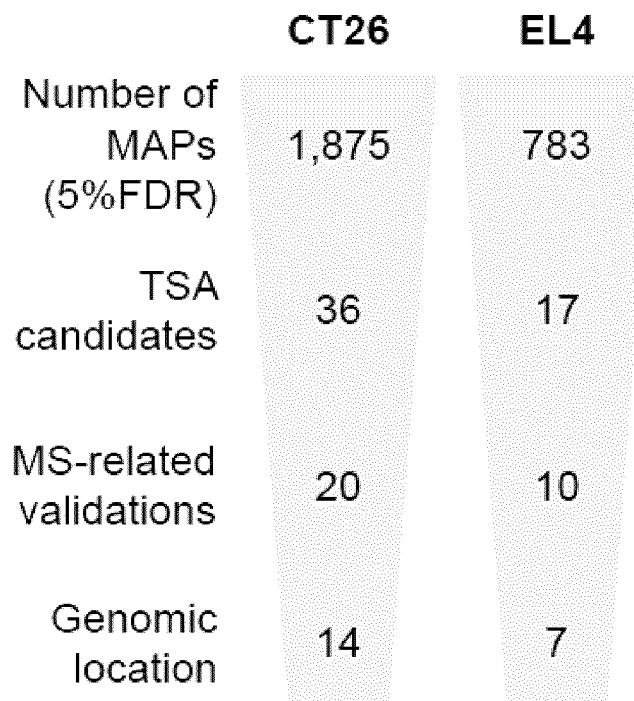
FIGS. 2A-D depict results of experiments showing that most TSAs derive from the translation of non-coding regions.
Figure 2B:
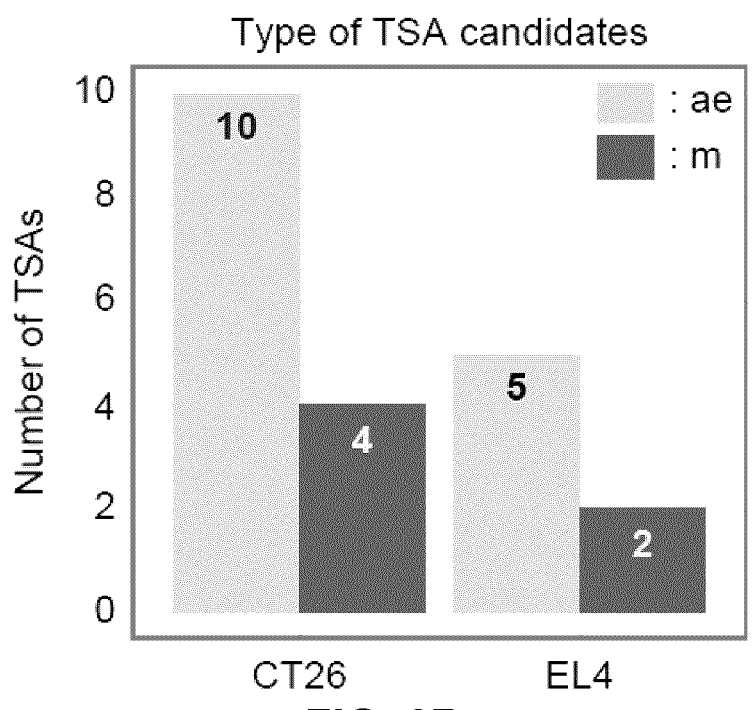

At 5% false discovery rate, 1,875 MAPs on CT26 cells and 783 MAPs on EL4 cells were identified. Among those, MAPs absent from the mTEC$^{hi}$ proteome were considered as TSAs candidates if (i) their 33-nucleotide-long MAP-coding sequence (MCS), derived from a full cancer-restricted 33-nucleotide-long k-mers, was absent from the mTEChi transcriptome or if (ii) their 24-to-30-nucleotide-long MCS, derived from a truncated version of a cancer restricted 33-nucleotide-long k-mers, was overexpressed by at least 10-fold in the transcriptome of cancer vs. mTEC$^{hi}$ cells (FIG. 8A). Following MS-related validation steps and assignment of a genomic location (FIG. 8B-C), a total of 6 mTSAs and 15 aeTSA candidates were obtained: 14 presented by CT26 cells and 7 by EL4 cells (FIG. 2A-B). MAPs that were both mutated and aberrantly expressed were included in the mTSA category. All these MAPs are believed to be novel and are absent from the Immune Epitope Database[36], except for one: the AH1 peptide (SPSYVYHQF), the sole 150 aeTSA previously identified on CT26 cells using reverse immunology[9,37].

Figure 2C:
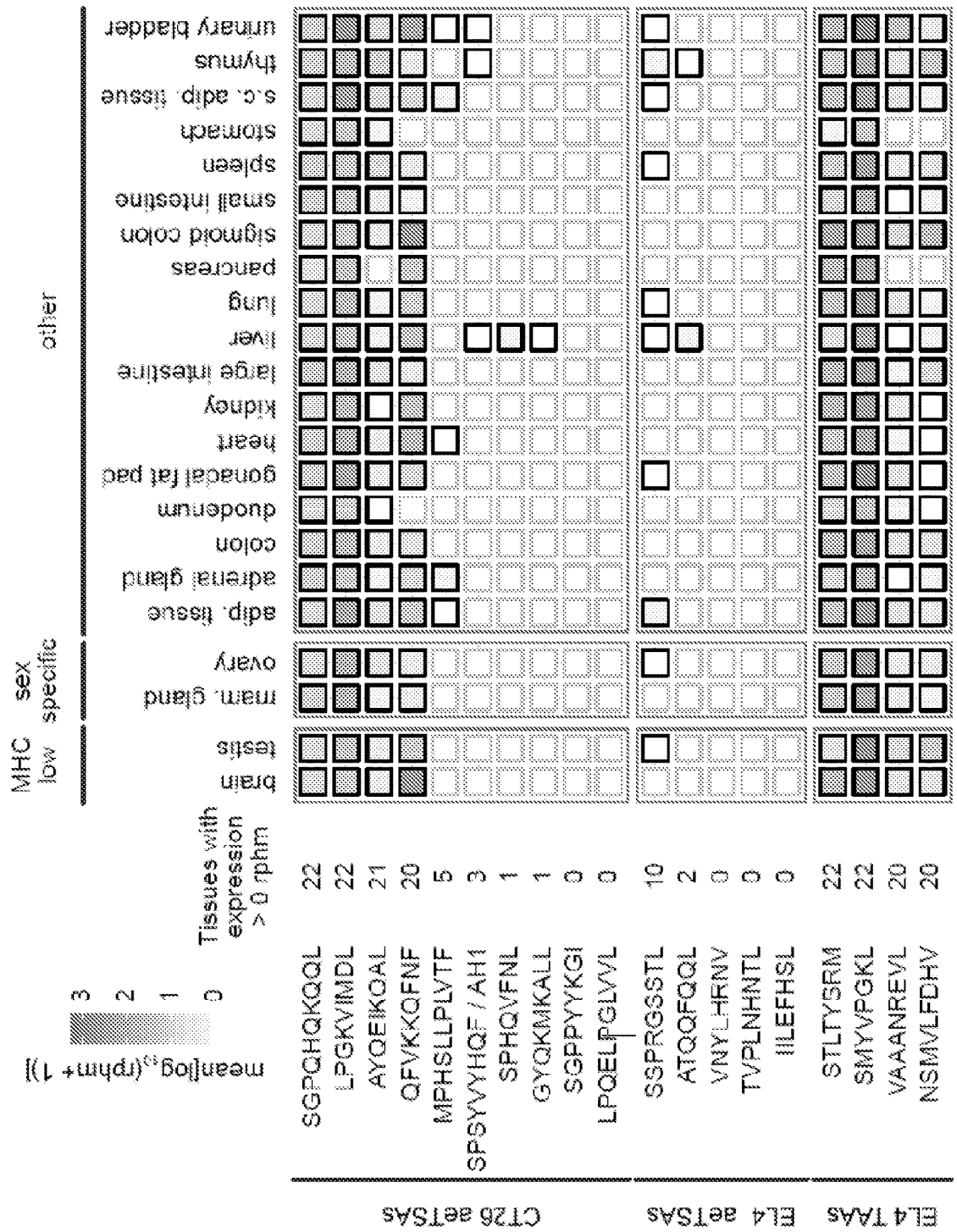
Figure 2D:
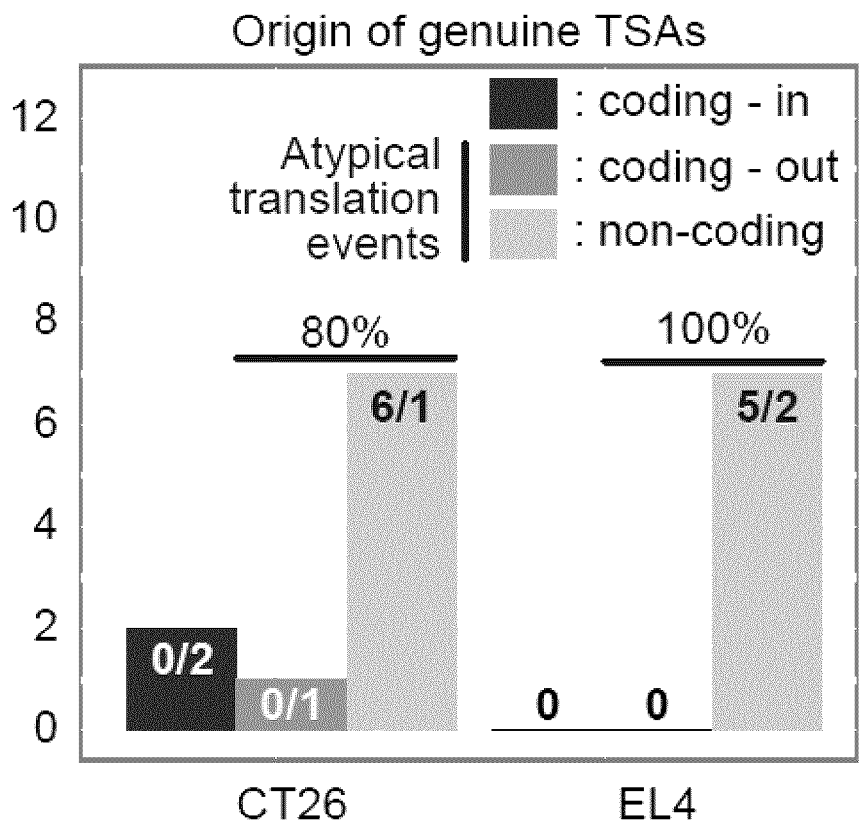

In order to assess the stringency of the database-building strategy based on the removal of mTEC$^{hi}$ k-mers from cancer k-mers, the peripheral expression of the MCS coding for aeTSAs across a panel of 22 tissues[38,39] was evaluated (Table 5). Four of the 15 aeTSA candidates had an expression profile similar to that of previously reported "overexpressed" tumor-associated antigens (TAAs)[40,41], as their MCS were expressed in most or all tissues (FIG. 2C). These four peptides were therefore excluded from the TSA list. In contrast, 11 MAPs were considered as genuine aeTSAs since their MCS were either totally absent or present at trace amounts in a few tissues (FIG. 2C). Indeed, detection of low transcript levels is insignificant since MAPs preferentially derive from highly abundant transcripts[42,43]. This concept is illustrated by the AH1 TSA which elicits strong antitumor responses devoid of adverse effects[9,37], despite the weak expression of its MCS in the liver, thymus and urinary bladder (FIG. 2C). These results demonstrate that subtracting mRNA sequences found in mTEC$^{hi}$ strongly enriches for cancer-restricted MCS. When the entire murine TSA dataset (6 mTSAs and 11 aeTSAs) is considered, the most salient finding is that most of them derive from atypical translation events: out-of-frame translation of coding exon or the translation of non-coding regions (FIG. 2D). Moreover, all but two of the TSAs identified would have been missed by classical exome-based approaches, as their source sequence is not annotated as protein-coding. Interestingly, it was also noticed that any type of non-coding region can generate TSAs (Table 1): intergenic and intronic sequences, non-coding exons, UTR/exon junctions, as well as ERE, which appear to be a particularly rich source of TSAs (8 aeTSAs and 1 mTSA). Finally, the approach described herein efficiently captured structural variants as an antigen, VTPVYQHL (SEQ ID NO:16), derived from a very large intergenic deletion (~7,500 bp) in EL4 cells (Table 1 b), was identified. Altogether, these observations confirm that non-coding regions are the main source of TSAs and that they have the potential to considerably expand the TSA landscape of tumors.

Figure 3A:
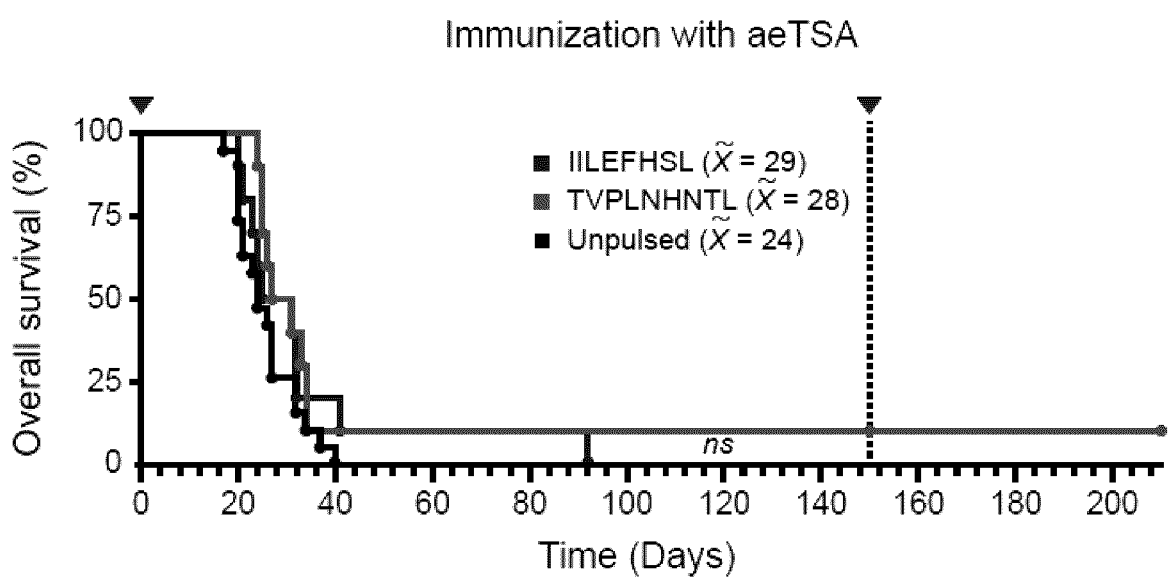
FIGS. 3A-C are graphs showing that immunization against individual TSAs confers different degrees of protection against EL4 cells. C57BL/6 female mice were immunized twice with DCs pulsed with individual TSAs as follows.
Figure 3B:
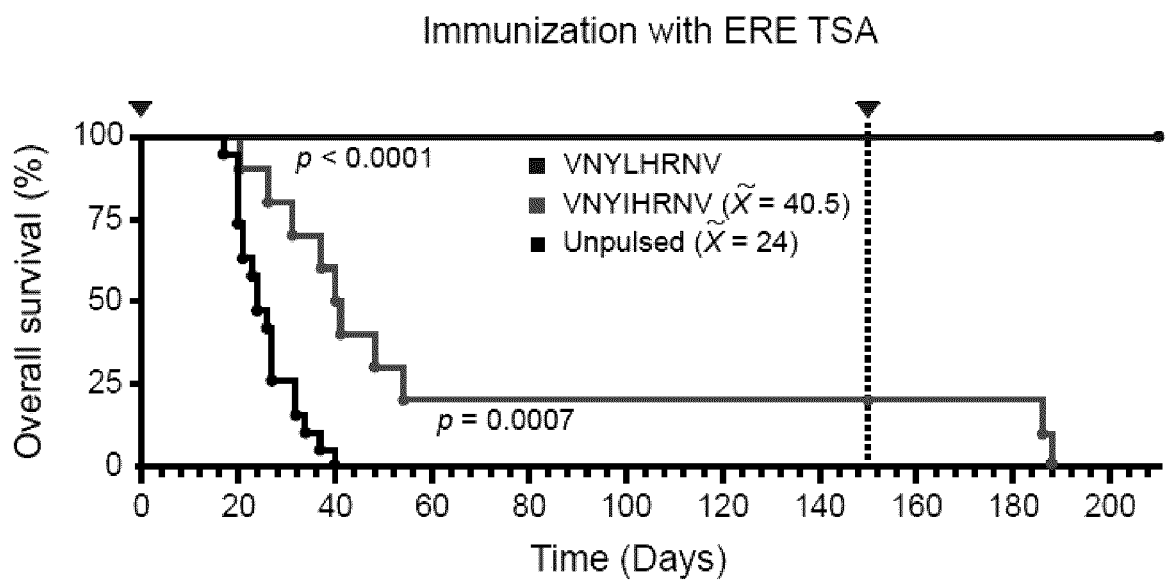
Figure 3C:
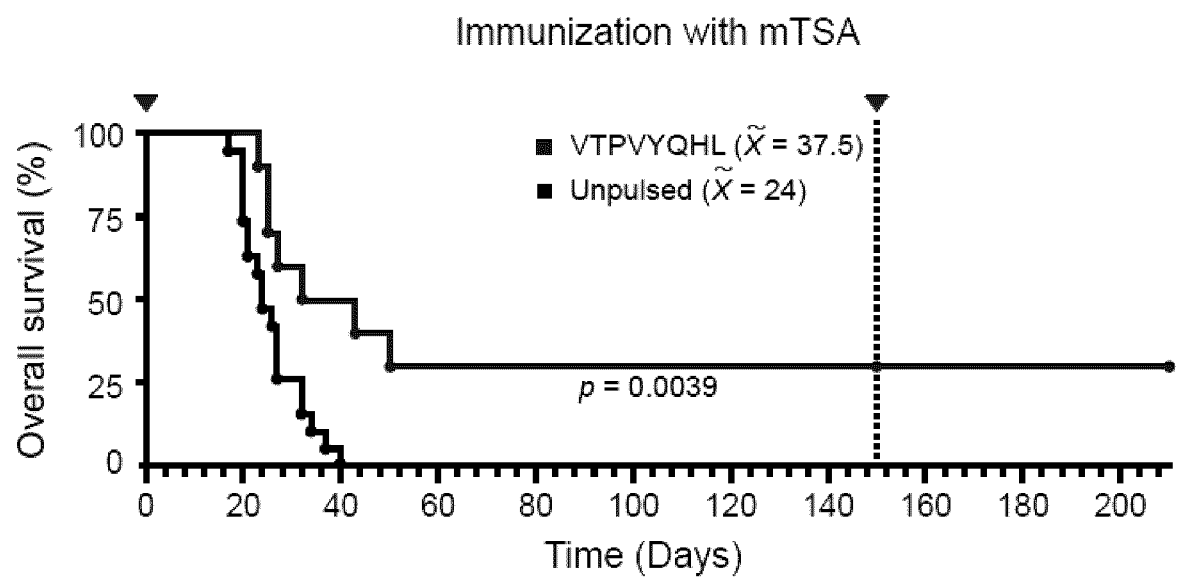

Further studies were performed on some of the TSAs that seemed most attractive, i.e., those presented by EL4 cells and whose MCS is not expressed by any normal tissue (FIG. 2C and Table 1b). To assess their immunogenicity, C57BL/6 mice were immunized twice with either unpulsed (control group) or TSA-pulsed DCs before being challenged with live EL4 cells. Priming against IILEFHSL (SEQ ID NO:12) or TVPLNHNTL (SEQ ID NO:14) prolonged survival for 10% of mice, with only TVPLNHNTL-immunized mouse surviving up day 150 (FIG. 3A). The other three TSAs showed day-150 survival rates of 20% (VNYIHRNV, SEQ ID NO:15), 30% (VTPVYQHL, SEQ ID NO:16) and 100% (VNYLHRNV, SEQ ID NO:15) (FIG. 3B,C). To evaluate long-term efficacy of TSA vaccination, surviving mice were rechallenged with live EL4 cells at day 150, signs of disease were monitored. The two VNYIHRNV-immunized survivors died of leukemia within 50 days, whereas all others (immunized against TVPLNHNTL (SEQ ID NO:14), VTPVYQHL (SEQ ID NO:16) or VNYLHRNV, SEQ ID NO:15) survived the rechallenge (FIG. 3). It may thus be concluded that immunization against individual TSAs confers different degrees of protection against EL4 cells, and that in most cases, this protection is long-lasting.

EXAMPLE 4: FREQUENCY OF TSA-SPECIFIC T CELLS IN NAIVE AND IMMUNIZED MICE

In various models, the strength of in vivo immune responses is regulated by the number of antigen-reactive T cells[44,45]. The frequency of TSA-specific T cells in naive and immunized mice was therefore assessed using a tetramer-based enrichment protocol[46,47], for which the gating strategy and one representative experiment can be found in FIGS. 9A-C. As positive controls, the highly abundant CD8 T cells specific for three viral epitopes (gp-33, M45 and B8R) was used, and it was confirmed that their frequency was within range of those observed in previous studies[45] (FIG. 4A). In naive mice, CD8 T cells specific for TVPLNHNTL (SEQ ID NO:14), VTPVYQHL (SEQ ID NO:16) and IILEFHSL (SEQ ID NO:12) were rare (less than one tetramer$^+$ cell per 10$^6$ CD8 T cells), while CD8 T cells specific for the ERE TSAs (VNYIHRNV and VNYLHRNV, SEQ ID NO:15) displayed frequencies similar to those of the viral controls (FIG. 4A and FIG. 10A). Accordingly, in mice immunized with TSA-pulsed DCs, it was found that the T cell frequencies against the two ERE TSAs, as assessed by tetramer staining or IFN-γ ELISpot assays (FIGS. 9C-D and 10A), were significantly higher than that of TVPLNHNTL (SEQ ID NO:14), VTPVYQHL (SEQ ID NO:16) and IILEFHSL (SEQ ID NO:12) (FIG. 4B-C). Moreover, in both naive and immunized mice, frequencies of antigen-specific T cells were found to be highly correlated (FIGS. 11A-C). Finally, it was estimated that the functional avidity of T cells specific for VNYIHRNV (SEQ ID NO:15) and VNYLHRNV (SEQ ID NO:15) was similar to that of T cells specific for two highly immunogenic non-self antigens: the minor histocompatibility antigens H7a and H13a (FIG. 4D). Hence, these TSAs, derived from allegedly non-coding regions, were recognized by highly abundant T cells with a high functional avidity. This is particularly noteworthy for the VNYIHRNV (SEQ ID NO:15) aeTSA since it has an unmutated germline sequence.

Taken together, these results show that the frequency of TSA-specific T cells is generally a significant parameter for TSA immunogenicity. However, VTPVYQHL (SEQ ID NO:16) afforded the second-to-best protection against EL4 challenge even though its cognate T cells were present at a very low frequency (FIGS. 3 and 4A-C). In order to better evaluate the importance of T-cell expansion in leukemia protection, the frequency of tetramer$^+$ CD8 T cells in long-term survivors following rechallenge with EL4 cells on day 150 was estimated (FIG. 3). These analyses were performed on day 210 or at the time of sacrifice (in the case of VNYIHRNV-primed mice). All long-term survivors, including VTPVYQHL-immunized mice, showed a conspicuous population of TSA-specific (tetramer$^+$) CD8 T cells (FIGS. 10B-C). Although VNYIHRNV (SEQ ID NO:15) was recognized by a large population of tetramer$^+$ cells, this was not sufficient to protect mice upon rechallenge in the experimental conditions used herein.

EXAMPLE 5: THE IMPORTANCE OF ANTIGEN EXPRESSION FOR PROTECTION AGAINST EL4 CELLS

Next, the impact of antigen expression on immunogenicity was evaluated by assessing the abundance of TSAs at the RNA level in the EL4 cell population that was injected on day 0 (FIG. 3). It was found that the sequence encoding the TSA conferring the best protection against EL4 cells (VNYLHRNV, SEQ ID NO:15) was expressed at much higher level than the other TSAs (FIG. 5A). This suggests that VNYLHRNV (SEQ ID NO:15) is likely "clonal" (expressed by all EL4 cells) and highly expressed whereas the other TSAs are sub-clonal and/or expressed at low levels. Next, using parallel reaction monitoring (PRM) MS, the TSA copy number per cell on the EL4 cell population used for rechallenge (day 150, FIG. 5B) was analyzed. There was no linear relationship between TSA abundance at the RNA and the peptide level[40] (FIG. 5A-B). Notably, the best TSA, VNYLHRNV (SEQ ID NO:15), was one of the two most abundant TSAs (>500 copies per cell), while VNYIHRNV (SEQ ID NO:15), which offered no significant protection upon rechallenge under the experimental conditions used herein (FIG. 3B), was no longer detected on EL4 cells. This observation suggests that VNYIHRNV (SEQ ID NO:15) was a sub-clonal TSA and that antigen-loss most likely explained the lack of significant protection upon rechallenge. Finally, it was noted that TSAs were immunogenic when presented by DCs but not when presented by EL4 cells: i) injection of live EL4 cells without prior immunization did not induce significant expansion of TSA-specific T cells, and ii) immunization with irradiated EL4 cells did not confer significant protection against live EL4 cells (FIGS. 5C-D and FIG. 10D). This suggests that, in the absence of immunization, highly immunogenic TSAs (such as VNYLHRNV, SEQ ID NO:15) were ignored because they were not efficiently cross-presented by DCs, highlighting the importance of efficient T-cell priming in cancer immunotherapy.

EXAMPLE 6: NON-CODING REGIONS EXPANDS THE TSA LANDSCAPE OF HUMAN PRIMARY TUMORS

Having established that non-coding regions are the main source of TSAs in two murine cell lines, the proteogenomic approach described herein was applied to seven human primary tumor samples: four B-lineage ALLs and three lung cancers. To do so, rather than using RNA-Seq data from murine syngeneic mTEC$^{hi}$, the transcriptome of total TECs (n=2) and purified mTECs (n=4) from six unrelated donors undergoing corrective cardiovascular surgery was sequenced. Notably, minimal inter-individual differences were found, and this cohort size was shown to be sufficient to cover almost the full breadth of the mTEC transcriptomic landscape (FIGS. 12A-B). Using these RNA-Seq data as the repertoire of normal k-mers for the workflow described in FIG. 1, 3 mTSAs and 27 aeTSA candidates were identified (FIG. 6A). Besides being extensively validated, it was also ensured that mTSAs did not intersect with known germline polymorphisms. In order to further validate the status of aeTSA candidates, the expression of aeTSA MCS in RNA-Seq data from 28 tissues (6-50 individuals per tissue, FIG. 6B and Table 6) was analyzed, similar to what was done for murine aeTSAs (FIG. 2C). Based on these data, six aeTSA candidates were excluded: i) three were widely expressed, alike most previously reported overexpressed TAAs[48], and ii) three were expressed at significant levels in a single organ, the liver (FIG. 6B). Thus, a total of three mTSAs and 20 non-redundant aeTSAs candidates were identified (FIG. 6C and Tables 2a-d and 3a-c). Of note, the SLTALVFHV aeTSA was shared by the two HLA-A*02:01-positive ALLs (Tables 2a and 2d). This aeTSA derives from the 3'UTR of TCL1A, a gene implicated in lymphoid malignancies. Altogether, the results show that the proteogenomic approach described herein can characterize the repertoire of mTSAs and aeTSAs on individual tumors in about two weeks.

TABLE 1a

CT26 TSAs

| TSA Sequence (SEQ ID NO) | Genomic Position | Ensembl Transcript id | TSA Origin | Frame | MHC I Molecule | Percentile Rank |
| --- | --- | --- | --- | --- | --- | --- |
| GYQKMKALL (SEQ ID NO: 1) | chr8:123429315-123429341 | | MuLV | | ERE | H-2-K$^d$ | 0.06 |
| KPL<u>K</u>/EAPLDL (SEQ ID NO: 2) | chr1:173783238-173783264 | ENSMUST00000155076 | Intron | | H-2-L$^d$ | 0.01 |
| KYLSVQ<u>S</u>/GQL (SEQ ID NO:3) | chr17:29332770-29332778\|<br><br>chr17:29333514-29333531 | ENSMUST00000095427 | Coding exon | In-frame | H-2-K$^d$ | 0.01 |
| KYLSVQ<u>S</u>/GQLF (SEQ ID NO: 4) | chr17:29332767-29332778\|<br><br>chr17:29333514-29333531 | ENSMUST00000095427 | Coding exon | In-frame | H-2-K$^d$ | 0.25 |
| LPQELPGLVVL (SEQ ID NO: 5) | chr8:123427101-123427133 | | MuLV | | ERE | H-2-L$^d$ | 0.5 |
| MPHSLLPLVTF (SEQ ID NO: 6) | chr7:89664573-89664605 | ENSMUST00000159167 | Intron | | H-2-L$^d$ | 0.2 |
| QGPMALR<u>I</u>/LF (SEQ ID NO: 7) | chr9:66126885-66126911 | ENSMUST00000034945 | Coding exon | Out-of-frame | H-2-D$^d$ | 0.05 |
| SGPPYYKGI (SEQ ID NO: 8) | chr8:121839803-121839829 | MMERGLN_I or ENSMUST00000127664 | ERE or Intron | | H-2-D$^d$ | 0.25 |
| SPHQVFNL (SEQ ID NO: 9) | chr8:123428239-123428262 | | MuLV | | ERE | H-2-L$^d$ | 0.01 |
| SPSYVYHQF (SEQ ID NO: 10) | chr8:123426985-123427011 | | MuLV | | ERE | H-2-L$^d$ | 0.5 |

TABLE 1b

EL4 TSAs

| TSA Sequence (SEQ ID NO) | Genomic Position | Ensembl Transcript id | TSA Origin Frame | MHC I Molecule | Percentile Rank |
|---|---|---|---|---|---|
| ATQQFQQL (SEQ ID NO: 11) | chr8:123426867-123426844 | MuLV | ERE | H-2-K$^b$ | 0.2 |
| IILEFHSL (SEQ ID NO: 12) | chr10:116678525-116678548 | ENSMUST00000181656 | Non-coding exon | H-2-K$^b$ | 0.02 |
| SSPRGSSTL (SEQ ID NO: 13) | chr6:114732754-114732780 | B3A or ENSMUST00000032457 | ERE or Intron | H-2-D$^b$ | 0.3 |
| TVPLNHNTL (SEQ ID NO: 14) | chr4:83615597-83615624 | ENSMUST00000053414 | Novel antisense | H-2-D$^b$ | 0.12 |
| VNY<u>I</u>/LHRNV (SEQ ID NO: 15) | chr4:46583174-46583197 | MMTV | ERE | H-2-K$^b$ | 0.01 |
| VNYI/<u>L</u>HRNV (SEQ ID NO: 15) | chr4:46583174-46583197 | MMTV | ERE | H-2-K$^b$ | 0.01 |
| VTPVYQ\|HL (SEQ ID NO: 16) | chr2:75078751-75078756\| chr2:75086270-75086287 | N/A | Intergenic | H-2-K$^b$ | 0.01 |

TABLE 2a

Features of human TSAs detected B-ALL specimens – 07H103 TSAs

| TSA Sequence (SEQ ID NO) | Genomic Position | Ensembl Transcript id | TSA Origin Frame | MHC I Molecule | Percentile Rank |
|---|---|---|---|---|---|
| KILILLQSL (SEQ ID NO: 17) | chr5:132450600-132450626 | L1ME3G or ENST00000407797 | ERE or Intron | A*02:01 | 1.8 |
| KISLYLPAL (SEQ ID NO: 18) | chr8:144861684-144861710 | LTR46-int | ERE | A*02:01 | 0.5 |
| SLTALVFHV (SEQ ID NO: 19) | chr14:95710533-95710559 | ENST00000554012 | 3'UTR | A*02:01 | 0.06 |

TABLE 2b

Features of human TSAs detected B-ALL specimens – 10H080 TSAs

| TSA Sequence (SEQ ID NO) | Genomic Position | Ensembl Transcript id | TSA Origin Frame | MHC I Molecule | Percentile Rank |
|---|---|---|---|---|---|
| HETLRLLL (SEQ ID NO: 20) | chr6:106197722-106197745 | ENST00000369076 | Intron | B*40:01 | 1.2 |
| RIFGFRLWK (SEQ ID NO: 21) | chr1:80641339-80641365 | ENST00000418041 | Intron | A*11:01 | 0.01 |
| TSFAETWMK (SEQ ID NO: 22) | chr7:43947484-43947510 | L1PA6 or ENST00000427076 | Intron or ERE | A*11:01 | 0.01 |
| TSIPKPNLK (SEQ ID NO: 23) | chr2:237428272-237428298 | N/A | Intergenic | A*11:01 | 0.15 |

TABLE 2c

Features of human TSAs
detected B-ALL specimens - 10H118 TSAs

| TSA Sequence (SEQ ID NO) | Genomic Position | Ensembl Transcript id | TSA Origin Frame | MHC I Molecule | Percentile Rank |
|---|---|---|---|---|---|
| LPFEQKSL (SEQ ID NO: 24) | chr2:47522843-47522866 | ENST00000327876 | Intron | B*08:01 | 0.7 |
| SLREKGFSI (SEQ ID NO: 25) | chr1:175955400-175955426 | ENST00000367667 | Intron | B*08:01 | 0.09 |
| VPAALRSL (SEQ ID NO: 26) | chr7:106886341-106886364 | ENST00000359195 | Intron | B*07:02 | 0.3 |

TABLE 2d

Features of human TSAs
detected B-ALL specimens - 12H018 TSAs

| TSA Sequence (SEQ ID NO) | Genomic Position | Ensembl Transcript id | TSA Origin Frame | MHC I Molecule | Percentile Rank |
|---|---|---|---|---|---|
| LLAATILLSV (SEQ ID NO: 27) | chr2:174631426-174631455 | ENST00000392547 | Intron | A*02:01 | 0.2 |
| SLFVA/VSLSL (SEQ ID NO: 28) | chr6:106971679-106971705 | ENST00000606017 | Coding exon In-frame | A*02:01 | 0.6 |
| SLTALVFHV (SEQ ID NO: 19) | chr14:95710533-95710559 | ENST00000402399 | 3'UTR | A*02:01 | 0.06 |

TABLE 3a

Features of human TSAs detected in lung tumor biopsies - Ic2 TSAs

| TSA Sequence (SEQ ID NO) | Genomic Position | Ensembl Transcript id | TSA Origin Frame | MHC I Molecule | Percentile Rank |
|---|---|---|---|---|---|
| IIAPPPPPK (SEQ ID NO: 29) | chr14:21098919-21098945 | ENST00000421093 | 5'UTR | A*11:01 | 0.15 |
| LVFNIILHR (SEQ ID NO: 30) | chr6:6800963-6800989 | N/A | Intergenic | A*11:01 | 0.25 |
| MISPVLALK (SEQ ID NO: 31) | chr19:41751004-41751030 | ENST00000595740 | 5'UTR | A*11:01 | 0.03 |
| SLSYLILKK (SEQ ID NO: 32) | chrX:107212979-107213005 | ENST00000372453 | Coding exon Out-of-frame | A*11:01 | 0.05 |
| SSASQLPSK (SEQ ID NO: 33) | chr16:19430493-19430519 | L4_B_Mam or ENST00000542583 | ERE or 5'UTR | A*11:01 | 0.07 |
| SVIQTGHLAK (SEQ ID NO: 34) | chr3:169840282-169840311 | ENST00000316428 | Coding exon In-frame | A*11:01 | 0.1 |
| TTLKYLWKK (SEQ ID NO: 35) | chr3:169381477-169381503 | ENST00000485957 | 5'UTR | A*11:01 | 0.03 |

TABLE 3b

Features of human TSAs detected in lung tumor biopsies - Ic4 TSAs

| TSA Sequence (SEQ ID NO) | Genomic Position | Ensembl Transcript id | TSA Origin Frame | MHC I Molecule | Percentile Rank |
|---|---|---|---|---|---|
| KPSVFPLSL (SEQ ID NO: 36) | chr14:37589683-37589708 | N/A | Intergenic | B*07:02 | 0.15 |

TABLE 3c

Features of human TSAs detected in lung tumor biopsies - Ic6 TSAs

| TSA Sequence (SEQ ID NO) | Genomic Position | Ensembl Transcript id | TSA Origin Frame | MHC I Molecule | Percentile Rank |
|---|---|---|---|---|---|
| QR/KF/LQGRVTM (SEQ ID NO: 37) | chr15:19972868-19972894 | N/A | Intergenic | C*07:01 | 0.02 |
| SRFSGVPDRF (SEQ ID NO: 38) | chr2:89234284-89234313 | N/A | Intergenic | A*24:02 | 0.9 |
| TYTQN/DFNKF (SEQ ID NO: 39) | chr11:14968916-14968942 | ENST00000331587 | Coding exon In-frame | A*24:02 | 0.03 |

TABLE 4a

Statistics related to the generation of the global cancer databases-murine samples

| | | | EL4 | mTEChi_C57BL/6 | CT26 | mTEChi_Balb/c |
|---|---|---|---|---|---|---|
| Canonical proteomes | transcripts | Expressed (tpm > 0) | 64318 | 86947 | 65242 | 82420 |
| | | Protein-coding | 34171 | 47086 | 35104 | 44943 |
| | proteins | Distinct | 35280 | 50304 | 37810 | 54456 |
| Cancer-specific proteomes | reads | Total | 240372644 | 456991966 | 247522370 | 455625158 |
| | k-mers (k = 33 nts) | Total | 14862978110 | 28980506746 | 15026027458 | 21482018335 |
| | | Distinct | 429163639 | 1084732266 | 507092097 | 1115569754 |
| | | Count ≥ 4 | 116852296 | | 104699335 | |
| | | Cancer-specific | 19091379 | | 22892864 | |
| | contigs | Distinct ≥ 34 nts | 895313 | | 1845144 | |
| | | | 715161 | | 1377631 | |
| | proteins | Distinct, ≥ 8 aa | 2153996 | | 3701717 | |

TABLE 4b

Statistics related to the generation of the global cancer databases-human samples

| | | | 07H103 | 10H080 | 10H118 |
|---|---|---|---|---|---|
| Canonical proteomes | transcripts | Expressed (tpm >0) | 107590 | 115494 | 116981 |
| | | Protein-coding | 57931 | 62280 | 63133 |
| | proteins | Distinct | 59082 | 64150 | 63921 |
| Cancer-specific proteomes | reads | Total | 105 863 640 | 129 444 492 | 226 508 070 |
| | k-mers (k = 33 nts) | Total | 6 739 820 561 | 8 297 285 105 | 13 804 699 469 |
| | | Distinct | 633 011 468 | 761 444 095 | 1 119 514 550 |
| | | Count ≥7 or 10 | 77 745 744 | 98 652 247 | 135 682 880 |
| | | Cancer-specific | 11 694 475 | 20 210 820 | 32 070 840 |
| | contigs | Distinct | 492 273 | 778 594 | 1 412 680 |
| | | ≥34 nts | 440 367 | 697 184 | 1 246 048 |
| | proteins | Distinct, ≥8 aa | 1 326 854 | 2 156 187 | 3 708 759 |

TABLE 4b-continued

Statistics related to the generation of the global cancer databases-human samples

|  |  |  | 12H018 | Ic2 | Ic4 |
|---|---|---|---|---|---|
| Canonical proteomes | transcripts | Expressed (tpm >0) | 113438 | 116600 | 117476 |
|  |  | Protein-coding | 61481 | 66874 | 67549 |
|  | proteins | Distinct | 63767 | 70493 | 71734 |
| Cancer-specific proteomes | reads | Total | 161 724 658 | 268 396 930 | 262 531 548 |
|  | k-mers (k = 33 nts) | Total | 9 981 973 250 | 17 197 030 205 | 17 341 587 177 |
|  |  | Distinct | 868 719 740 | 669 751 679 | 727 571 721 |
|  |  | Count ≥7 or 10 | 96 193 003 | 78 611 668 | 81 410 185 |
|  |  | Cancer-specific | 17 879 385 | 9 003 814 | 9 918 787 |
|  | contigs | Distinct | 758 491 | 669 145 | 749 712 |
|  |  | ≥34 nts | 666 164 | 513 928 | 581 510 |
|  | proteins | Distinct, ≥8 aa | 2 014 334 | 1 401 735 | 1 554 082 |
|  |  |  | Ic6 | 102015 | 062015 |
| Canonical proteomes | transcripts | Expressed (tpm >0) | 119870 | 62976 | 85686 |
|  |  | Protein-coding | 67135 | 37073 | 49155 |
|  | proteins | Distinct | 71526 | 46181 | 67497 |
| Cancer-specific proteomes | reads | Total | 246 868 078 | 134 624 214 | 136 558 238 |
|  | k-mers (k = 33 nts) | Total | 16 284 413 566 | a | a |
|  |  | Distinct | 864 050 270 |  |  |
|  |  | Count ≥7 or 10 | 97 121 823 |  |  |
|  |  | Cancer-specific | 17 663 050 |  |  |
|  | contigs | Distinct | 1 113 278 |  |  |
|  |  | ≥34 nts | 886 470 |  |  |
|  | proteins | Distinct, ≥8 aa | 2 431 066 |  |  |
|  |  |  | S5 | S9 | S10 | S11 |
| Canonical proteomes | transcripts | Expressed (tpm >0) | 95090 | 118246 | 112739 | 119225 |
|  |  | Protein-coding | 55103 | 66223 | 63113 | 66695 |
|  | proteins | Distinct | 70276 | 79469 | 75384 | 80996 |
| Cancer-specific proteomes | reads | Total | 200363532 | 229281098 | 231185678 | 251770122 |
|  |  | Total | a | a | a | a |
|  | k-mers (k = 33 nts) | Distinct | b | b | b | b |
|  |  | Count ≥7 or 10 |  |  |  |  |
|  |  | Cancer-specific |  |  |  |  |
|  | contigs | Distinct |  |  |  |  |
|  |  | ≥34 nts |  |  |  |  |
|  | proteins | Distinct, ≥8 aa |  |  |  |  |

TABLE 5

Accession numbers of the ENCODE datasets used in this study

| Tissue | Accession numbers (SRA) |
|---|---|
| Adipose tissue | SRR5171088, SRR5171089 |
| Adrenal gland | SRR5171111, SRR5171112, SRR5047957, SRR5047958, SRR5047959, SRR5047960, SRR5047961, SRR5047962 |
| Brain | SRR5171101, SRR5171102 |
| Colon | SRR5047913, SRR5047914, SRR5047915, SRR5047916, SRR5047917, SRR5047918 |
| Duodenum | SRR5047963, SRR5047964, SRR5047965, SRR5047966, SRR5047967, SRR5047968, SRR5047969 |
| Gonadal fat pad | SRR5047970, SRR5047971, SRR5047972, SRR5047973 |
| Heart | SRR5171076, SRR5171077, SRR5047921, SRR5047922, SRR5047923, SRR5047924 |
| Kidney | SRR5047925, SRR5047926, SRR5047927, SRR5047928, SRR5047929, SRR5047930, SRR5171094, SRR5171095 |
| Large Intestine | SRR5047975, SRR5047976, SRR5047977, SRR5047978 |
| Liver | SRR3192469, SRR3192470, SRR5171078, SRR5171079, SRR5047931, SRR5047932, SRR5047933, SRR5047934, SRR5047935, SRR5047936 |
| Lung | SRR5171113, SRR5171114, SRR5047937, SRR5047938, SRR5047939, SRR5047940 |
| Mammary gland | SRR5047979, SRR5047980, SRR5047981, SRR5047982, SRR5047983, SRR5047984 |
| Ovary | SRR5047985, SRR5047986, SRR5047987, SRR5047988, SRR5047989, SRR5047990, SRR5047991, SRR5047992, SRR5047993, SRR5047994, SRR5171100 |
| Pancreas | SRR5171086, SRR5171087 |
| Sigmoid colon | SRR5171098, SRR5171099 |

TABLE 5-continued

Accession numbers of the ENCODE datasets used in this study

| Tissue | Accession numbers (SRA) |
| --- | --- |
| Small Intestine | SRR5048001, SRR5048002, SRR5048003, SRR5048004, SRR5048005, SRR5048006, SRR5048007, SRR5048008, SRR5048009, SRR5048010, SRR171080, SRR5171081 |
| Spleen | SRR5047941, SRR5047942, SRR5047943, SRR5047944, SRR5047945, SRR5047946, SRR5171241, SRR5171242 |
| Stomach | SRR5047997, SRR5047996, SRR5047995, SRR5047998, SRR5048000, SRR5047999 |
| Subcutaneous adipose tissue | SRR5048011, SRR5048012, SRR5048013, SRR5048014 |
| Testis | SRR5047953, SRR5047954, SRR5047955, SRR5047956, SRR5171085, SRR5171084 |
| Thymus | SRR5047947, SRR5047948, SRR5047949, SRR5047950, SRR5047951, SRR5047952 |
| Urinary bladder | SRR5048035, SRR5048036 |

TABLE 6

Accession numbers of the GTEx datasets used in this study

| Tissue | Accession numbers (SRA) of randomly selected donors |
| --- | --- |
| Adipose-Subcutaneous | SRR599313 SRR608150 SRR608198 SRR612263 SRR612707 SRR612815 SRR612863 SRR612935 SRR613150 SRR613234 SRR613342 SRR613390 SRR613533 SRR613550 SRR613639 SRR613675 SRR613855 SRR613896 SRR613915 SRR613927 SRR614119 SRR614191 SRR614395 SRR614419 SRR614864 SRR615069 SRR615237 SRR615431 SRR615659 SRR615778 SRR615874 SRR615946 SRR617841 SRR654730 SRR654862 SRR654898 SRR655182 SRR655531 SRR655637 SRR655768 SRR655816 SRR656059 SRR656946 SRR657599 SRR657949 SRR658081 SRR658754 SRR658941 SRR658953 SRR659109 |
| Adrenal Gland | SRR1069421 SRR1070913 SRR1072626 SRR1073365 SRR1073775 SRR1074474 SRR1075314 SRR1076632 SRR1076823 SRR1082035 SRR1082616 SRR1082733 SRR1083824 SRR1083892 SRR1085590 SRR1085951 SRR1086046 SRR1087297 SRR1087511 SRR1087606 SRR1088365 SRR1088461 SRR1089479 SRR1089950 SRR1091476 SRR1092160 SRR1092329 SRR1092686 SRR1093625 SRR1093721 SRR1093954 SRR1094144 SRR1099378 SRR1099427 SRR1099598 SRR1099694 SRR1100496 SRR1100728 SRR808862 SRR809873 SRR810129 SRR810713 SRR811237 SRR811631 SRR812246 SRR814407 SRR816495 SRR816865 SRR817649 SRR818694 |
| Artery-Aorta | SRR1069376 SRR1070111 SRR1070641 SRR1071644 SRR1072078 SRR1072749 SRR1073705 SRR1074478 SRR1074622 SRR1075028 SRR1075579 SRR1076343 SRR1077090 SRR1078586 SRR1079023 SRR1079998 SRR1080148 SRR1081137 SRR1081519 SRR1081910 SRR1082283 SRR1083076 SRR1083286 SRR1083604 SRR1084276 SRR1084460 SRR1085159 SRR654850 SRR808044 SRR808152 SRR808351 SRR808836 SRR808914 SRR809320 SRR809470 SRR809785 SRR809831 SRR810201 SRR810367 SRR811333 SRR811471 SRR811819 SRR812673 SRR813632 SRR815092 SRR816565 SRR817744 SRR818232 SRR818999 SRR819293 |
| Bladder | SRR1071717 SRR1079830 SRR1081765 SRR1085402 SRR1086236 SRR1092208 SRR1093930 SRR1097296 SRR1099957 SRR1120296 SRR2135324 SRR2135407 |
| Brain-Cortex | SRR1081741 SRR1082262 SRR1083632 SRR1085975 SRR1310008 SRR1310136 SRR1311400 SRR1311575 SRR1311794 SRR1312428 SRR1314958 SRR1315269 SRR1315866 SRR1316815 SRR1320280 SRR1323043 SRR1323746 SRR1324371 SRR1327593 SRR1328487 SRR598332 SRR601006 SRR601669 SRR602927 SRR603333 SRR604026 SRR608662 SRR612575 SRR614310 SRR615213 SRR615838 SRR627421 SRR627425 SRR627449 SRR627455 SRR654874 SRR656745 SRR659555 SRR660626 SRR660933 SRR663320 SRR663753 SRR664854 SRR808614 SRR810319 SRR810877 SRR812012 SRR812436 SRR816770 SRR820078 |
| Breast-Mammary Tissue | SRR1068977 SRR1068999 SRR1070208 SRR1070260 SRR1070738 SRR1071084 SRR1071905 SRR1074860 SRR1075484 SRR1076219 SRR1076441 SRR1077139 SRR1077920 SRR1078258 SRR1079948 SRR1081023 SRR1082859 SRR1083052 SRR1083959 SRR1084079 SRR1084674 SRR1086538 SRR1086772 SRR615910 SRR655447 SRR655852 SRR656911 SRR656970 SRR657018 SRR657528 SRR658105 SRR658319 SRR658409 SRR659223 SRR660248 SRR660283 SRR662306 SRR662378 SRR662811 SRR808428 SRR808942 SRR811073 SRR811285 SRR812198 SRR813868 SRR815208 SRR816336 SRR818873 SRR820571 SRR821498 |
| Cervix-Ectocervix | SRR1075223 SRR1088832 SRR1089562 SRR1096876 SRR1097035 SRR1097574 |

TABLE 6-continued

Accession numbers of the GTEx datasets used in this study

| Tissue | Accession numbers (SRA) of randomly selected donors |
|---|---|
| Colon-Sigmoid | SRR1069943 SRR1074337 SRR1077380 SRR1081068 SRR1083504 SRR1083678 SRR1084505 SRR1086020 SRR1087271 SRR1090431 SRR1091524 SRR1092493 SRR1093366 SRR1102198 SRR1102224 SRR1102998 SRR1308269 SRR1312577 SRR1312666 SRR1312784 SRR1317110 SRR1317653 SRR1318624 SRR1319038 SRR1320445 SRR1320490 SRR1321377 SRR1322070 SRR1323002 SRR1323215 SRR1324473 SRR1327454 SRR1327505 SRR1327527 SRR1327570 SRR1328528 SRR1328980 SRR1329642 SRR1329663 SRR1330176 SRR1330770 SRR1330831 SRR1332467 SRR1333167 SRR1333287 SRR1334011 SRR1334055 SRR1334181 SRR1336617 SRR1336863 |
| Esophagus-Mucosa | SRR1069231 SRR1069255 SRR1069328 SRR1069666 SRR1069871 SRR1070036 SRR1070060 SRR1070620 SRR1070665 SRR1071207 SRR1071499 SRR1072055 SRR1072297 SRR1072388 SRR1072480 SRR1073631 SRR1074450 SRR1074502 SRR1074578 SRR1075458 SRR1075603 SRR1076195 SRR1076705 SRR1076801 SRR1077310 SRR1077356 SRR1077619 SRR1077850 SRR1078140 SRR1078538 SRR807679 SRR807703 SRR809406 SRR809919 SRR812294 SRR812318 SRR813283 SRR813505 SRR813536 SRR814467 SRR815116 SRR815568 SRR816403 SRR817306 SRR819124 SRR819559 SRR819637 SRR820280 SRR820689 SRR821282 |
| Fallopian Tube | SRR1071359 SRR1074140 SRR1076584 SRR1082520 SRR1083776 SRR1101693 SRR811938 |
| Heart-Left Ventricle | SRR598148 SRR598509 SRR598589 SRR599025 SRR599086 SRR599249 SRR599380 SRR600474 SRR600829 SRR600852 SRR600924 SRR601239 SRR601613 SRR601645 SRR601868 SRR601986 SRR602106 SRR602437 SRR602461 SRR603449 SRR603918 SRR603968 SRR604122 SRR604174 SRR604206 SRR604230 SRR606939 SRR607252 SRR607313 SRR607970 SRR608096 SRR608480 SRR612335 SRR612719 SRR612875 SRR613186 SRR613462 SRR613510 SRR613759 SRR614215 SRR614683 SRR614996 SRR615335 SRR615359 SRR615898 SRR615970 SRR655792 SRR657903 SRR658283 SRR658331 |
| Kidney-Cortex | SRR1071807 SRR1080366 SRR1085759 SRR1089504 SRR1105272 SRR1314940 SRR1317086 SRR1325483 SRR1328447 SRR1329154 SRR1340662 SRR1362263 SRR1377578 SRR1380931 SRR1396700 SRR1416516 SRR1420649 SRR1432650 SRR1433066 SRR1435730 SRR1437274 SRR1442708 SRR1443092 SRR1445835 SRR1447631 SRR1452888 SRR1456711 SRR1465871 SRR1468426 SRR1469746 SRR1486080 SRR1490658 SRR1500261 SRR2135353 SRR2135396 SRR809943 SRR810007 SRR821356 |
| Liver | SRR1069141 SRR1070689 SRR1071668 SRR1073435 SRR1075102 SRR1075804 SRR1076022 SRR1080117 SRR1080294 SRR1081184 SRR1082151 SRR1083983 SRR1086256 SRR1087007 SRR1087321 SRR1089446 SRR1090095 SRR1090556 SRR1091865 SRR1093861 SRR1095383 SRR1095913 SRR1098737 SRR1100991 SRR1101883 SRR1102152 SRR1102899 SRR1105248 SRR1120939 SRR1310433 SRR1312266 SRR1313807 SRR1316096 SRR1317532 SRR1317554 SRR1321877 SRR1322312 SRR1322477 SRR1323491 SRR1324295 SRR1324412 SRR1325290 SRR1328760 SRR1331488 SRR1334866 SRR1335236 SRR1336314 SRR815140 SRR815711 SRR821043 |
| Lung | SRR1070015 SRR1070358 SRR1071568 SRR1072150 SRR1073119 SRR1074769 SRR1081283 SRR1084602 SRR1084766 SRR1086728 SRR1087559 SRR1091670 SRR1095695 SRR1098074 SRR1098785 SRR1098998 SRR1099286 SRR1099546 SRR1102079 SRR1102804 SRR1307123 SRR1307615 SRR1308239 SRR1308504 SRR1308939 SRR1309452 SRR1309468 SRR1309490 SRR1310313 SRR1310520 SRR1310797 SRR1310959 SRR1310975 SRR1312209 SRR1312522 SRR1312558 SRR813043 SRR814244 SRR814703 SRR817004 SRR817070 SRR817166 SRR817488 SRR818499 SRR819186 SRR819318 SRR819658 SRR820596 SRR821302 SRR821525 |
| Minor Salivary Gland | SRR1071105 SRR1078392 SRR1080790 SRR1081589 SRR1097245 SRR1100608 SRR1315412 SRR1318089 SRR1321897 SRR1325201 SRR1328715 SRR1330723 SRR1331771 SRR1338384 SRR1339987 SRR1340260 SRR1348929 SRR1353600 SRR1356057 SRR1358391 SRR1376380 SRR1376450 SRR1376741 SRR1381185 SRR1382978 SRR1385690 SRR1386927 SRR1388459 SRR1389955 SRR1397720 SRR1400931 SRR1404339 SRR1405147 SRR1406135 SRR1406348 SRR1407044 SRR1413307 SRR1416141 SRR1416188 SRR1416841 SRR1418225 SRR1418473 SRR1418747 SRR1419561 SRR1429429 SRR1429540 SRR1431823 SRR1432868 SRR1432958 SRR1433493 |
| Muscle-Skeletal | SRR1068855 SRR1071231 SRR1071594 SRR1071955 SRR1074359 SRR1074670 SRR1074719 SRR1077288 SRR1077805 SRR1080766 SRR1084369 SRR1084417 SRR1085519 SRR1087245 SRR1087825 SRR1088581 SRR1089424 SRR1089901 SRR1090265 SRR1092349 SRR1092985 SRR1094051 SRR1095720 SRR1096174 SRR1096662 SRR1098474 SRR1098879 SRR1100588 SRR1102830 SRR1105057 SRR812773 SRR813656 SRR813802 SRR813983 SRR815020 SRR815044 SRR815470 SRR815783 SRR815825 SRR816015 SRR816226 SRR816382 SRR817282 SRR817421 SRR818600 SRR818773 SRR818901 SRR819054 SRR819261 SRR820907 |
| Nerve-Tibial | SRR1070086 SRR1070159 SRR1070597 SRR1072724 SRR1073553 SRR1074550 SRR1075384 SRR1075825 SRR1076559 SRR1079636 SRR1079850 SRR1080093 SRR1082059 SRR1082809 SRR1086417 SRR1087079 SRR1088706 SRR1090070 SRR1091184 SRR1092062 SRR1095334 SRR1096007 SRR1096222 SRR1096478 |

TABLE 6-continued

Accession numbers of the GTEx datasets used in this study

| Tissue | Accession numbers (SRA) of randomly selected donors |
|---|---|
| | SRR1096500 SRR1096806 SRR1097055 SRR1098385 SRR1310455 SRR1310645 SRR1311131 SRR1311308 SRR1312370 SRR1312464 SRR813704 SRR814052 SRR814996 SRR815422 SRR815685 SRR817026 SRR817397 SRR817539 SRR817609 SRR818939 SRR818961 SRR820350 SRR820402 SRR821096 SRR821124 SRR821255 |
| Ovary | SRR1071475 SRR1073389 SRR1073878 SRR1075360 SRR1078042 SRR1078636 SRR1078735 SRR1081987 SRR1082352 SRR1082471 SRR1085565 SRR1085736 SRR1086212 SRR1086656 SRR1088856 SRR1089134 SRR1090698 SRR1090928 SRR1091164 SRR1092038 SRR1093601 SRR1093747 SRR1096458 SRR1097124 SRR1097148 SRR1098807 SRR1099310 SRR1099669 SRR1101453 SRR1101859 SRR1102005 SRR1102780 SRR1120276 SRR1312446 SRR1315495 SRR1316513 SRR1319793 SRR1336244 SRR1339699 SRR1340598 SRR1341583 SRR1342849 SRR1347518 SRR1350891 SRR1351641 SRR1353537 SRR814293 SRR814892 SRR816629 SRR821072 |
| Pancreas | SRR1069352 SRR1070403 SRR1070764 SRR1071519 SRR1072007 SRR1072104 SRR1072972 SRR1073021 SRR1073167 SRR1073991 SRR1074090 SRR1074385 SRR1075174 SRR1075336 SRR1076244 SRR1076868 SRR1078066 SRR1079754 SRR1080624 SRR1082080 SRR1082544 SRR1084128 SRR1084323 SRR1085187 SRR1085310 SRR1086070 SRR1087728 SRR1088291 SRR1088413 SRR1088537 SRR1089537 SRR1089688 SRR1091032 SRR1091144 SRR1092937 SRR1093340 SRR1093434 SRR1093577 SRR1095407 SRR1095479 SRR1095651 SRR1097777 SRR1097883 SRR812745 SRR813208 SRR816541 SRR819771 SRR821050 SRR821231 SRR821666 |
| Pituitary | SRR1076393 SRR1077455 SRR1077708 SRR1077968 SRR1082664 SRR1082685 SRR1089785 SRR1096101 SRR1096339 SRR1101612 SRR1309119 SRR1309638 SRR1310817 SRR1311599 SRR1311709 SRR1311958 SRR1317963 SRR1318026 SRR1319946 SRR1321650 SRR1323977 SRR1324141 SRR1324184 SRR1325161 SRR1325944 SRR1326408 SRR1326797 SRR1328143 SRR1331962 SRR1332024 SRR1332904 SRR1336029 SRR1336529 SRR1337321 SRR1339007 SRR1340241 SRR1343012 SRR1343221 SRR1343720 SRR1343778 SRR1345329 SRR1347236 SRR1347278 SRR1347389 SRR813959 SRR815920 SRR816517 SRR816609 SRR816677 SRR821573 |
| Prostate | SRR1069209 SRR1069514 SRR1073069 SRR1074410 SRR1075126 SRR1075530 SRR1076120 SRR1077429 SRR1078164 SRR1078684 SRR1078855 SRR1080318 SRR1080696 SRR1081789 SRR1082496 SRR1083732 SRR1086441 SRR1086514 SRR1086869 SRR1091645 SRR1091990 SRR1092444 SRR1092468 SRR1092636 SRR1092913 SRR1093075 SRR1093697 SRR1096081 SRR1097344 SRR1098686 SRR1099402 SRR1105441 SRR1308860 SRR1310939 SRR1312002 SRR1315353 SRR1317751 SRR1323699 SRR1324314 SRR1326100 SRR1332360 SRR1335605 SRR1335964 SRR813108 SRR815280 SRR815542 SRR815845 SRR816818 SRR816969 SRR820234 |
| Skin- Not Sun Exposed (Suprapubic) | SRR1069048 SRR1070232 SRR1070888 SRR1073605 SRR1074289 SRR1075247 SRR1076292 SRR1077263 SRR1077898 SRR1079434 SRR1083215 SRR1083579 SRR1084299 SRR1087801 SRR1091597 SRR1094216 SRR1095503 SRR1096408 SRR1098216 SRR1100703 SRR1309920 SRR1309985 SRR1310053 SRR1311153 SRR1311224 SRR1311916 SRR1312124 SRR1312244 SRR1312645 SRR1312934 SRR1313494 SRR1314036 SRR1314137 SRR1314728 SRR1314810 SRR1315912 SRR1316438 SRR1316747 SRR1316833 SRR1317022 SRR814491 SRR815164 SRR815350 SRR815759 SRR815805 SRR818372 SRR818440 SRR819844 SRR820427 SRR820810 |
| Small Intestine- Terminal Ileum | SRR1070133 SRR1071181 SRR1072602 SRR1074934 SRR1076046 SRR1076465 SRR1077728 SRR1079973 SRR1084154 SRR1085378 SRR1087680 SRR1310497 SRR1311731 SRR1313664 SRR1319309 SRR1319301 SRR1321483 SRR1326449 SRR1326845 SRR1329508 SRR1330371 SRR1337749 SRR1337930 SRR1338402 SRR1339086 SRR1340762 SRR1340782 SRR1343136 SRR1344079 SRR1344364 SRR1351907 SRR1354400 SRR1356327 SRR1358803 SRR1359027 SRR1359587 SRR1360321 SRR1361391 SRR1365655 SRR1365767 SRR1366102 SRR1366412 SRR1367520 SRR1375371 SRR1378199 SRR1379036 SRR1380358 SRR1380436 SRR1384312 SRR1387745 |
| Stomach | SRR1068953 SRR1069166 SRR1069714 SRR1069778 SRR1070382 SRR1070549 SRR1070884 SRR1071761 SRR1072199 SRR1072700 SRR1072821 SRR1072920 SRR1073459 SRR1074066 SRR1075874 SRR1076268 SRR1076417 SRR1076990 SRR1078090 SRR1078759 SRR1079900 SRR1080672 SRR1081092 SRR1081235 SRR1081717 SRR1081935 SRR1082933 SRR1082957 SRR1083149 SRR1083191 SRR1083262 SRR1083360 SRR1083408 SRR1084252 SRR1085450 SRR1087101 SRR1088068 SRR1088117 SRR808542 SRR810689 SRR810829 SRR811193 SRR812152 SRR813234 SRR814195 SRR814268 SRR814820 SRR815326 SRR815970 SRR819719 |
| Testis | SRR1068788 SRR1068905 SRR1069734 SRR1070479 SRR1071379 SRR1071429 SRR1072845 SRR1073531 SRR1075607 SRR1076490 SRR1077753 SRR1078299 SRR1078612 SRR1079455 SRR1079612 SRR1080022 SRR1080811 SRR1080859 SRR1081357 SRR1081401 SRR1081449 SRR1081614 SRR1081663 SRR1081688 SRR1082307 SRR1083554 SRR1084347 SRR1087055 SRR1087535 SRR1088241 SRR1308288 SRR1309425 SRR1311329 SRR1312288 SRR1314014 SRR807517 |

TABLE 6-continued

Accession numbers of the GTEx datasets used in this study

| Tissue | Accession numbers (SRA) of randomly selected donors |
|---|---|
|  | SRR808065 SRR809667 SRR810531 SRR810899 SRR811447 SRR812912 SRR813431 SRR814082 SRR814943 SRR815588 SRR817512 SRR818850 SRR820839 SRR821518 |
| Thyroid | SRR597952 SRR598068 SRR598100 SRR598364 SRR598565 SRR598645 SRR599122 SRR599346 SRR599412 SRR601157 SRR601359 SRR601525 SRR601549 SRR601843 SRR601962 SRR602338 SRR602389 SRR602951 SRR602978 SRR603036 SRR603268 SRR603726 SRR603834 SRR603942 SRR604148 SRR604294 SRR604342 SRR607502 SRR607679 SRR607705 SRR608064 SRR608120 SRR608512 SRR613018 SRR613258 SRR613402 SRR613711 SRR613795 SRR613975 SRR614023 SRR614107 SRR614275 SRR614743 SRR614912 SRR615285 SRR615347 SRR615491 SRR615886 SRR654969 SRR655696 |
| Uterus | SRR1069466 SRR1071737 SRR1073483 SRR1074430 SRR1075850 SRR1077159 SRR1077211 SRR1077996 SRR1078114 SRR1078188 SRR1078212 SRR1079213 SRR1079408 SRR1079874 SRR1080342 SRR1082128 SRR1084553 SRR1085358 SRR1086369 SRR1309745 SRR1313991 SRR1319242 SRR1319991 SRR1321720 SRR1323234 SRR1329423 SRR1330082 SRR1336682 SRR1338468 SRR1339258 SRR1343943 SRR1353686 SRR1358126 SRR1360280 SRR1361138 SRR1361838 SRR1363718 SRR1374543 SRR1381372 SRR1382780 SRR1383237 SRR1387132 SRR1388257 SRR808704 SRR810105 SRR815256 SRR817817 SRR818139 SRR818646 SRR820026 |

TABLE 7a

Information about samples used in this study-murine samples

| SampleName | BiosampleType | Strain | H-2-D | H-2-K | H-2-L | Replication Type | NbCells |
|---|---|---|---|---|---|---|---|
| EL4 | cell line | C57BL/6 | b | b | — | unreplicated | 5 000 000 |
| mTEChi_1 | primary cells | C57BL/6 | b | b | — | biological | 51 237 |
| mTEChi_2 | primary cells | C57BL/6 | b | b | — | biological | 31 686 |
| mTEChi_3 | primary cells | C57BL/6 | b | b | — | biological | 31 702 |
| CT26 | cell line | Balb/c | d | d | d | unreplicated | 5 000 000 |
| mTEChi_1 | primary cells | Balb/c | d | d | d | biological | 16 338 |
| mTEChi_2 | primary cells | Balb/c | d | d | d | biological | 19 782 |
| mTEChi_3 | primary cells | Balb/c | d | d | d | biological | 23 130 |

| SampleName | BioAnalyser_RIN | Input RNA_ng | Nucleic Acid Type | Strand Specificity | Platform | ReadType |
|---|---|---|---|---|---|---|
| EL4 | 9.95 | 4 000 | polyadenylated mRNA | strand-specific | HiSeq 2000 | Paired-end |
| mTEChi_1 | 10 | 100 | polyadenylated mRNA | strand-specific | HiSeq 2000 | Paired-end |
| mTEChi_2 | 9.2 | 100 | polyadenylated mRNA | strand-specific | HiSeq 2000 | Paired-end |
| mTEChi_3 | 9.9 | 100 | polyadenylated mRNA | strand-specific | HiSeq 2000 | Paired-end |
| CT26 | 10 | 2 000 | polyadenylated mRNA | strand-specific | HiSeq 2000 | Paired-end |
| mTEChi_1 | 9.5 | 50 | polyadenylated mRNA | strand-specific | NextSeq 500 | Paired-end |
| mTEChi_2 | 9.4 | 50 | polyadenylated mRNA | strand-specific | NextSeq 500 | Paired-end |
| mTEChi_3 | 9.2 | 50 | polyadenylated mRNA | strand-specific | NextSeq 500 | Paired-end |

| SampleName | Read Length_bp | Total Nb Reads | Accession Number_GEO | NbRepMS | NbCellsMS (×10^6) | Accession Code_MS data |
|---|---|---|---|---|---|---|
| EL4 | 100 | 240372644 | GSE111092 | 3 | 250 | PXD009064 |
| mTEChi_1 | 100 | 159208840 | GSE111092 | N/A | N/A | N/A |
| mTEChi_2 | 100 | 145643202 | GSE111092 | N/A | N/A | N/A |
| mTEChi_3 | 100 | 152139924 | GSE111092 | N/A | N/A | N/A |
| CT26 | 100 | 247522370 | GSE111092 | 3 | 250 | PXD009065 |
| mTEChi_1 | 80 | 156128844 | GSE111092 | N/A | N/A | N/A |
| mTEChi_2 | 80 | 161566962 | GSE111092 | N/A | N/A | N/A |
| mTEChi_3 | 80 | 137929352 | GSE111092 | N/A | N/A | N/A |

TABLE 7b

Information about samples used in this study-human samples

| SampleName | Biosample Type | HLA-A | HLA-B | HLA-C | Replication Type | NbCells |
|---|---|---|---|---|---|---|
| 07H103 | primary leukemic cells | 01:01 \| 02:01 | 40:01 \| 44:02 | 03:04 \| 05:01 | unreplicated | 2 600 000 |
| 10H080 | primary leukemic cells | 02:01 \| 11:01 | 40:01 \| 44:03 | 03:04 \| 16:01 | unreplicated | 2 000 000 |
| 10H118 | primary leukemic cells | 01:01 \| 02:01 | 07:02 \| 08:01 | 07:01 \| 07:17 | unreplicated | 3 400 000 |
| 12H018 | primary leukemic cells | 02:01 \| 11:01 | 07:02 \| 35:03 | 07:02 \| 12:03 | unreplicated | 4 000 000 |
| Ic2 | tumor biopsy | 11:01 \| 23:01 | 35:01 \| 44:03 | 04:01 | unreplicated | N/A |
| Ic4 | tumor biopsy | 02:01 \| 03:01 | 07:02 | 07:02 | unreplicated | N/A |
| Ic6 | tumor biopsy | 01:01 \| 24:02 | 08:01 \| 27:13 | 02:02 \| 07:01 | unreplicated | N/A |
| 102015 | primary TECs | N/A | N/A | N/A | unreplicated | 33 076 |
| 062015 | primary TECs | N/A | N/A | N/A | unreplicated | 84 198 |
| S5 | primary mTECs | N/A | N/A | N/A | unreplicated | 59 197 |
| S9 | primary mTECs | N/A | N/A | N/A | unreplicated | 100 719 |
| S0 | primary mTECs | N/A | N/A | N/A | unreplicated | 50 058 |
| S11 | primary mTECs | N/A | N/A | N/A | unreplicated | 100 506 |

| Sample Name | BioAnalyser_RIN | Input RNA_ng | Nucleic Acid Type | Strand Specificity | Platform | ReadType |
|---|---|---|---|---|---|---|
| 07H103 | 10 | 500 | polyadenylated mRNA | strand-specific | HiSeq 2000 | Paired-end |
| 10H080 | 10 | 500 | polyadenylated mRNA | strand-specific | HiSeq 2000 | Paired-end |
| 10H118 | 9 | 500 | polyadenylated mRNA | strand-specific | HiSeq 2000 | Paired-end |
| 12H018 | 9 | 500 | polyadenylated mRNA | strand-specific | HiSeq 2000 | Paired-end |
| Ic2 | 9.2 | 4 000 | polyadenylated mRNA | strand-specific | HiSeq 2000 | Paired-end |
| Ic4 | 9.4 | 4 000 | polyadenylated mRNA | strand-specific | HiSeq 2000 | Paired-end |
| Ic6 | 8.9 | 4 000 | polyadenylated mRNA | strand-specific | HiSeq 2000 | Paired-end |
| 102015 | 7 | 8 | polyadenylated mRNA | strand-specific | NextSeq 500 | Paired-end |
| 062015 | 7 | 13 | polyadenylated mRNA | strand-specific | NextSeq 500 | Paired-end |
| S5 | 7 | 41 | polyadenylated mRNA | strand-specific | NextSeq 500 | Paired-end |
| S9 | 8 | 56 | polyadenylated mRNA | strand-specific | NextSeq 500 | Paired-end |
| S0 | 8 | 68 | polyadenylated mRNA | strand-specific | NextSeq 500 | Paired-end |
| S11 | 7 | 59 | polyadenylated mRNA | strand-specific | NextSeq 500 | Paired-end |

| Sample Name | Read Length_bp | Total Nb Reads | Accession Number_GEO | NbRepMS | NbCellsMS (×10^6) | Accession Code_MS data |
|---|---|---|---|---|---|---|
| 07H103 | 100 | 105 863 640 | GSE113972 | 3 | 650 | PXD009749 |
| 10H080 | 100 | 129 444 492 | GSE113972 | 3/4 | 500/100 | PXD009753/ PXD007935 |
| 10H118 | 100 | 226 508 070 | GSE113972 | 3 | 700 | PXD009750 |
| 12H018 | 100 | 161 724 658 | GSE113972 | 3 | 465 | PXD009751 |
| Ic2 | 100 | 268 396 930 | GSE113972 | 2 | N/A | PXD009752 |
| Ic4 | 100 | 262 531 548 | GSE113972 | 2 | N/A | PXD009754 |
| Ic6 | 100 | 246 868 078 | GSE113972 | 2 | N/A | PXD009755 |
| 102015 | 80 | 134 624 214 | N/A | strand-specific | NextSeq 500 | Paired-end |
| 062015 | 80 | 136 558 238 | N/A | strand-specific | NextSeq 500 | Paired-end |
| S5 | 80 | 200 363 532 | N/A | strand-specific | NextSeq 500 | Paired-end |
| S9 | 80 | 229 281 098 | N/A | strand-specific | NextSeq 500 | Paired-end |

TABLE 7b-continued

| | | Information about samples used in this study-human samples | | | | |
|---|---|---|---|---|---|---|
| S0 | 80 | 231 185 678 | N/A | strand-specific | NextSeq 500 | Paired-end |
| S11 | 80 | 251 770 122 | N/A | strand-specific | NextSeq 500 | Paired-end |

Although the present invention has been described hereinabove by way of specific embodiments thereof, it can be modified, without departing from the spirit and nature of the subject invention as defined in the appended claims. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Mlecnik, B., et al. The tumor microenvironment and immunoscore are critical determinants of dissemination to distant metastasis. *Sci Transl Med* 8, 327ra326 (2016).
2. Charoentong, P., et al. Pan-cancer immunogenomic analyses reveal genotype-immunophenotype relationships and predictors of response to checkpoint blockade. *Cell Rep* 18, 248-262 (2017).
3. Shao, W., et al. The systeMHC Atlas project. *Nucleic Acids Res* 46, D1237-D1247 (2018).
4. Martin, S. D., Coukos, G., Holt, R. A. & Nelson, B. H. Targeting the undruggable: Immunotherapy meets personalized oncology in the genomic era. *Ann Oncol* 26, 2367-2374 (2015).
5. Marty, R., et al. MHC-I genotype restricts the oncogenic mutational landscape. *Cell* 171, 1272-1283 e1215 (2017).
6. Zhong, S., et al. T-cell receptor affinity and avidity defines antitumor response and autoimmunity in T-cell immunotherapy. *Proc Natl Acad Sci USA* 110, 6973-6978 (2013).
7. Sahin, U., et al. Personalized RNA mutanome vaccines mobilize poly-specific therapeutic immunity against cancer. *Nature* 547, 222-226 (2017).
8. Turajlic, S., et al. Insertion-and-deletion-derived tumour-specific neoantigens and the immunogenic phenotype: a pan-cancer analysis. *Lancet Oncol* 18, 1009-1021 (2017).
9. Yadav, M., et al. Predicting immunogenic tumour mutations by combining mass spectrometry and exome sequencing. *Nature* 515, 572-576 (2014).
10. Pearson, H., et al. MHC class I-associated peptides derive from selective regions of the human genome. *J Clin Invest* 126, 4690-4701 (2016).
11. Tran, E., et al. Immunogenicity of somatic mutations in human gastrointestinal cancers. *Science* 350, 1387-1390 (2015).
12. Gros, A., et al. Prospective identification of neoantigen-specific lymphocytes in the peripheral blood of melanoma patients. *Nat Med* 22, 433-438 (2016).
13. Bassani-Sternberg, M., et al. Direct identification of clinically relevant neoepitopes presented on native human melanoma tissue by mass spectrometry. *Nat Commun* 7, 13404 (2016).
14. Mertens, F., Johansson, B., Fioretos, T. & Mitelman, F. The emerging complexity of gene fusions in cancer. *Nat Rev Cancer* 15, 371-381 (2015).
15. Baca, S. C., et al. Punctuated evolution of prostate cancer genomes. *Cell* 153, 666-677
16. Hayward, N. K., et al. Whole-genome landscapes of major melanoma subtypes. *Nature* 545, 175-180 (2017).
17. Khurana, E., et al. Role of non-coding sequence variants in cancer. *Nat Rev Genet* 17, 93-108 (2016).
18. Laumont, C. M., et al. Global proteogenomic analysis of human MHC class I-associated peptides derived from non-canonical reading frames. *Nat Commun* 7, 10238 (2016).
19. Rooney, M. S., Shukla, S. A., Wu, C. J., Getz, G. & Hacohen, N. Molecular and genetic properties of tumors associated with local immune cytolytic activity. *Cell* 160, 48-61 (2015).
20. Charoentong, P., et al. Pan-cancer Immunogenomic Analyses Reveal Genotype-Immunophenotype Relationships and Predictors of Response to Checkpoint Blockade. *Cell Rep* 18, 248-262 (2017).
21. Anwar, S. L., Wulaningsih, W. & Lehmann, U. Transposable Elements in Human Cancer: Causes and Consequences of Deregulation. *Int J Mol Sci* 18(2017).
22. Kassiotis, G. & Stoye, J. P. Immune responses to endogenous retroelements: taking the bad with the good. *Nat Rev Immunol* 16, 207-219 (2016).
23. Kershaw, M. H., et al. Immunization against endogenous retroviral tumor-associated antigens. *Cancer Res* 61, 7920-7924 (2001).
24. Sacha, J. B., et al. Vaccination with cancer- and HIV infection-associated endogenous retrotransposable elements is safe and immunogenic. *J Immunol* 189, 1467-1479 (2012).
25. Malarkannan, S., Serwold, T., Nguyen, V., Sherman, L. A. & Shastri, N. The mouse mammary tumor virus env gene is the source of a CD8+ T-cell-stimulating peptide presented by a major histocompatibility complex class I molecule in a murine thymoma. *Proc Natl Acad Sci USA* 93, 13991-13996 (1996).
26. Huang, A. Y., et al. The immunodominant major histocompatibility complex class I-restricted antigen of a murine colon tumor derives from an endogenous retroviral gene product. *Proc Natl Acad Sci USA* 93, 9730-9735 (1996).
27. Schiavetti, F., Thonnard, J., Colau, D., Boon, T. & Coulie, P. G. A human endogenous retroviral sequence encoding an antigen recognized on melanoma by cytolytic T lymphocytes. *Cancer Res* 62, 5510-5516 (2002).
28. Takahashi, Y., et al. Regression of human kidney cancer following allogeneic stem cell transplantation is associated with recognition of an HERV-E antigen by T cells. *J Clin Invest* 118, 1099-1109 (2008).
29. Kim, M. J., Miller, C. M., Shadrach, J. L., Wagers, A. J. & Serwold, T. Young, proliferative thymic epithelial cells engraft and function in aging thymuses. *J Immunol* 194, 4784-4795 (2015).
30. Dobin, A., et al. STAR: ultrafast universal RNA-seq aligner. *Bioinformatics* 29, 15-21 (2013).
31. Quinlan, A. R. & Hall, I. M. BEDTools: a flexible suite of utilities for comparing genomic features. *Bioinformatics* 26, 841-842 (2010).

32. Caron, E., et al. The MHC I immunopeptidome conveys to the cell surface an integrative view of cellular regulation. *Mol Syst Biol* 7, 533 (2011).
33. Andreatta, M. & Nielsen, M. Gapped sequence alignment using artificial neural networks: application to the MHC class I system. *Bioinformatics* 32, 511-517 (2016).
34. Robinson, J. T., et al. Integrative genomics viewer. *Nat Biotechnol* 29, 24-26 (2011).
35. Bereman, M. S., et al. An Automated Pipeline to Monitor System Performance in Liquid Chromatography-Tandem Mass Spectrometry Proteomic Experiments. *J Proteome Res* 15, 4763-4769 (2016).
36. Yue, F., et al. A comparative encyclopedia of DNA elements in the mouse genome. *Nature* 515, 355-364 (2014).
37. Barbosa-Morais, N. L., et al. The evolutionary landscape of alternative splicing in vertebrate species. *Science* 338, 1587-1593 (2012).
38. Patenaude, J. & Perreault, C. Thymic Mesenchymal Cells Have a Distinct Transcriptomic Profile. *J Immunol* 196, 4760-4770 (2016).
39. St-Pierre, C., Trofimov, A., Brochu, S., Lemieux, S. & Perreault, C. Differential Features of AIRE-Induced and AIRE-Independent Promiscuous Gene Expression in Thymic Epithelial Cells. *J Immunol* 195, 498-506 (2015).
40. Dumont-Lagace, M., St-Pierre, C. & Perreault, C. Sex hormones have pervasive effects on thymic epithelial cells. *Sci Rep* 5, 12895 (2015).
41. Dumont-Lagace, M., Brochu, S., St-Pierre, C. & Perreault, C. Adult thymic epithelium contains nonsenescent label-retaining cells. *J Immunol* 192, 2219-2226 (2014).
42. de Verteuil, D. A., et al. Immunoproteasomes shape the transcriptome and regulate the function of dendritic cells. *J Immunol* 193, 1121-1132 (2014).
43. de Verteuil, D., et al. Deletion of immunoproteasome subunits imprints on the transcriptome and has a broad impact on peptides presented by major histocompatibility complex I molecules. *Mol Cell Proteomics* 9, 2034-2047 (2010).
44. Moon, J. J., et al. Naive CD4(+) T cell frequency varies for different epitopes and predicts repertoire diversity and response magnitude. *Immunity* 27, 203-213 (2007).
45. Legoux, F. P. & Moon, J. J. Peptide:MHC tetramer-based enrichment of epitope-specific T cells. *J Vis Exp* (2012).
46. McFarland, H. I., Nahill, S. R., Maciaszek, J. W. & Welsh, R. M. CD11b (Mac-1): a marker for CD8+ cytotoxic T cell activation and memory in virus infection. *J Immunol* 149, 1326-1333 (1992).
47. Chadburn, A., lnghirami, G. & Knowles, D. M. Hairy cell leukemia-associated antigen LeuM5 (CD11c) is preferentially expressed by benign activated and neoplastic CD8 T cells. *Am J Pathol* 136, 29-37 (1990).
48. Nesvizhskii, A. I. Proteogenomics: concepts, applications and computational strategies. *Nat Methods* 11, 1114-1125 (2014).
49. Noble, W. S. Mass spectrometrists should search only for peptides they care about. *Nat Methods* 12, 605-608 (2015).
50. Murphy, J. P., et al. MHC-I Ligand Discovery Using Targeted Database Searches of Mass Spectrometry Data: Implications for T-Cell Immunotherapies. *J Proteome Res* 16, 1806-1816 (2017).
51. Granados, D. P., et al. Impact of genomic polymorphisms on the repertoire of human MHC class I-associated peptides. *Nat Commun* 5, 3600 (2014).
52. Bassani-Sternberg, M., Pletscher-Frankild, S., Jensen, L. J. & Mann, M. Mass spectrometry of human leukocyte antigen class I peptidomes reveals strong effects of protein abundance and turnover on antigen presentation. *Mol Cell Proteomics* 14, 658-673 (2015).
53. Fortier, M. H., et al. The MHC class I peptide repertoire is molded by the transcriptome. *J Exp Med* 205, 595-610 (2008).
54. Jenkins, M. K. & Moon, J. J. The role of naive T cell precursor frequency and recruitment in dictating immune response magnitude. *J Immunol* 188, 4135-4140 (2012).
55. Obar, J. J., Khanna, K. M. & Lefrancois, L. Endogenous naive CD8+ T cell precursor frequency regulates primary and memory responses to infection. *Immunity* 28, 859-869 (2008).
56. La Gruta, N. L., et al. Primary CTL response magnitude in mice is determined by the extent of naive T cell recruitment and subsequent clonal expansion. *J Clin Invest* 120, 1885-1894 (2010).
57. Mueller, S. N., Gebhardt, T., Carbone, F. R. & Heath, W. R. Memory T cell subsets, migration patterns, and tissue residence. *Annu Rev Immunol* 31, 137-161 (2013).
58. Baaten, B. J., Tinoco, R., Chen, A. T. & Bradley, L. M. Regulation of Antigen-Experienced T Cells: Lessons from the Quintessential Memory Marker CD44. *Front Immunol* 3, 23 (2012).
59. Laugel, B., et al. Different T cell receptor affinity thresholds and CD8 coreceptor dependence govern cytotoxic T lymphocyte activation and tetramer binding properties. *J Biol Chem* 282, 23799-23810 (2007).
60. Richards, D. M., Kyewski, B. & Feuerer, M. Re-examining the Nature and Function of Self-Reactive T cells. *Trends Immunol* 37, 114-125 (2016).
61. McGranahan, N., et al. Clonal neoantigens elicit T cell immunoreactivity and sensitivity to immune checkpoint blockade. *Science* 351, 1463-1469 (2016).
62. Assarsson, E., et al. A quantitative analysis of the variables affecting the repertoire of T cell specificities recognized after vaccinia virus infection. *J Immunol* 178, 7890-7901 (2007).
63. Martin, S. D., et al. Low Mutation Burden in Ovarian Cancer May Limit the Utility of Neoantigen-Targeted Vaccines. *PLoS One* 11, e0155189 (2016).
64. Rudensky, A., Preston-Hurlburt, P., Hong, S. C., Barlow, A. & Janeway, C. A., Jr. Sequence analysis of peptides bound to MHC class II molecules. *Nature* 353, 622-627 (1991).
65. Meydan, C., Otu, H. H. & Sezerman, O. U. Prediction of peptides binding to MHC class I and II alleles by temporal motif mining. *BMC Bioinformatics* 14 Suppl 2, S13 (2013).
66. Szpakowski, S., et al. Loss of epigenetic silencing in tumors preferentially affects primate-specific retroelements. *Gene* 448, 151-167 (2009).
67. Capietto, A. H., Jhunjhunwala, S. & Delamarre, L. Characterizing neoantigens for personalized cancer immunotherapy. *Curr Opin Immunol* 46, 58-65 (2017).
68. Helft, J., et al. GM-CSF Mouse Bone Marrow Cultures Comprise a Heterogeneous Population of CD11c(+) MHCII(+) Macrophages and Dendritic Cells. *Immunity* 42, 1197-1211 (2015).
69. Wimmers, F., Schreibelt, G., Skold, A. E., Figdor, C. G. & De Vries, I. J. Paradigm Shift in Dendritic Cell-Based Immunotherapy: From in vitro Generated Monocyte-Derived DCs to Naturally Circulating DC Subsets. *Front Immunol* 5, 165 (2014).
70. Guilliams, M. & Malissen, B. A Death Notice for In-Vitro-Generated GM-CSF Dendritic Cells? *Immunity* 42, 988-990 (2015).

71. Melief, C. J., van Hall, T., Arens, R., Ossendorp, F. & van der Burg, S. H. Therapeutic cancer vaccines. *J Clin Invest* 125, 3401-3412 (2015).
72. Guo, C., et al. Therapeutic cancer vaccines: past, present, and future. *Adv Cancer Res* 119, 421-475 (2013).
73. Melero, I., et al. Therapeutic vaccines for cancer: an overview of clinical trials. *Nat Rev Clin Oncol* 11, 509-524 (2014).
74. Baruch, E. N., Berg, A. L., Besser, M. J., Schachter, J. & Markel, G. Adoptive T cell therapy: An overview of obstacles and opportunities. *Cancer* 123, 2154-2162 (2017).
75. Rosenberg, S. A. & Restifo, N. P. Adoptive cell transfer as personalized immunotherapy for human cancer. *Science* 348, 62-68 (2015).
76. Stoeckle, C., et al. Isolation of myeloid dendritic cells and epithelial cells from human thymus. J Vis Exp, e50951 (2013).
77. Marcais, G. & Kingsford, C. A fast, lock-free approach for efficient parallel counting of occurrences of k-mers. Bioinformatics 27, 764-770 (2011).
1a. Lanoix, J., et al. Comparison of the MHC I immunopeptidome repertoire of B-cell lymphoblasts using two isolation methods. Proteomics, e1700251 (2018).
2a. Kim, M. J., Miller, C. M., Shadrach, J. L., Wagers, A. J. & Serwold, T. Young, proliferative thymic epithelial cells engraft and function in aging thymuses. J Immunol 194, 4784-4795 (2015).
3a. Stoeckle, C., et al. Isolation of myeloid dendritic cells and epithelial cells from human thymus. J Vis Exp, e50951 (2013).
4a. Dobin, A., et al. STAR: Ultrafast universal RNA-seq aligner. Bioinformatics 29, 15-21 (2013).
5a. Daouda, T., Perreault, C. & Lemieux, S. pyGeno: A python package for precision medicine and proteogenomics. F1000Res 5, 381 (2016).
6a. Marcais, G. & Kingsford, C. A fast, lock-free approach for efficient parallel counting of occurrences of k-mers. Bioinformatics 27, 764-770 (2011).
7a. Caron, E., et al. The MHC I immunopeptidome conveys to the cell surface an integrative view of cellular regulation. Mol Syst Biol 7, 533 (2011).
8a. Andreatta, M. & Nielsen, M. Gapped sequence alignment using artificial neural networks: Application to the MHC class I system. Bioinformatics 32, 511-517 (2016).
9a. Robinson, J. T., et al. Integrative genomics viewer. Nat Biotechnol 29, 24-26 (2011).
10a. Yue, F., et al. A comparative encyclopedia of DNA elements in the mouse genome. Nature 515, 355-364 (2014).
11a. Sloan, C. A., et al. ENCODE data at the ENCODE portal. Nucleic Acids Res 44, D726-732 (2016).
12a. Bereman, M. S., et al. An automated pipeline to monitor system performance in liquid chromatography-tandem mass spectrometry proteomic experiments. J Proteome Res 15, 4763-4769 (2016).
13a. de Verteuil, D., et al. Deletion of immunoproteasome subunits imprints on the transcriptome and has a broad impact on peptides presented by major histocompatibility complex I molecules. Mol Cell Proteomics 9, 2034-2047 (2010).
14a. Vincent, K., et al. Rejection of leukemic cells requires antigen-specific T cells with high functional avidity. Biol Blood Marrow Transplant 20, 37-45 (2014).
15a. Moon, J. J., et al. Naive CD4(+) T cell frequency varies for different epitopes and predicts repertoire diversity and response magnitude. Immunity 27, 203-213 (2007).
16a. Legoux, F. P. & Moon, J. J. Peptide:MHC tetramer-based enrichment of epitope-specific T cells. J Vis Exp 68, 4420 (2012).
17a. McFarland, H. I., Nahill, S. R., Maciaszek, J. W. & Welsh, R. M. CD11 b (Mac-1): A marker for CD8+ cytotoxic T cell activation and memory in virus infection. J Immunol 149, 1326-1333 (1992).
18a. Chadburn, A., Inghirami, G. & Knowles, D. M. Hairy cell leukemia-associated antigen LeuM5 (CD11c) is preferentially expressed by benign activated and neoplastic CD8 T cells. Am J Pathol 136, 29-37 (1990)
19a. Vizcaino, J. A., et al. 2016 update of the PRIDE database and its related tools. Nucleic Acids Res 44, 11033 (2016).

What is claimed is:

1. A method of treating a human subject suffering from leukemia or lung cancer, the method comprising administering to the subject an effective amount of a pharmaceutical composition comprising (i) a peptide of 14 amino acids or less comprising one of the amino acid sequences set forth in any one of SEQ ID NOs: 33, 29, 30, 31, 35, 36, 37 and 38, or a nucleic acid encoding said peptide, if said subject suffers from lung cancer, or (ii) a peptide of 14 amino acids or less comprising one of the amino acid sequences set forth in any one of SEQ ID NOs: 17-27, or a nucleic acid encoding said peptide, if said subject suffers from leukemia.

2. The method of claim 1, wherein said leukemia is B-cell acute lymphoblastic leukemia (B-ALL).

3. The method of claim 1, wherein said lung cancer is a non-small cell lung cancer (NSCLC).

4. The method of claim 1, further comprising administering at least one additional antitumor agent or therapy to the subject, wherein said at least one additional antitumor agent or therapy is a chemotherapeutic agent, immunotherapy, an immune checkpoint inhibitor, radiotherapy or surgery.

5. The method of claim 4, wherein said at least one additional antitumor agent or therapy is an immune checkpoint inhibitor.

6. The method of claim 1, wherein the pharmaceutical composition comprises a nucleic acid encoding said peptide.

7. The method of claim 6, wherein the nucleic acid is an mRNA.

8. The method of claim 7, wherein the mRNA is encapsulated within a vesicle.

9. The method of claim 8, wherein the vesicle is a liposome.

10. The method of claim 1, wherein the pharmaceutical composition further comprises an adjuvant.

11. The method of claim 1, wherein the pharmaceutical composition comprises a peptide of 14 amino acids or less comprising the amino acid sequence set forth in SEQ ID NO: 33, or a nucleic acid encoding said peptide.

12. The method of claim 1, wherein the pharmaceutical composition comprises a peptide consisting of one of the amino acid sequences set forth in any one of SEQ ID NOs: 33, 29, 30, 31, 35, 36, 37 and 38, or a nucleic acid encoding said peptide.

13. The method of claim 1, wherein the pharmaceutical composition comprises a peptide consisting of one of the amino acid sequences set forth in any one of SEQ ID NOs: 17-27, or a nucleic acid encoding said peptide.

* * * * *